US009090590B2

(12) United States Patent
Pflumm et al.

(10) Patent No.: US 9,090,590 B2
(45) Date of Patent: Jul. 28, 2015

(54) ORGANIC COMPOUNDS FOR ELECTROLUMINESCENT DEVICES

(75) Inventors: Christof Pflumm, Frankfurt am Main (DE); Arne Buesing, Frankfurt am Main (DE); Amir Hossain Parham, Frankfurt am Main (DE); Rocco Fortte, Frankfurt am Main (DE); Holger Heil, Frankfurt am Main (DE); Philipp Stoessel, Frankfurt am Main (DE); Teresa Mujica-Fernaud, Darmstadt (DE)

(73) Assignee: Merck Patent GmbH (DE)

( * ) Notice: Subject to any disclaimer, the term of this patent is extended or adjusted under 35 U.S.C. 154(b) by 247 days.

(21) Appl. No.: 13/508,853

(22) PCT Filed: Oct. 14, 2010

(86) PCT No.: PCT/EP2010/006298
§ 371 (c)(1),
(2), (4) Date: May 9, 2012

(87) PCT Pub. No.: WO2011/057701
PCT Pub. Date: May 19, 2011

(65) Prior Publication Data
US 2013/0053558 A1 Feb. 28, 2013

(30) Foreign Application Priority Data
Nov. 10, 2009 (DE) .......................... 10 2009 052 428

(51) Int. Cl.
| | | |
|---|---|---|
| *C07D 403/10* | (2006.01) | |
| *C07D 405/10* | (2006.01) | |
| *C07D 407/10* | (2006.01) | |
| *C07D 409/10* | (2006.01) | |
| *C07D 413/10* | (2006.01) | |
| *C07D 417/10* | (2006.01) | |
| *C09K 11/06* | (2006.01) | |
| *H01L 51/50* | (2006.01) | |
| *H01L 51/54* | (2006.01) | |
| *H05B 33/14* | (2006.01) | |
| *H01L 51/00* | (2006.01) | |
| *C09B 57/00* | (2006.01) | |
| *C09B 1/00* | (2006.01) | |

(52) U.S. Cl.
CPC ............ *C07D 403/10* (2013.01); *C07D 405/10* (2013.01); *C07D 407/10* (2013.01); *C07D 409/10* (2013.01); *C09B 1/00* (2013.01); *C09B 57/00* (2013.01); *C09B 57/001* (2013.01); *H01L 51/0055* (2013.01); *H01L 51/0058* (2013.01); *H01L 51/0085* (2013.01); *H01L 51/0087* (2013.01); *H01L 51/0088* (2013.01); *H01L 51/5012* (2013.01); *H01L 51/5016* (2013.01); *Y02E 10/549* (2013.01)

(58) Field of Classification Search
USPC ......... 548/418, 419, 125, 126, 127, 128, 131, 548/134, 136, 146, 152, 206, 207, 215, 217, 548/240, 241, 250, 255, 262.2; 544/262, 544/264, 283, 349, 353; 549/29, 49, 429, 549/546; 345/76, 82; 257/40
See application file for complete search history.

(56) References Cited

U.S. PATENT DOCUMENTS

| | | | | |
|---|---|---|---|---|
| 6,800,655 | B2 * | 10/2004 | Jong et al. ..................... | 514/410 |
| 8,049,411 | B2 * | 11/2011 | Kato et al. .................... | 313/504 |
| 2001/0047681 | A1 | 12/2001 | Burkardt et al. | |
| 2008/0220285 | A1 | 9/2008 | Vestweber et al. | |
| 2009/0261300 | A1 | 10/2009 | Watanabe | |
| 2009/0261717 | A1 | 10/2009 | Buesing et al. | |
| 2011/0272684 | A1 | 11/2011 | Parham et al. | |
| 2012/0097899 | A1 | 4/2012 | Parham et al. | |

FOREIGN PATENT DOCUMENTS

| | | |
|---|---|---|
| DE | 10025846 A1 | 11/2001 |
| EP | 2080762 A1 | 7/2009 |
| EP | 2172534 A1 | 4/2010 |
| JP | 2008-081494 A | 4/2008 |
| JP | 2008-545630 A | 12/2008 |
| JP | 4388590 B2 | 12/2009 |
| KR | 2009-0093897 A | 9/2009 |
| WO | WO-2006122630 A1 | 11/2006 |
| WO | WO-2008/006449 A1 | 1/2008 |
| WO | WO-2009/016964 A1 | 2/2009 |
| WO | WO-2010083872 A2 | 7/2010 |
| WO | WO-2011000455 A1 | 1/2011 |

OTHER PUBLICATIONS

Rapenne, Gwénaël, et al., "Molecular Machines: Synthesis and Characterization of Two Prototypes of Molecular Wheelbarrows", Tetrahedron, vol. 63, (2007), pp. 7018-7026.
Wu, Yao-Ting, et al., "Synthesis of Fluoranthenes and Indenocorannulenes: Elucidation of Chiral Stereoisomers on the Basis of Static Molecular Bowls", J. Am. Chem. Soc., vol. 128, (2006), pp. 6870-6884.
Erian, Ayman Wahba, et al., "An Easy Direct Conversion of Pyridine- and Pyrimidine-Thiones into Multi-Fused Heterocyclic Compounds", Bull. Chem. Soc. Jpn., vol. 71, (1998), pp. 2387-2391.
International Search Report for PCT/EP2010/006298 mailed Apr. 8, 2011.

* cited by examiner

*Primary Examiner* — Venkataraman Balasubramanian
(74) *Attorney, Agent, or Firm* — Drinker Biddle & Reath LLP

(57) ABSTRACT

The invention relates to compounds of the formula (1), to a method for producing compounds of the formula (1), to the use of the compounds in electronic devices and to electronic devices containing compounds according to formula (1), preferably as electron transport materials, as matrix materials, as electron blocking materials or as emitting materials.

2 Claims, No Drawings

ORGANIC COMPOUNDS FOR ELECTROLUMINESCENT DEVICES

CROSS-REFERENCE TO RELATED APPLICATIONS

This application is a national stage application (under 35 U.S.C. §371) of PCT/EP2010/006298, filed Oct. 14, 2010, which claims benefit of German Application 10 2009 052 428.2, filed Nov. 10, 2009.

The present invention describes novel compounds of the formula (1) which can preferably be employed as electron-transport materials, as matrix materials for phosphorescent or fluorescent dopants or as fluorescent emitter materials in electronic devices. The invention furthermore relates to a process for the preparation of the compounds according to the invention and to electronic devices comprising one or more compounds according to the invention.

Organic semiconductors are being developed for a number of different electronic applications. The structure of organic electroluminescent devices (OLEDs) in which these organic semiconductors are employed as functional materials is described, for example, in U.S. Pat. Nos. 4,539,507, 5,151,629, EP 0676461 and WO 98/27136. However, further improvements are still necessary. Thus, there is still a need for improvement, in particular with respect to the lifetime, efficiency and operating voltage of organic electroluminescent devices. It is furthermore advantageous for the compounds to have high thermal stability and a high glass-transition temperature and to be sublimable without decomposition.

In particular in the case of electron-transport materials, improvements in the material properties are desirable since the properties of the electron-transport material exert a significant influence on the above-mentioned properties of the organic electroluminescent device. In particular, there is a demand for electron-transport materials which result in good efficiency, a long lifetime and a low operating voltage of the electronic devices.

It would be desirable here to have available electron-transport materials which result in better electron injection into the emitting layer, since an electron-richer emission layer results in better efficiency. In addition, better injection enables the operating voltage to be reduced. Further improvements in the electron-transport material are therefore necessary for this purpose.

In the context of the present invention, it has been found that the compounds according to the invention are highly suitable for use as electron-transport materials in organic electroluminescent devices and therefore represent an advantageous alternative to the materials known from the prior art, such as, for example, $AlQ_3$ (cf. U.S. Pat. No. 4,539,507).

For fluorescent OLEDs, especially condensed aromatic compounds, in particular anthracene derivatives, are used in accordance with the prior art as matrix materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl) anthracene derivatives for use in OLEDs. Further anthracene derivatives are disclosed in WO 01/076323, in WO 01/021729, in WO 04/013073, in WO 04/018588, in WO 03/087023 or in WO 04/018587. Matrix materials based on aryl-substituted pyrenes and chrysenes are disclosed in WO 04/016575. Matrix materials based on benzanthracene derivatives are disclosed in WO 08/145,239. It is desirable for high-quality applications to have available further matrix materials, which preferably have improved properties.

Prior art which may be mentioned in the case of blue-emitting compounds is the use of arylvinylamines (for example WO 04/013073, WO 04/016575, WO 04/018587). However, these compounds are thermally unstable and cannot be evaporated without decomposition, which requires high technical complexity for OLED production and thus represents an industrial disadvantage. It is therefore desirable for high-quality applications to have available improved emitters, particularly with respect to device and sublimation stability and emission colour.

In the case of phosphorescent electroluminescent devices, there is a need for improvement in matrix materials for phosphorescent emitters which simultaneously result in good efficiency, a long lifetime and a low operating voltage. The properties of the matrix materials in particular are frequently limiting for the lifetime and efficiency of the organic electroluminescent device.

In accordance with the prior art, carbazole derivatives, for example bis(carbazolyl)biphenyl, are frequently used as matrix materials in the said phosphorescent electroluminescent devices. There is still a need for improvement here, in particular with respect to the lifetime and glass-transition temperature of the materials. Furthermore, ketones (WO 04/093207), phosphine oxides and sulfones (WO 05/003253) are used as matrix materials for phosphorescent emitters. In particular with ketones, low operating voltages and long lifetimes are achieved. There is still a need for improvement here, in particular with respect to the efficiency and compatibility with metal complexes which contain ketoketonate ligands, for example acetylacetonate. Furthermore, metal complexes, for example BAlq or zinc(II)bis[2-(2-benzothiazolyl)phenolate], are used as matrix materials for phosphorescent emitters. There is still a need for improvement here, in particular with respect to the operating voltage and chemical stability. Purely organic compounds are frequently more stable than these metal complexes. Thus, some of these metal complexes are sensitive to hydrolysis, which makes handling of the complexes more difficult.

There is consequently a demand for matrix materials for phosphorescent emitters which result in high efficiencies, long lifetimes and low operating voltages and which are also compatible with the phosphorescent emitters which carry ketoketonate ligands.

The applications EP 1860097, WO 2006/100896, DE 102006025846, WO 2006/122630, WO 2008/132103, WO 2008/006449, WO 2008/056746, WO 2008/149691, WO 2008/146839 and WO 2008/006449 disclose indenofluorene derivatives as functional materials for use in electronic devices.

However, there continues to be a demand both for electron-transport materials and also for fluorescent dopant materials and also for matrix materials for phosphorescent or fluorescent dopants, preferably those which have the above-mentioned advantageous properties. It is particularly preferred for the newly provided materials to be straightforward to process industrially and to be suitable for improving the efficiency of organic electroluminescent devices and increasing their lifetime.

The object of the present invention thus consists in the provision of novel compounds of this type.

It has now been found that compounds of the formula (1) are particularly highly suitable as electron-transport materials, as fluorescent emitter materials, as electron-blocking materials or as matrix materials for fluorescent or phosphorescent dopants. The respective preferred use is dependent, in particular, on the electronic properties of the substituents of the compound of the formula (1).

The invention therefore relates to a compound of the formula (1),

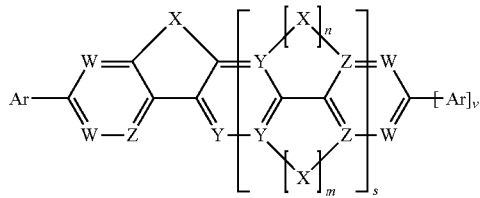

formula (1)

where the following applies to the symbols and indices used:

Ar is on each occurrence, identically or differently, an aromatic or heteroaromatic ring system having 5 to 60 ring atoms, which is optionally substituted by one or more radicals R;

X is on each occurrence, identically or differently, a group selected from —BR—, —C(R)$_2$—, —CR=CR—, —CR=N—, —Si(R)$_2$—, —O—, —S—, —S(=O)$_2$—, —NR— and P(=O)R;

Z is C if a group X is bonded to the group Z, and is on each occurrence, identically or differently, CR$^1$ or N if no group X is bonded to the group Z, with the proviso that at least one group Z or W must be equal to CR$^1$;

W is on each occurrence, identically or differently, CR$^1$ or N, with the proviso that at least one group W or Z must be equal to CR$^1$;

Y is C if a group X is bonded to the group Y, and is on each occurrence, identically or differently, CR$^2$ or N if no group X is bonded to the group Y;

R, R$^1$, R$^2$ is, identically or differently on each occurrence, H, D, F, Cl, Br, I, CHO, N(R$^3$)$_2$, C(=O)R$^3$, P(=O)(R$^3$)$_2$, S(=O)R$^3$, S(=O)$_2$R$^3$, CR$^3$=C(R$^3$)$_2$, CN, NO$_2$, Si(R$^3$)$_3$, B(OR$^3$)$_2$, OSO$_2$R$^3$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^3$, where one or more CH$_2$ groups may be replaced by —R$^3$C=CR$^3$—, —C≡C—, —Si(R$^3$)$_2$—, —Ge(R$^3$)$_2$—, —Sn(R$^3$)$_2$—, C=O, C=S, C=Se, C=NR$^3$, P(=O)(R$^3$), S=O, S(=O)$_2$, —NR$^3$—, —O—, —S— or —C(=O)NR$^3$— and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy or heteroaryloxy group having 5 to 60 aromatic ring atoms, which may be substituted by one or more radicals R$^3$, or a combination of these systems, where two or more radicals R, R$^1$ and/or R$^2$ may be linked to one another and may form a mono- or polycyclic, aliphatic or aromatic ring system;

R$^3$ is on each occurrence, identically or differently, H, D, F or an aliphatic, aromatic and/or heteroaromatic organic radical having 1 to 20 C atoms, in which, in addition, one or more H atoms may be replaced by F; two or more identical or different substituents R$^3$ here may also be linked to one another and form a mono- or polycyclic, aliphatic or aromatic ring system;

m, n are 0 or 1, with the proviso that m+n is greater than or equal to 1;

s is 1, 2 or 3, preferably 1;

v is 0 or 1, preferably 1, where, for v=0, a radical R is bonded at the relevant position;

with the further proviso that at least one group R$^1$ must be present which represents a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^3$, where one or more CH$_2$ groups may be replaced by —R$^3$C=CR$^3$—, —C≡C—, —Si(R$^3$)$_2$—, —Ge(R$^3$)$_2$—, —Sn(R$^3$)$_2$—, C=O, C=S, C=Se, C=NR$^3$, P(=O)(R$^3$), S=O, S(=O)$_2$, —NR$^3$—, —O—, —S— or —C(=O)NR$^3$— and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^3$;

and where the following compounds are excluded:

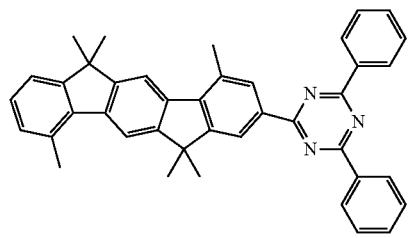
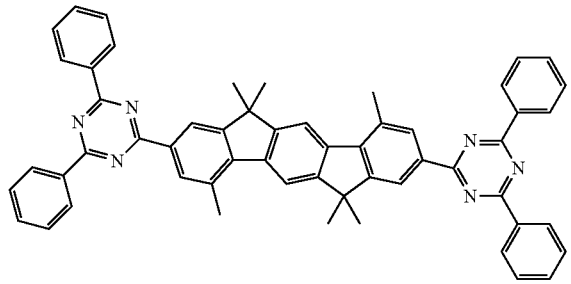
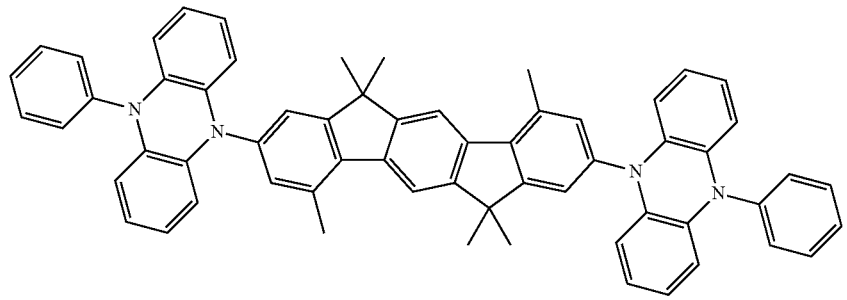

-continued
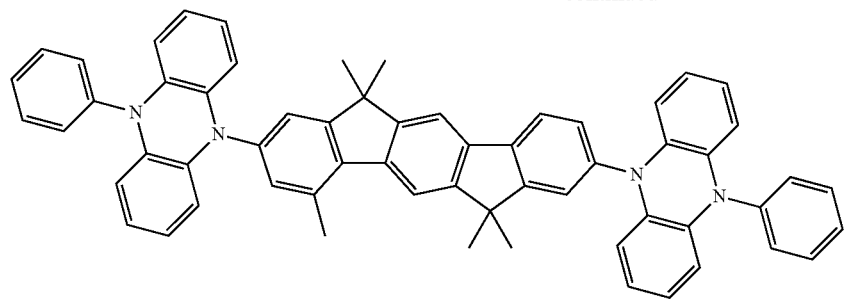
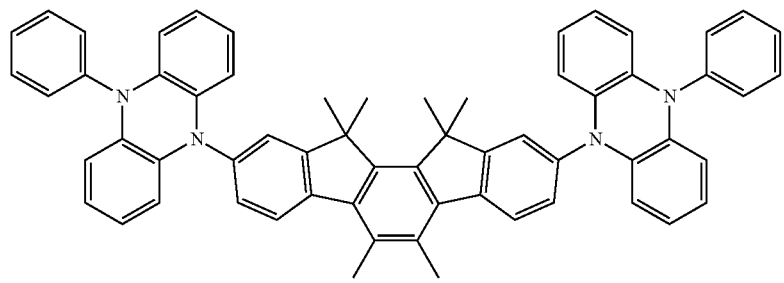
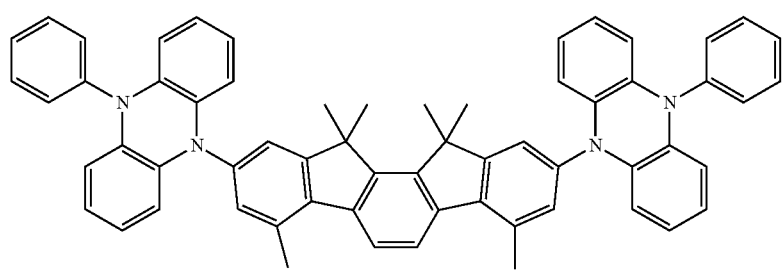
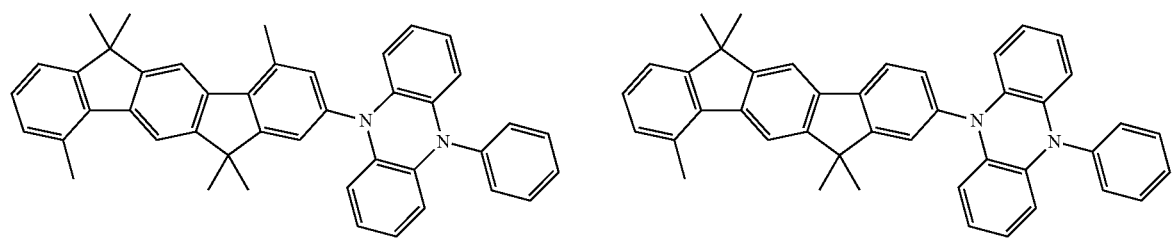
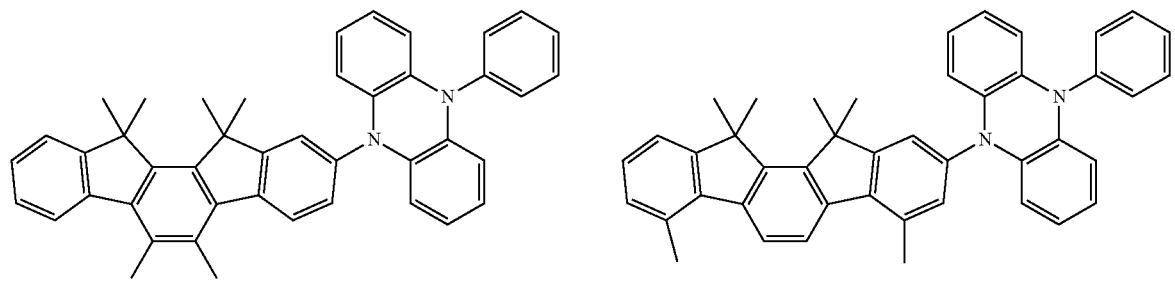
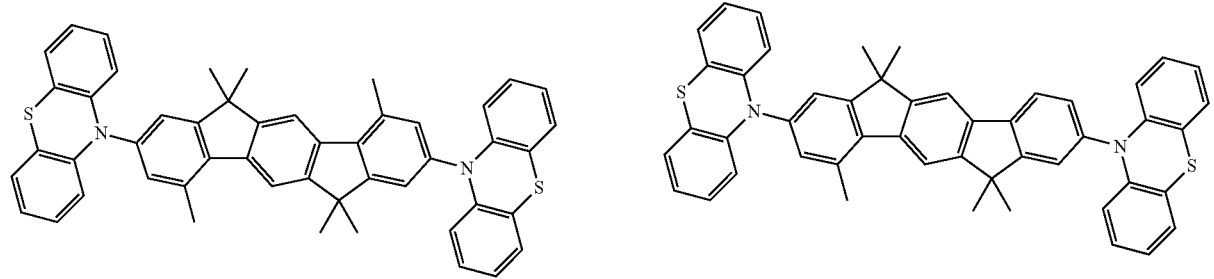

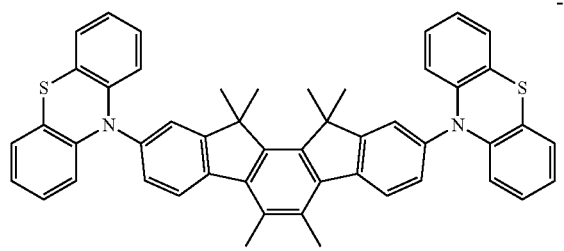
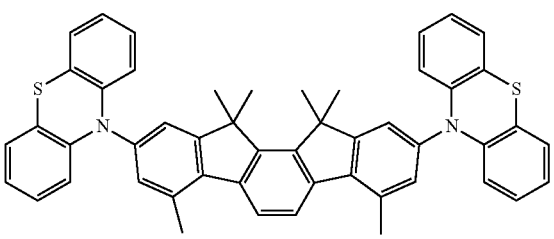
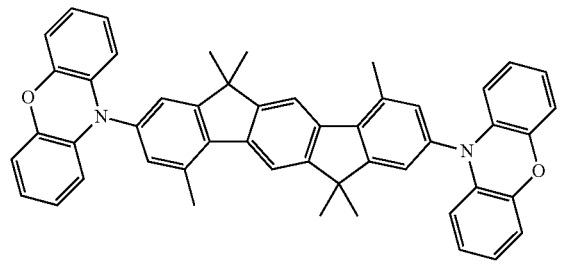
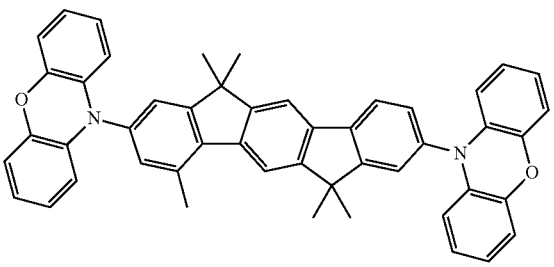
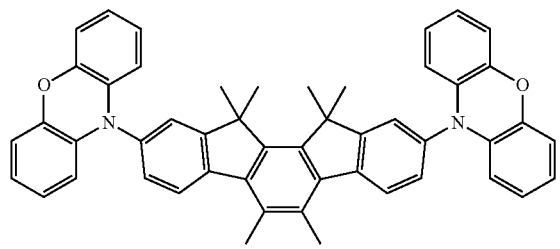
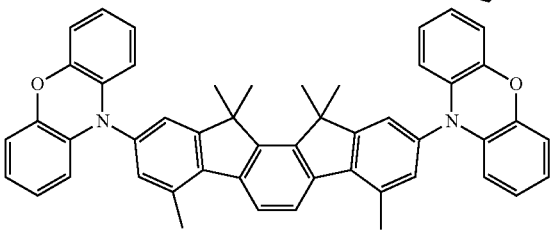

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S.

An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds, such as, for example, systems such as biphenyl, terphenyl or diphenyltriazine, are also taken to be aromatic or heteroaromatic ring systems in the sense of this invention.

An aromatic or heteroaromatic ring system having 5-60 aromatic ring atoms, which may also in each case be substituted by the above-mentioned radicals and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals R, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The group Ar in the compound of the formula (1) preferably represents an aryl group having 6 to 30 C atoms or a heteroaryl group having 5 to 30 aromatic ring atoms, which may be substituted by one or more radicals R. Ar particularly preferably represents an aryl group having 6 to 18 aromatic ring atoms, which may be substituted by one or more radicals R, or a heteroaryl group having 5 to 18 aromatic ring atoms, which may be substituted by one or more radicals R.

Ar very particularly preferably represents a heteroaryl group having 5 to 18 aromatic ring atoms, which may be substituted by one or more radicals R.

In a further preferred embodiment of the invention, Ar is not 1,3,5-triazine which is substituted by two phenyl groups. In a more preferred embodiment, Ar is not 1,3,5-triazine.

In a further preferred embodiment of the invention, Ar is not a heteroaryl group which is bonded to the radical of the compound of the formula (1) via a nitrogen atom which is part of a six-membered ring of the relevant heteroaryl group. In a more preferred embodiment, Ar is not a heteroaryl group which is bonded to the radical of the compound of the formula (1) via a nitrogen atom.

For the purposes of this invention, Ar is particularly preferably selected on each occurrence, identically or differently, from benzene, naphthalene, anthracene, phenanthrene, pyrene, dihydropyrene, chrysene, perylene, fluoranthene, benzanthracene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole, indenocarbazole, fluorene, indenofluorene, spirobifluorene and indolocarbazole, each of which is substituted by one or more radicals R, most preferably benzene, thiophene, triazine, pyridine, pyrimidine, pyrrole and benzimidazole, each of which is substituted by one or more radicals R.

In a further preferred embodiment of the invention, X in the compounds according to the invention is selected from —$C(R)_2$—, —NR—, —O— and —S—. X is particularly preferably selected from —$C(R)_2$— and —NR—.

It is furthermore preferred for a total of 0, 1 or 2 of the groups W, Z and Y to represent nitrogen and all others to represent C or $CR^1$ or $CR^2$, in accordance with the above-mentioned definition of W, Z and Y. Particularly preferably, none of the groups W, Z and Y represents nitrogen and all groups W, Z and Y represent C or $CR^1$ or $CR^2$, in accordance with the above-mentioned definition of W, Z and Y.

In a further preferred embodiment of the invention, the group W is equal to CH or N, particularly preferably equal to CH.

In another further preferred embodiment of the invention, the group Y, if it is not bonded to a group X, is equal to CH or N, particularly preferably equal to CH.

In a further preferred embodiment, the group Z, if it is not bonded to a bridge X, is equal to $CR^1$.

In compounds of the formula (1), the sum of m and n is furthermore preferably equal to 1.

In a further embodiment of the invention, it is preferred for the compound of the formula (1) to conform to one of the two formulae (1a) or (1b)

formula (1a)

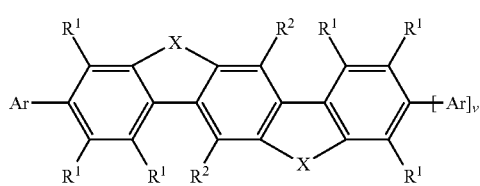

formula (1b)

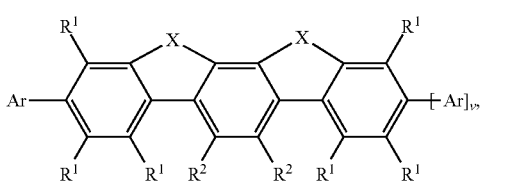

where the symbols and indices occurring have the meaning indicated above and furthermore at least one group $R^1$ must be present which represents a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, each of which may be substituted by one or more radicals $R^3$, where one or more $CH_2$ groups may be replaced by —$R^3C$=$CR^3$—, —C≡C—, —Si($R^3$)$_2$—, —Ge($R^3$)$_2$—, —Sn($R^3$)$_2$—, C=O, C=S, C=Se, C=N$R^3$, P(=O)($R^3$), S=O, S(=O)$_2$, —N$R^3$—, —O—, —S— or —C(=O)N$R^3$— and where one or more H atoms may be replaced by D, F, Cl, Br, I, CN or $NO_2$, or an aromatic or heteroaromatic ring system having 5 to 30 aromatic ring atoms, which may in each case be substituted by one or more radicals $R^3$.

In a particularly preferred embodiment of the invention, the compounds according to the invention conform to one of the formulae (2), (3), (4), (5), (6) or (7)

formula (2)

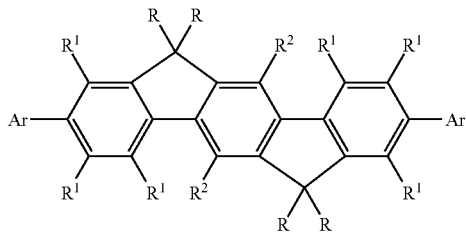

formula (3)

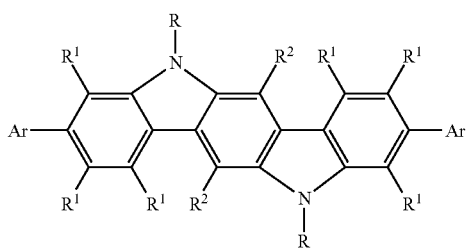

formula (4)

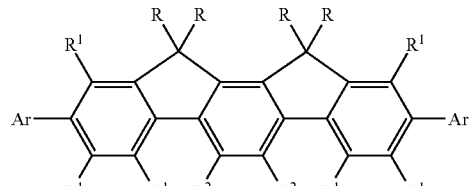

formula (5)

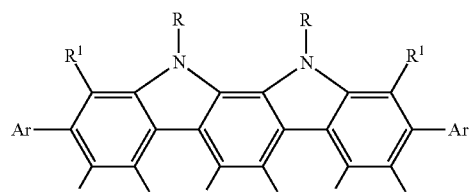

formula (6)

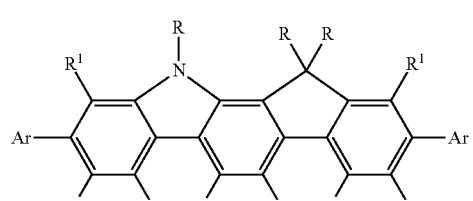

formula (7)

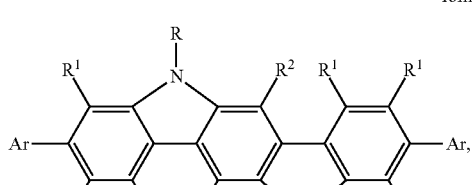

where the symbols occurring have the meaning indicated above and furthermore at least one group $R^1$ must be present which represents a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, each of which may be substituted by one or more radicals $R^3$, where one or more $CH_2$ groups may be replaced by —$R^3C$=$CR^3$—, —C≡C—, —Si($R^3$)$_2$—, —Ge($R^3$)$_2$—, —Sn($R^3$)$_2$—, C=O, C=S, C=Se, C=N$R^3$, P(=O)($R^3$), S=O, S(=O)$_2$, —N$R^3$—, —O—, —S— or —C(=O)N$R^3$— and where one or more H atoms may be replaced by D, F, Cl, Br, I, CN or $NO_2$, or an aromatic or heteroaromatic ring system having 5 to aromatic ring atoms, which may in each case be substituted by one or more radicals $R^3$.

For radicals R which are bonded to a group Ar, it is preferred in accordance with the invention for R to be selected on each occurrence, independently of one another, from H, D, F, CN, Si($R^3$)$_3$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more $CH_2$ groups may be replaced by —C≡C—, —$R^3C$=$CR^3$—, —Si($R^3$)$_2$—, C=O, C=N$R^3$, —N$R^3$—, —O—, —S—, —C(=O)O— or —C(=O)N$R^3$—, or an aryl or heteroaryl group having 5 to 30 aromatic ring atoms, which may in each case be substituted by one or more radicals R³.

For radicals R which are part of a group X in the embodiment —C(R)₂—, it is preferred in accordance with the invention for R to be selected on each occurrence, independently of one another, from a straight-chain alkyl or alkoxy group having 1 to 20 C atoms or a branched or cyclic alkyl or alkoxy group having 3 to 20 C atoms, each of which may be substituted by one or more radicals R³, where one or more CH₂ groups may be replaced by —C≡C—, —R³C═CR³—, —Si(R³)₂—, C═O, C═NR³, —NR³—, —O—, —S—, —C(═O)O— or —C(═O)NR³—, or an aryl or heteroaryl group having 5 to 30 aromatic ring atoms, which may in each case be substituted by one or more radicals R³.

For radicals R which are part of a group X in the embodiment —NR—, it is preferred in accordance with the invention for R to be selected on each occurrence, independently of one another, from an aryl or heteroaryl group having 5 to 30 aromatic ring atoms, which may in each case be substituted by one or more radicals R³.

In a further embodiment of the invention, it is preferred for R¹ to be selected on each occurrence, independently of one another, from H, D, F, CN, Si(R³)₃ or a straight-chain alkyl or alkoxy group having 1 to 20 C atoms or a branched or cyclic alkyl or alkoxy group having 3 to 20 C atoms, each of which may be substituted by one or more radicals R³, where one or more CH₂ groups may be replaced by —C≡C—, —R³C═CR³—, —Si(R³)₂—, C═O, C═NR³, —NR³—, —O—, —S—, —C(═O)O— or —C(═O)NR³—, or an aryl or heteroaryl group having 5 to 30 aromatic ring atoms, which may in each case be substituted by one or more radicals R³.

R¹ is particularly preferred selected on each occurrence, independently of one another, from H, a straight-chain alkyl or alkoxy group having 1 to 10 C atoms or a branched or cyclic alkyl or alkoxy group having 3 to 10 C atoms, and is very particularly preferably selected from H and a straight-chain alkyl group having 1 to 8 C atoms.

At least one group R¹ in the compounds according to the invention is preferably selected from a straight-chain alkyl or alkoxy group having 1 to 20 C atoms or a branched or cyclic alkyl or alkoxy group having 3 to 20 C atoms, each of which may be substituted by one or more radicals R³, where one or more CH₂ groups may be replaced by —C≡C—, —R³C═CR³—, —Si(R³)₂—, C═O, C═NR³, —NR³—, —O—, —S—, —C(═O)O— or —C(═O)NR³—, or an aryl or heteroaryl group having 5 to 30 aromatic ring atoms, which may in each case be substituted by one or more radicals R³.

At least one group R¹ in the compounds according to the invention is particularly preferably selected from a straight-chain alkyl or alkoxy group having 1 to 10 C atoms or a branched or cyclic alkyl or alkoxy group having 3 to 10 C atoms, very particularly preferably from a straight-chain alkyl group having 1 to 8 C atoms.

In a further embodiment of the invention, it is preferred for R² to be selected on each occurrence, independently of one another, from H, D, F, CN, Si(R³)₃ or a straight-chain alkyl or alkoxy group having 1 to 20 C atoms or a branched or cyclic alkyl or alkoxy group having 3 to 20 C atoms, each of which may be substituted by one or more radicals R³, where one or more CH₂ groups may be replaced by —C≡C—, —R³C═CR³—, —Si(R³)₂—, C═O, C═NR³, —NR³—, —O—, —S—, —C(═O)O— or —C(═O)NR³—, or an aryl or heteroaryl group having 5 to 30 aromatic ring atoms, which may in each case be substituted by one or more radicals R³.

In a particularly preferred embodiment of the invention, the compounds according to the invention conform to one of the formulae (2a), (3a), (4a), (5a), (6a) or (7a)

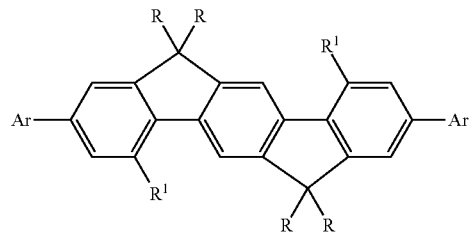

formula (2a)

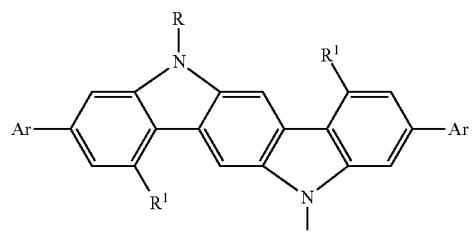

formula (3a)

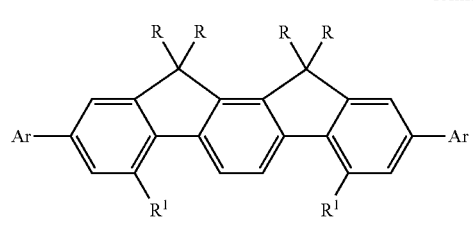

formula (4a)

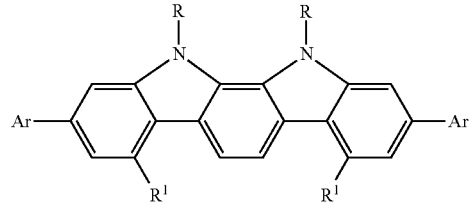

formula (5a)

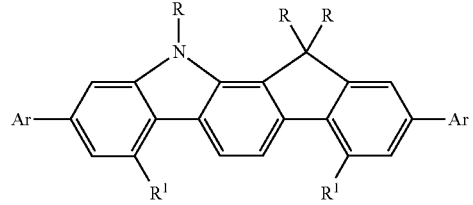

formula (6a)

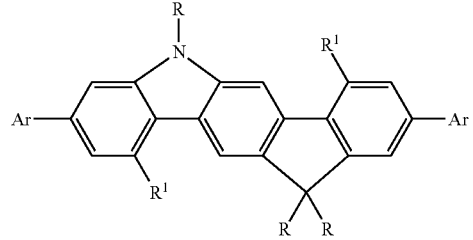

formula (7a)

where the symbols occurring have the meaning indicated above and furthermore at least one group R¹ must be present which represents a straight-chain alkyl or alkoxy group having 1 to 20 C atoms or a branched or cyclic alkyl or alkoxy group having 3 to 20 C atoms, each of which may be substituted by one or more radicals R³, where one or more CH₂ groups may be replaced by —C≡C—, —R³C=CR³—, —Si(R³)₂—, C=O, C=NR³, —NR³—, —O—, —S—, —C(=O)O— or —C(=O)NR³—, or an aryl or heteroaryl group having 5 to 30 aromatic ring atoms, which may in each case be substituted by one or more radicals R³.

Furthermore, the preferred and particularly preferred embodiments indicated above for the groups R and R¹ apply, in particular, to compounds (2a) to (7a).

Examples of compounds of the formula (1) are the structures depicted below.

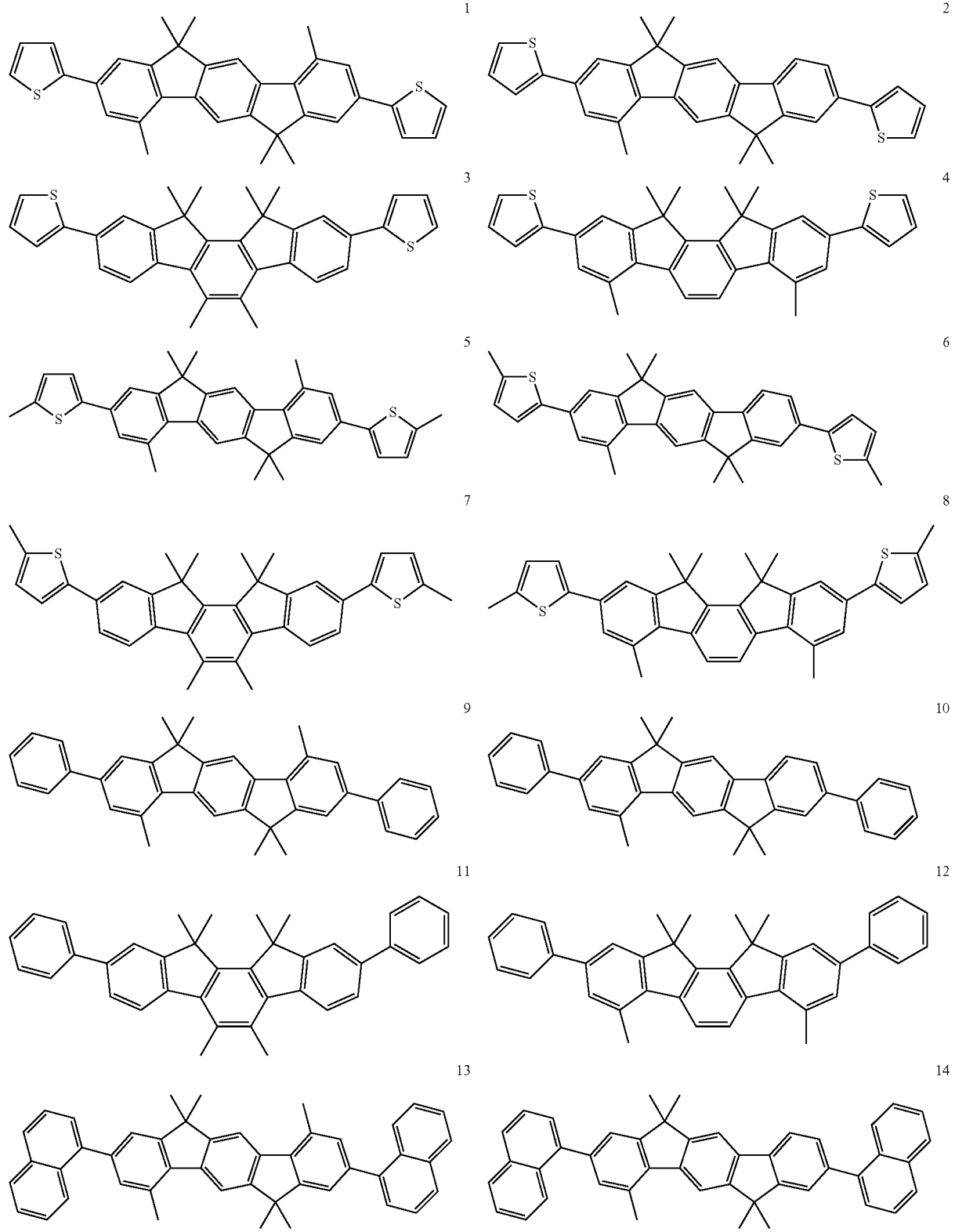

-continued
15
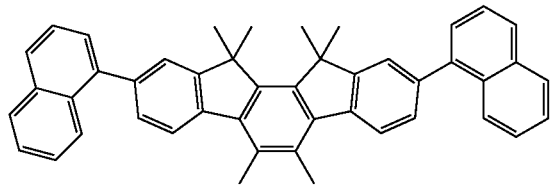
16
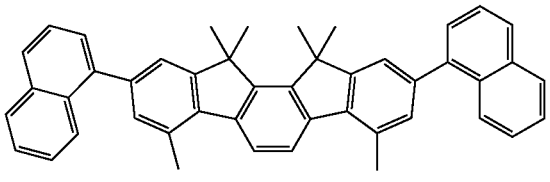
17
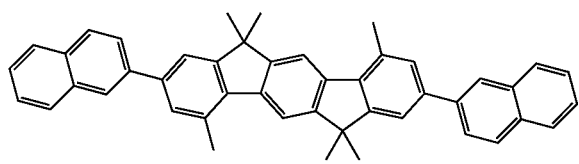
18
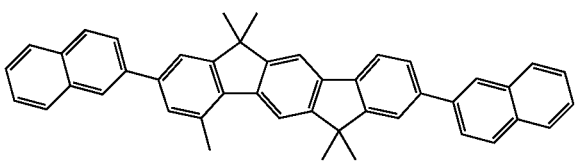
19
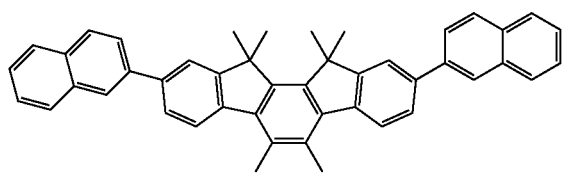
20
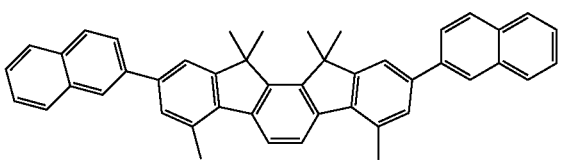
21
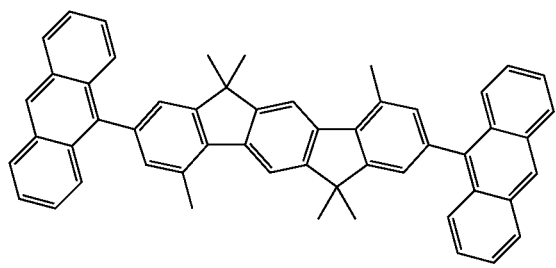
22
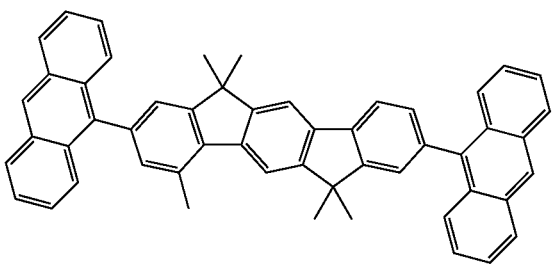
23
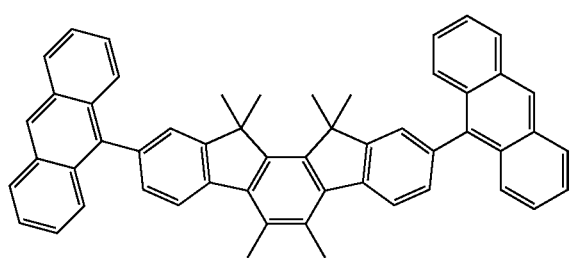
24
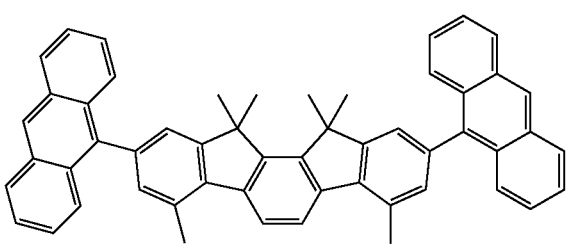
25
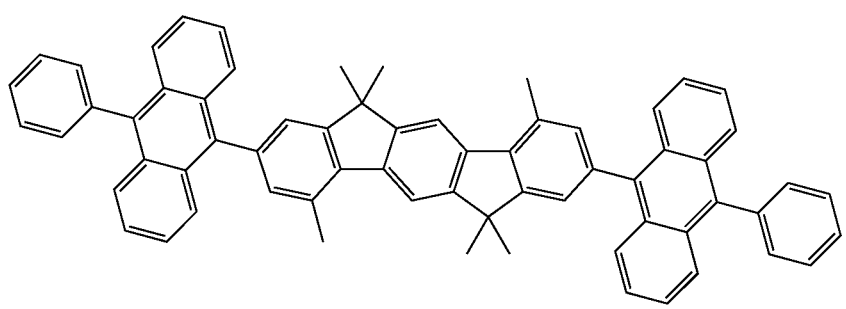

26
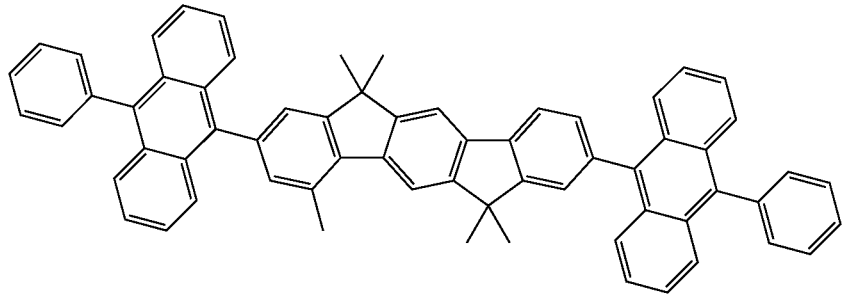
27
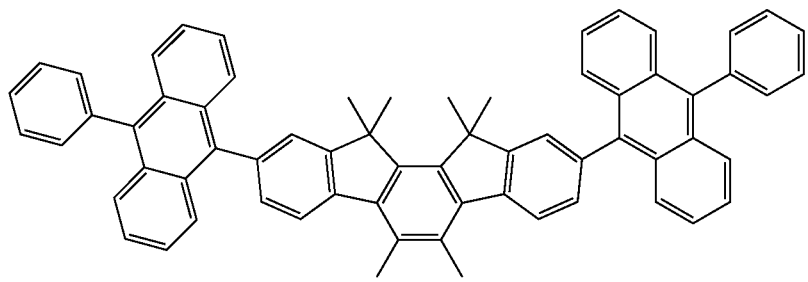
28
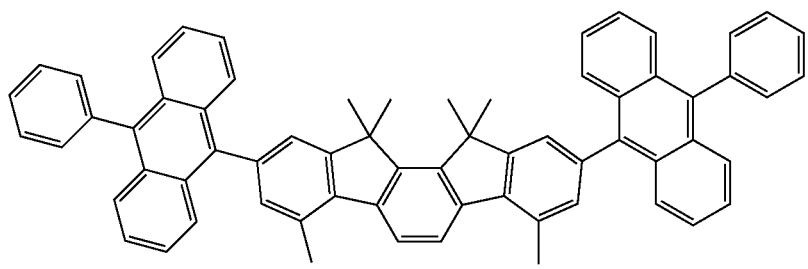
29
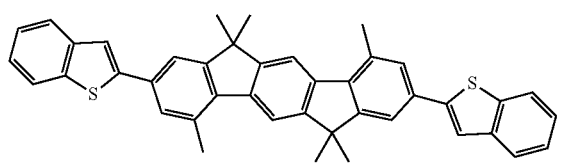
30
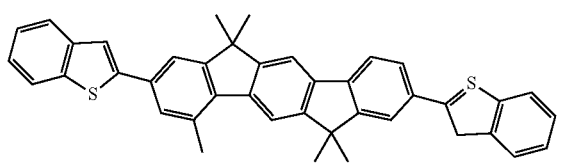
31
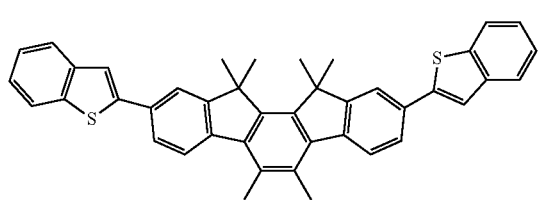
32
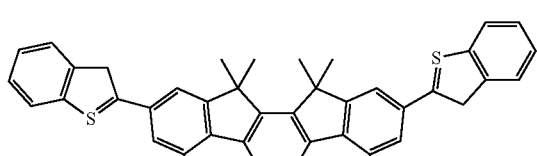
33
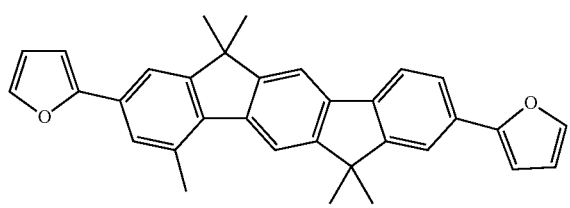
34
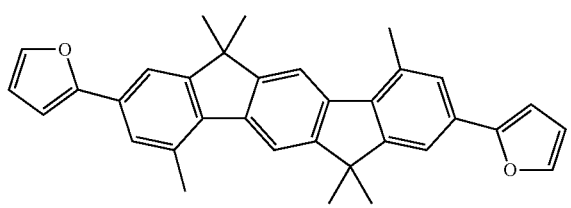

-continued
| 35 | 36 |
|---|---|
| 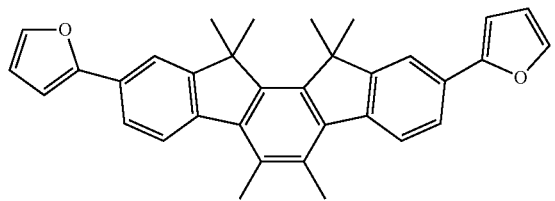 | 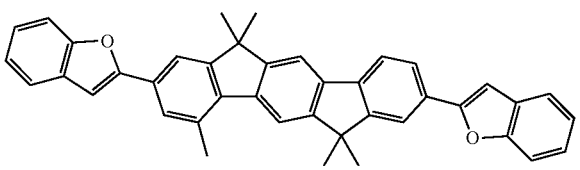 |
| 37 | 38 |
| 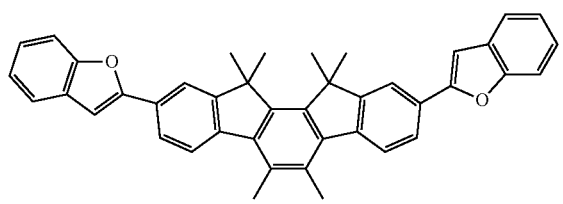 | 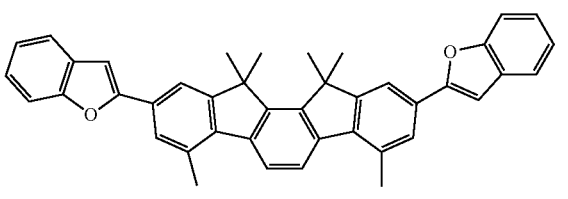 |
| 39 | 40 |
| | 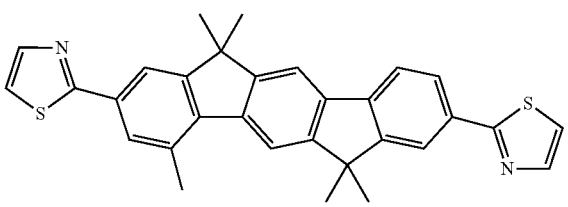 |
| 41 | 42 |
| 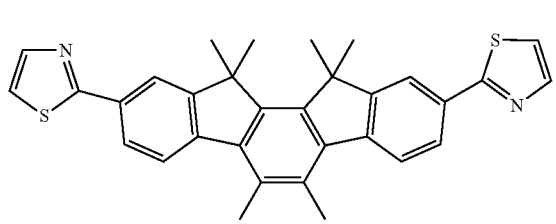 | 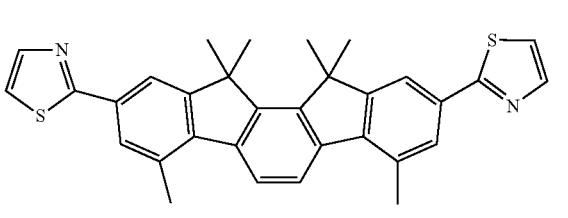 |
| 43 | 44 |
| 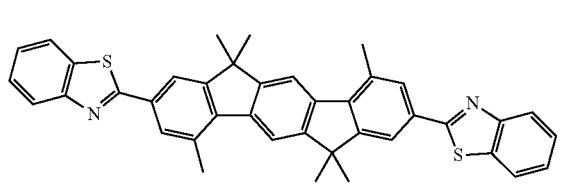 | 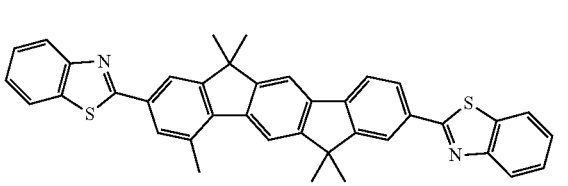 |
| 45 | 46 |
| 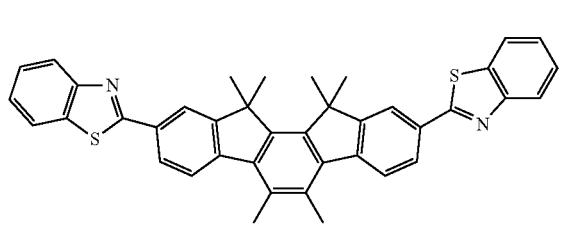 | 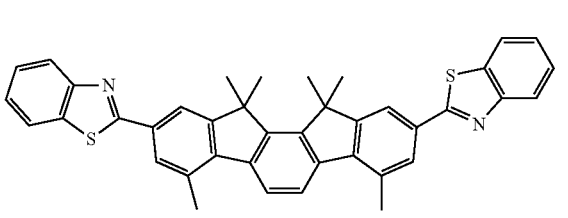 |

-continued
49
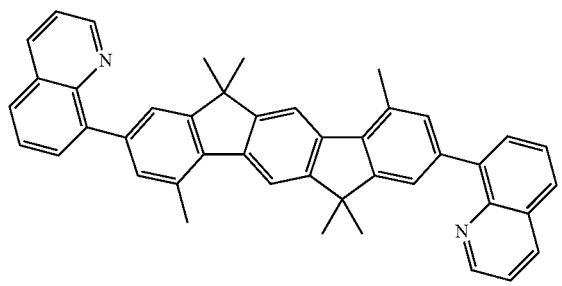
50
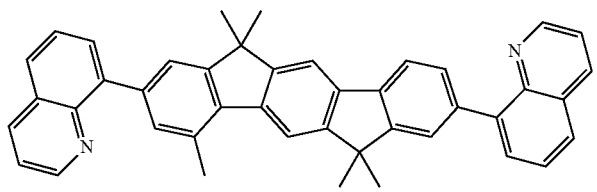
51
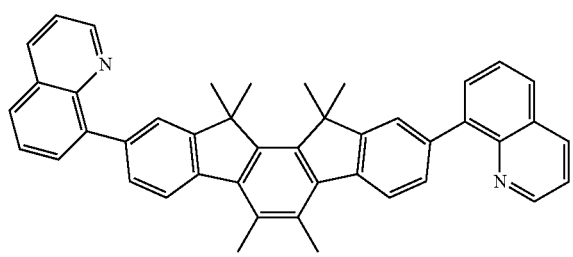
52
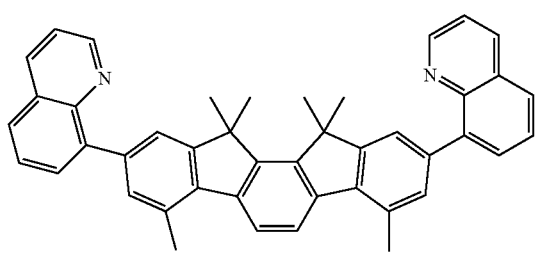
53
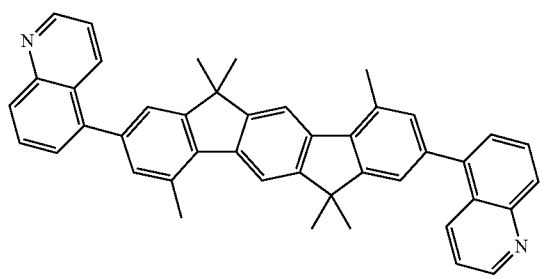
54
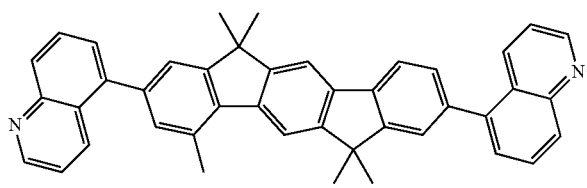
55
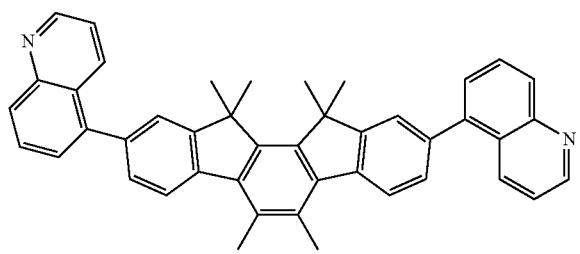
56
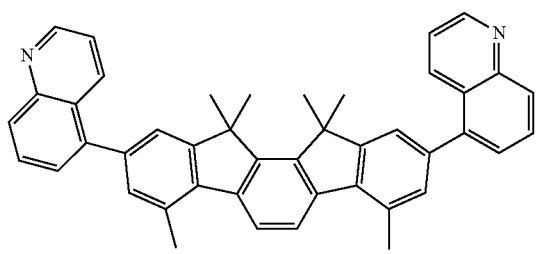
57
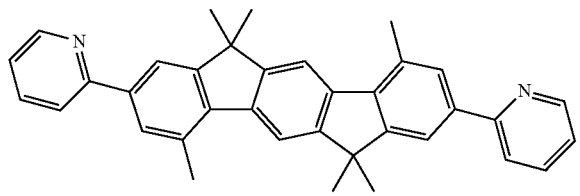
58
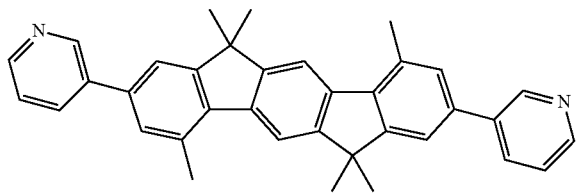
59
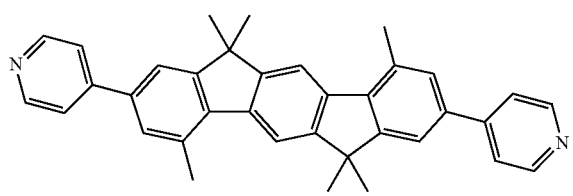
60
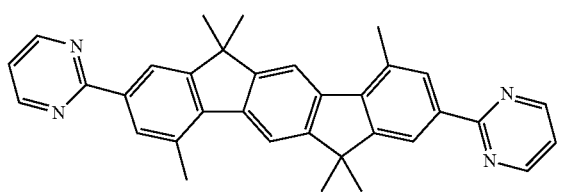

-continued
61
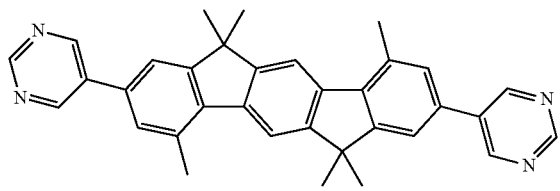
62
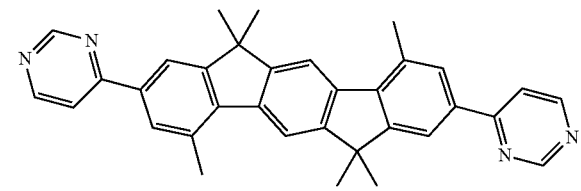
63
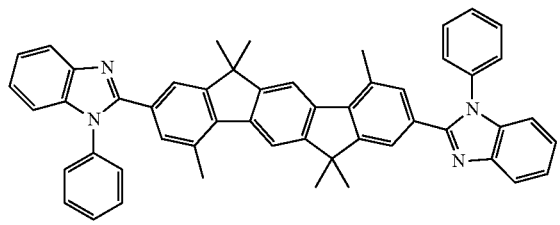
64
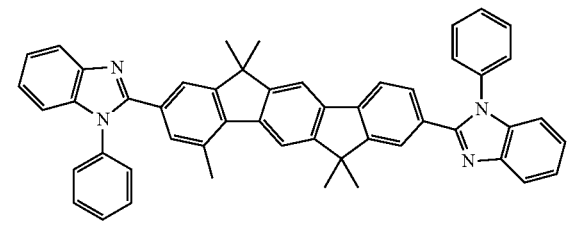
65
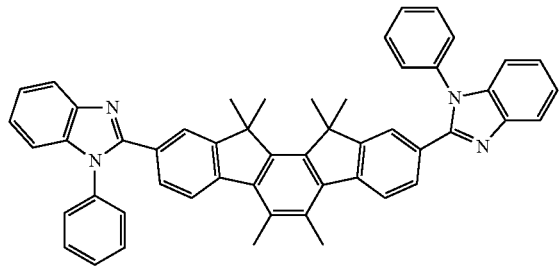
66
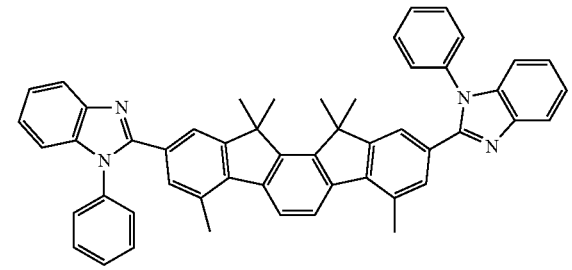
67
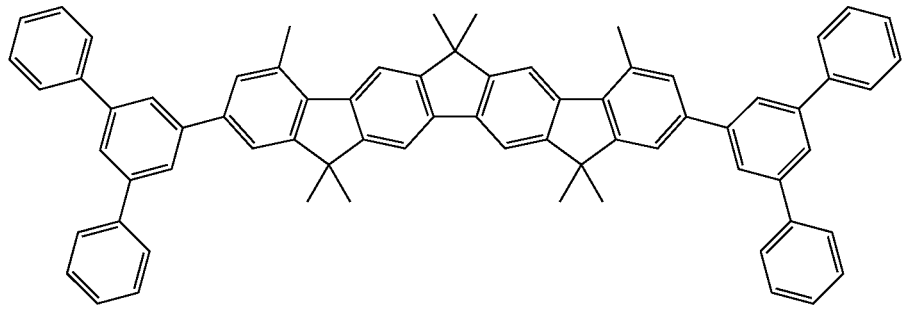
68
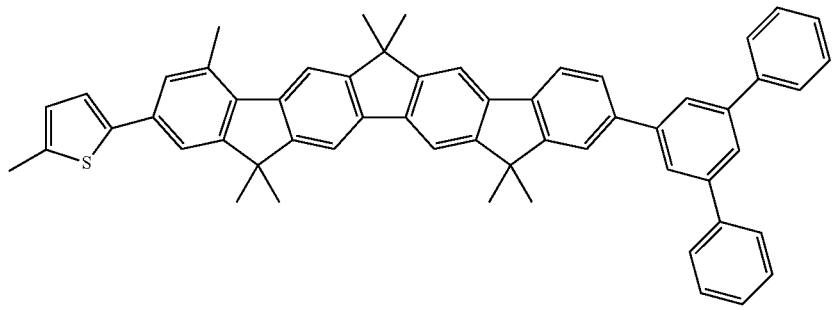

69
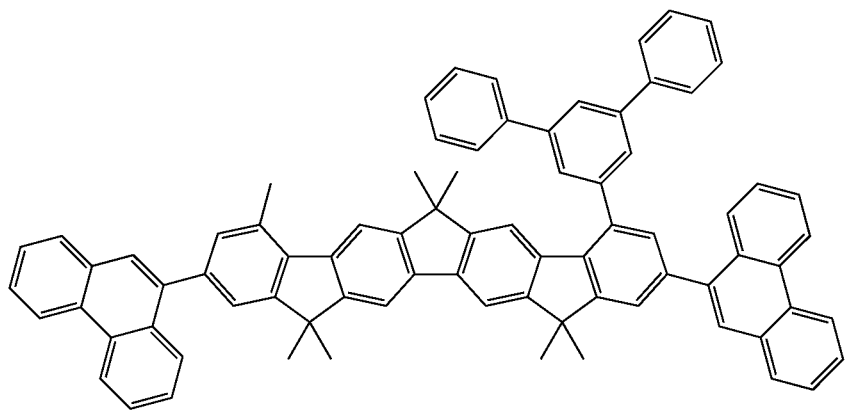
70
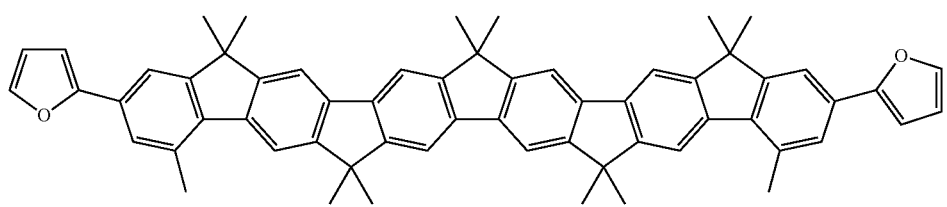
71
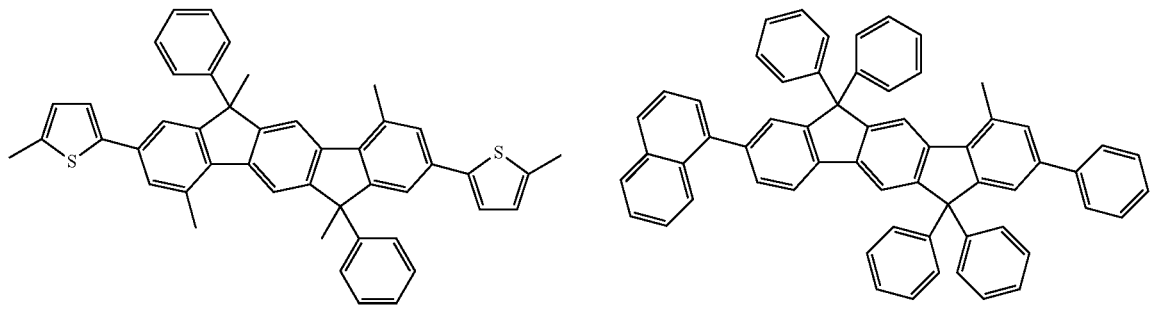
72
73
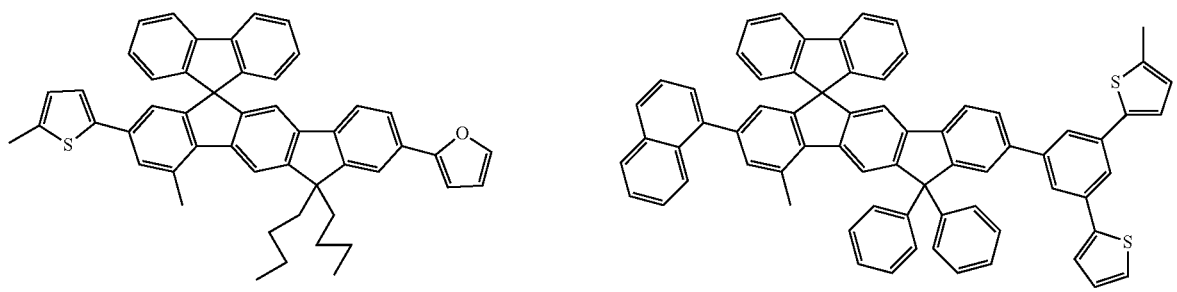
74
75
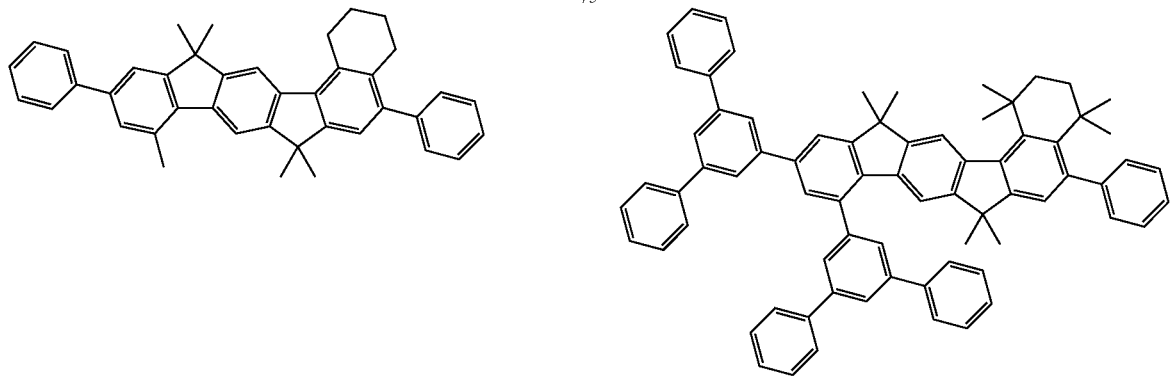
76

-continued
77
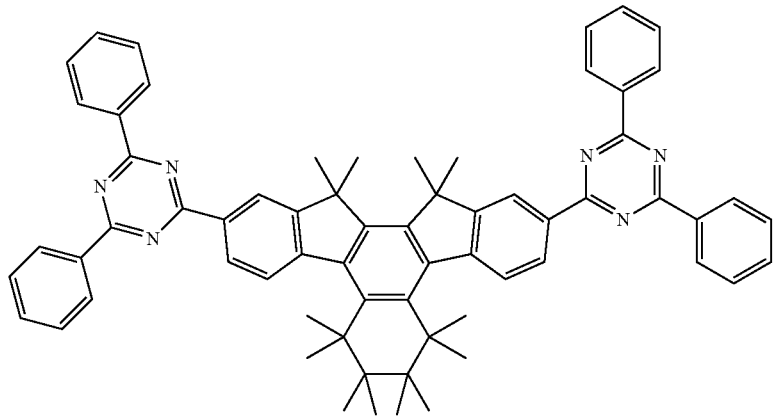
78
79
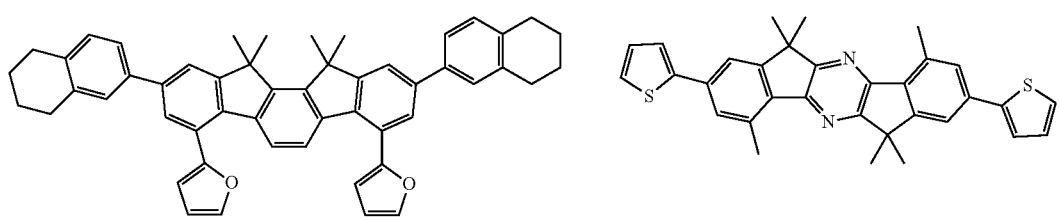
80
81
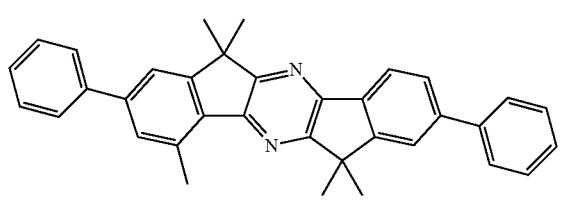
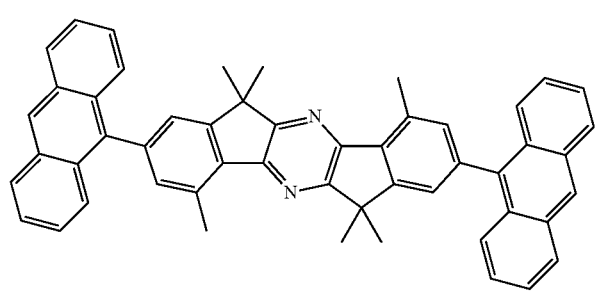
82
83
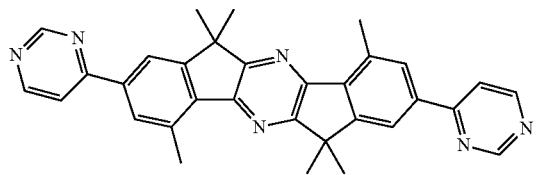
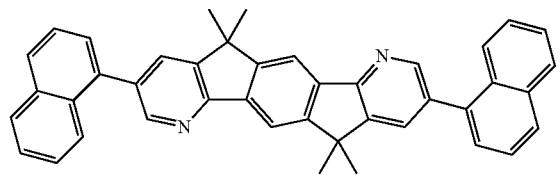
84
85
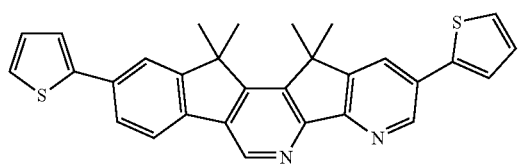
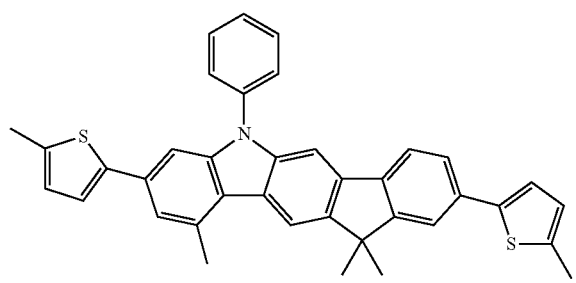

-continued
86
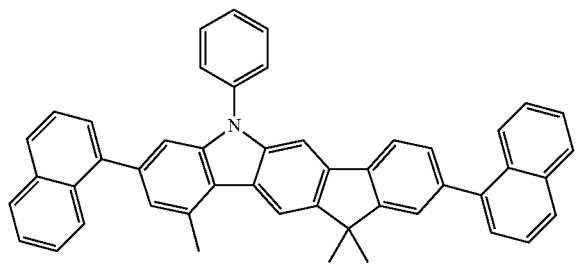
87
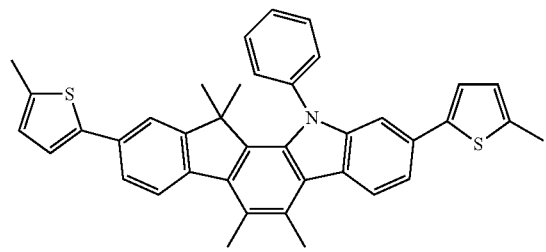
88
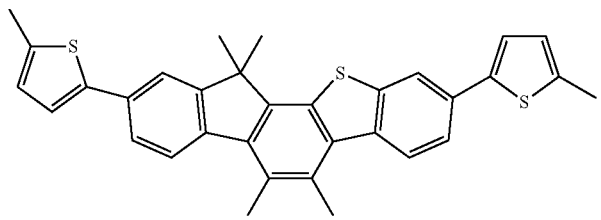
89
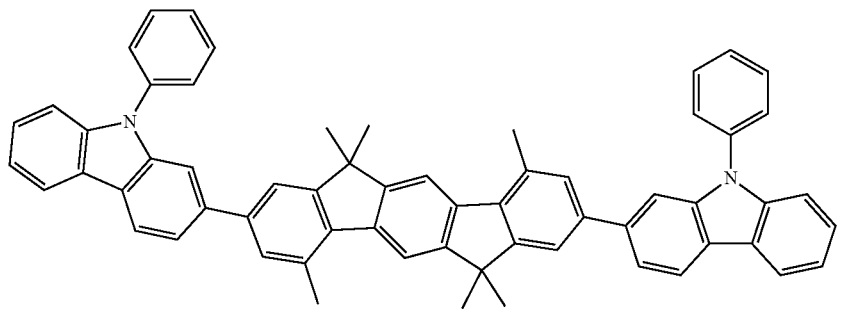
90
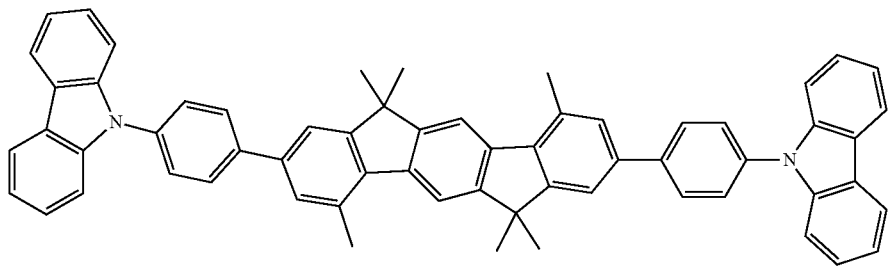
91
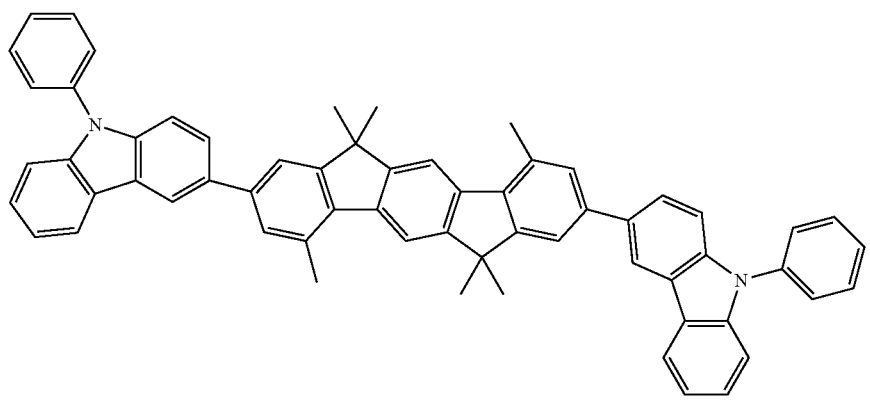

92
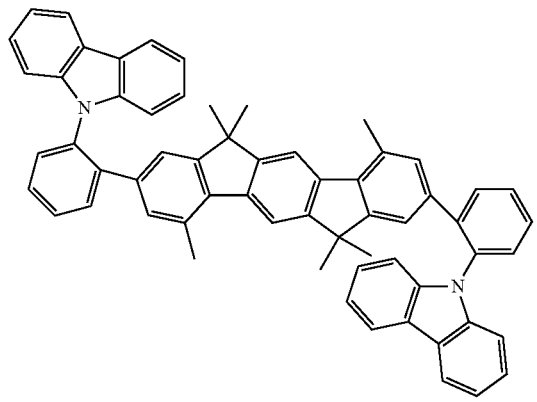
93
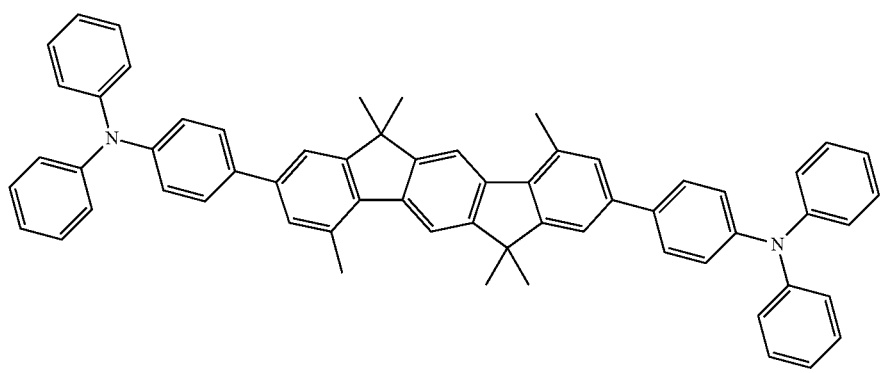
94
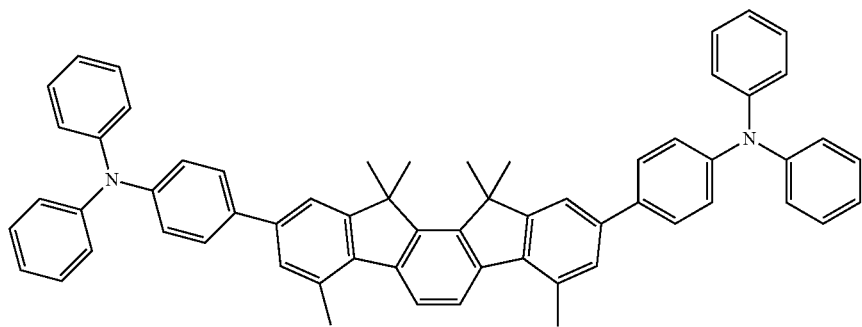
95
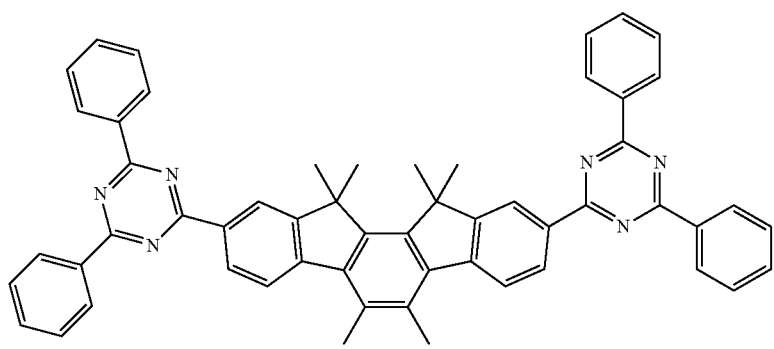

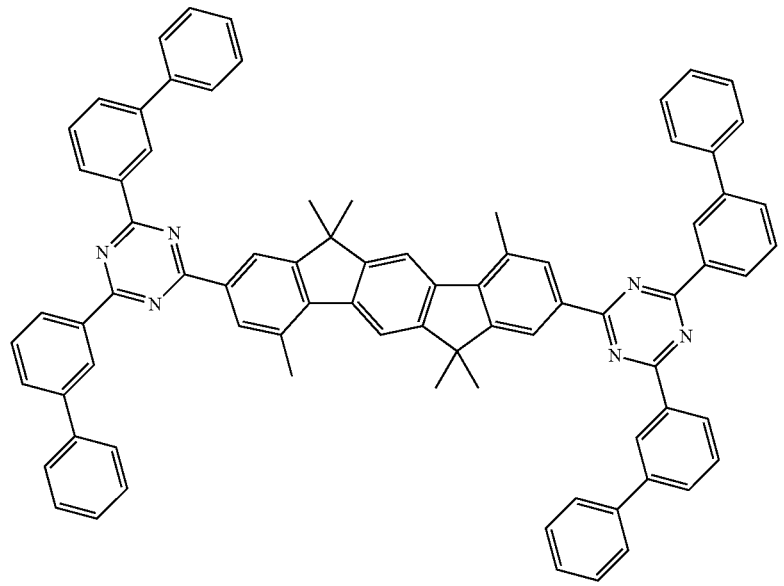
96
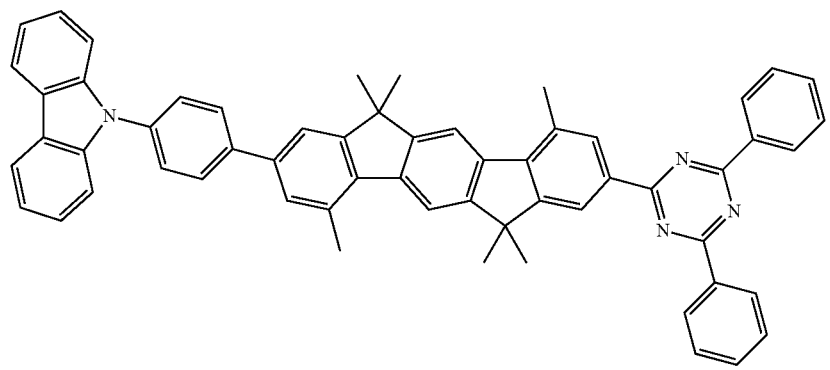
97
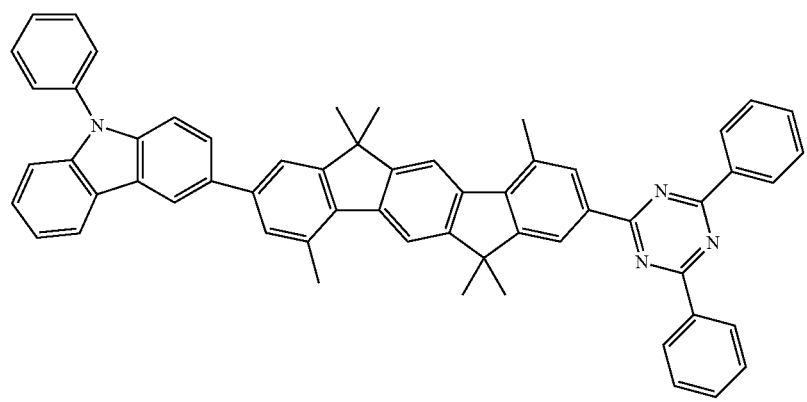
98

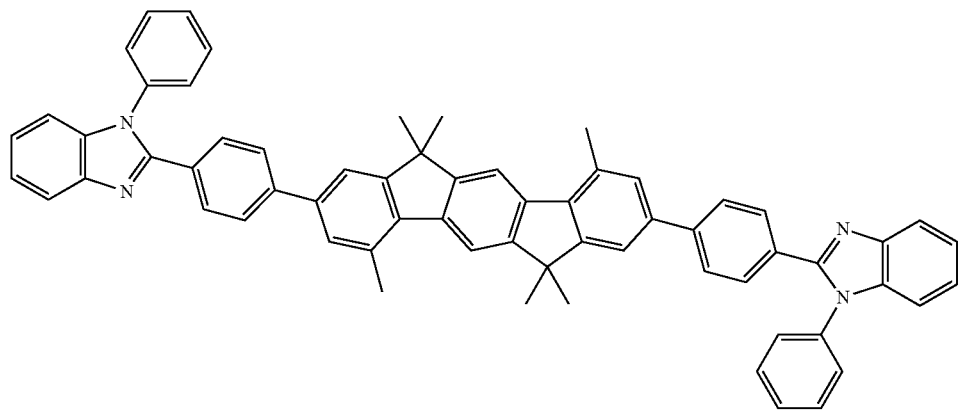
99
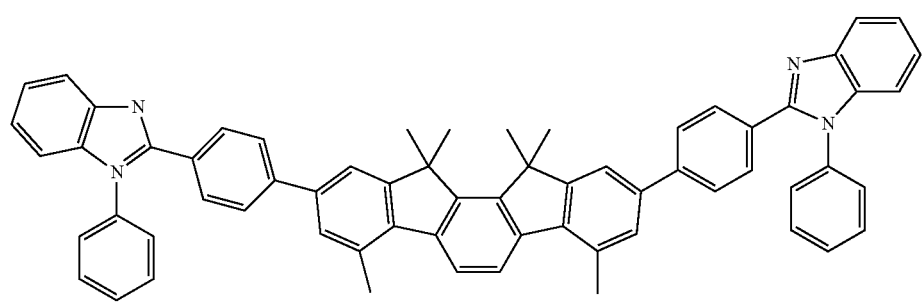
100
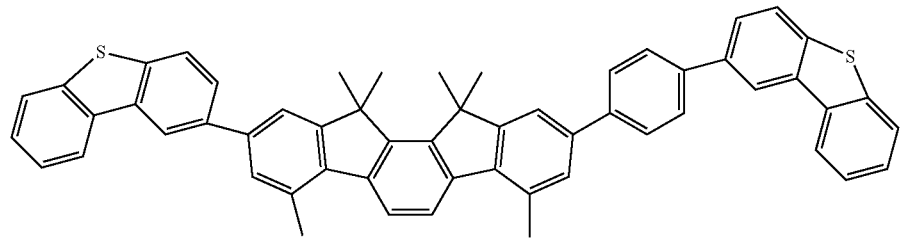
101
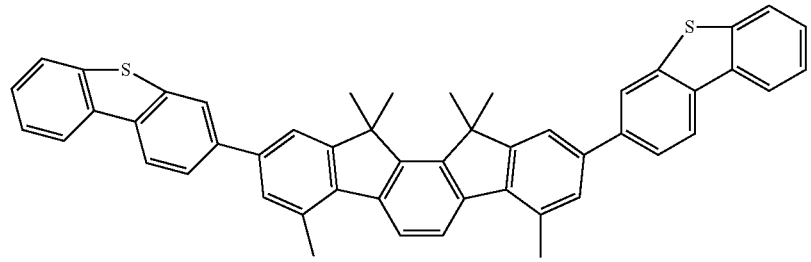
102
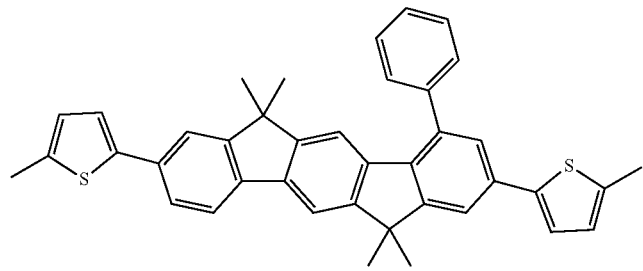
103

-continued
104
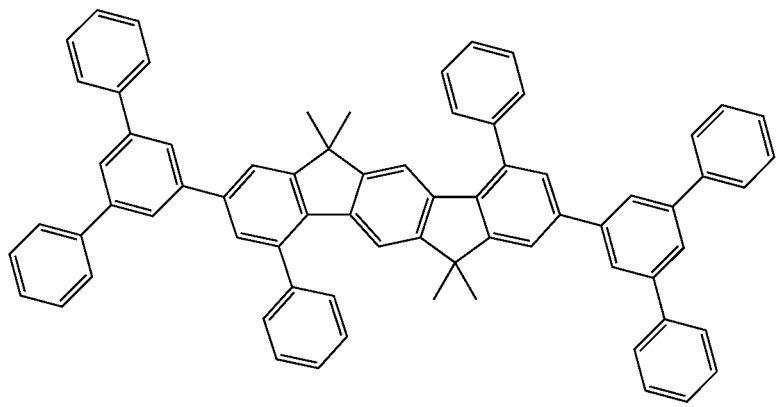
105
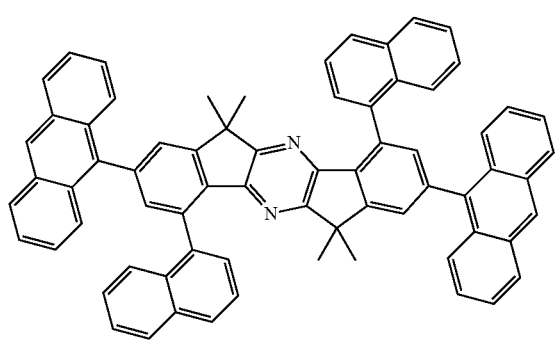
106
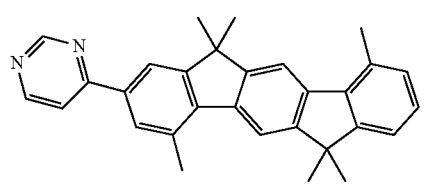
107
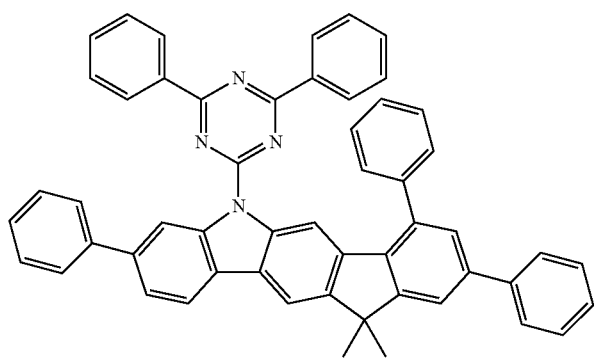
108
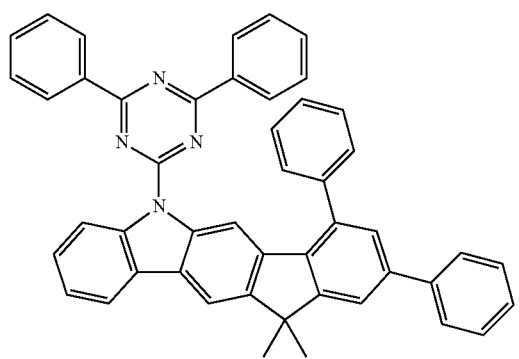
109
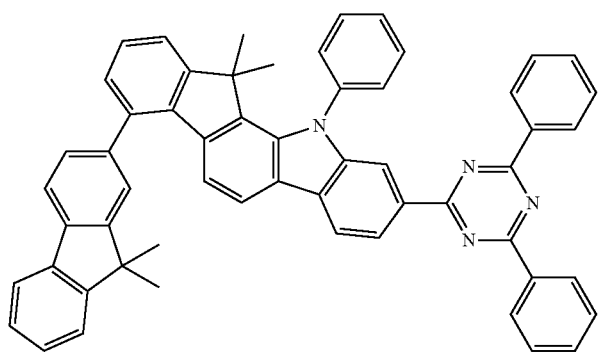
110
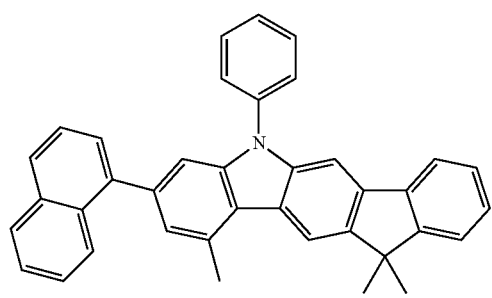

-continued
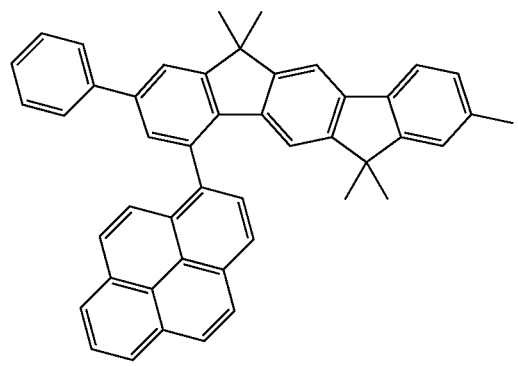
111
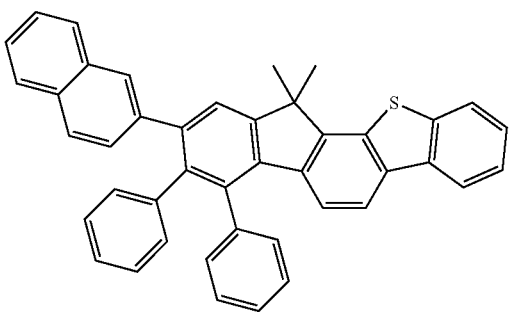
112
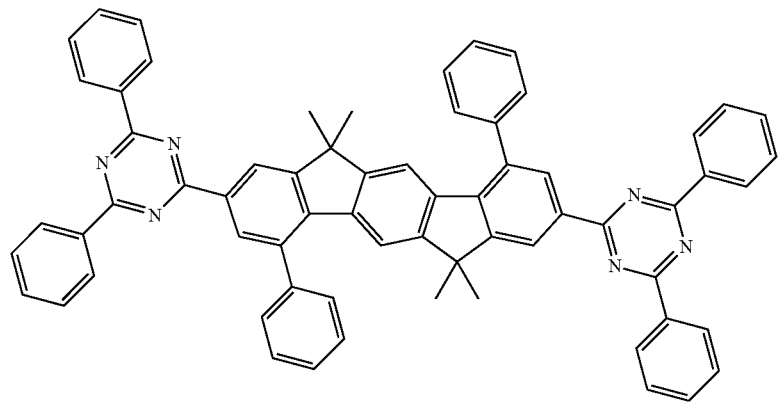
113
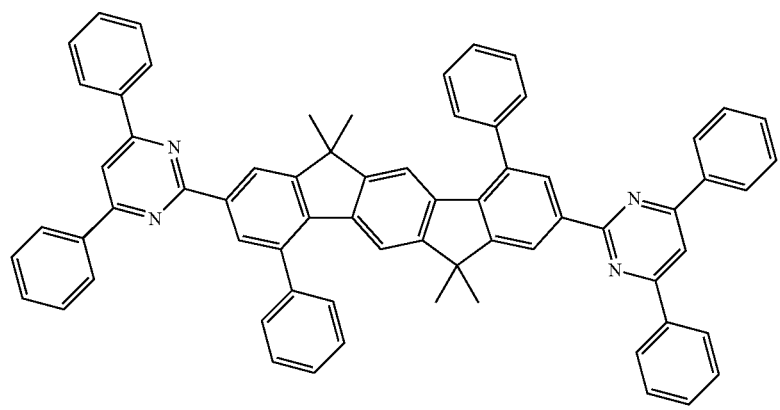
114
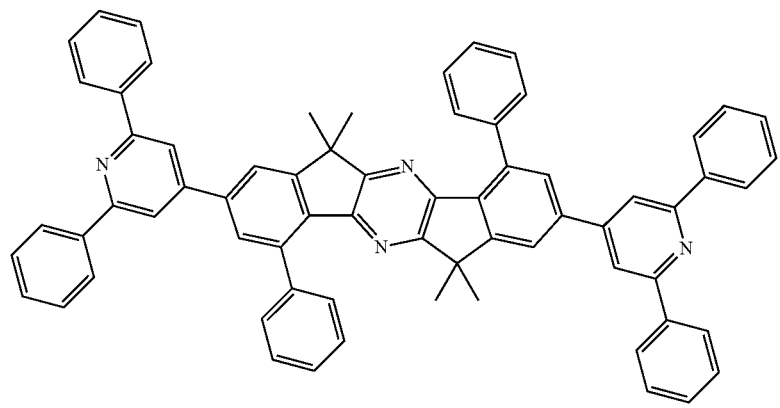
115

-continued
116
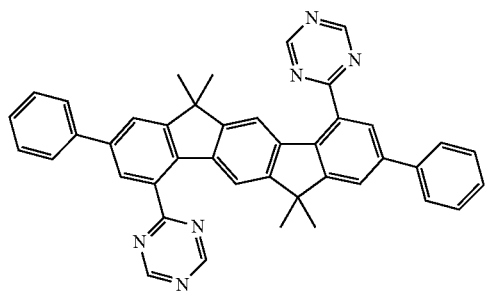
117
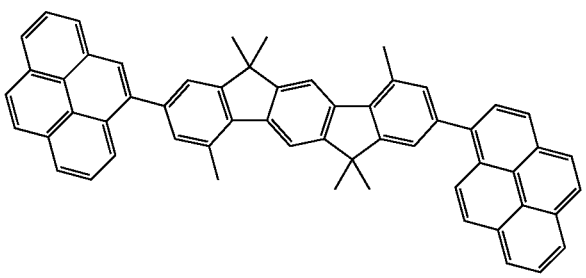
118
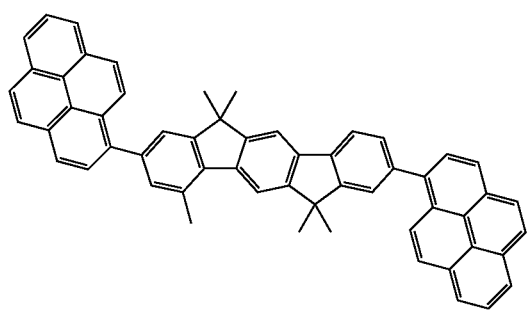
119
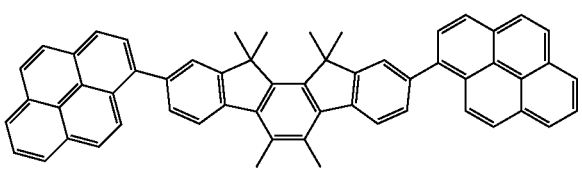
120
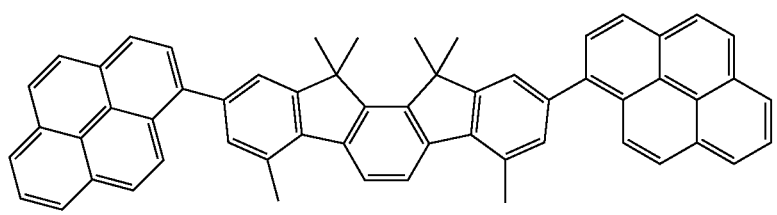
121
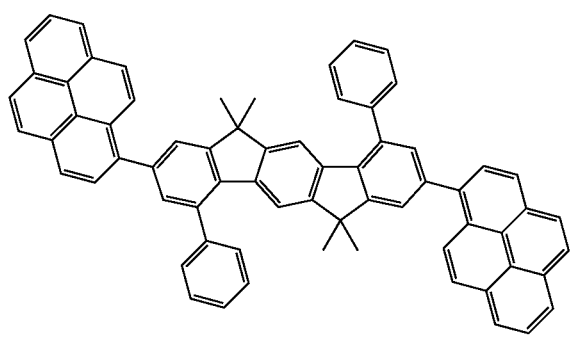
122
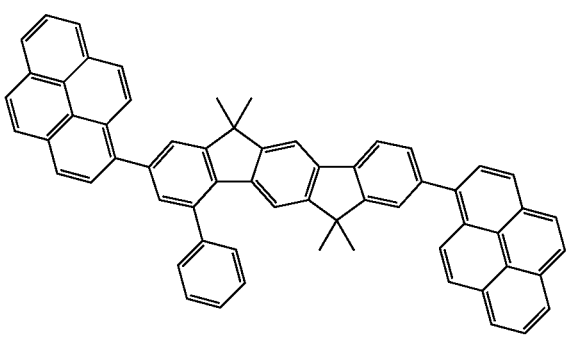
123
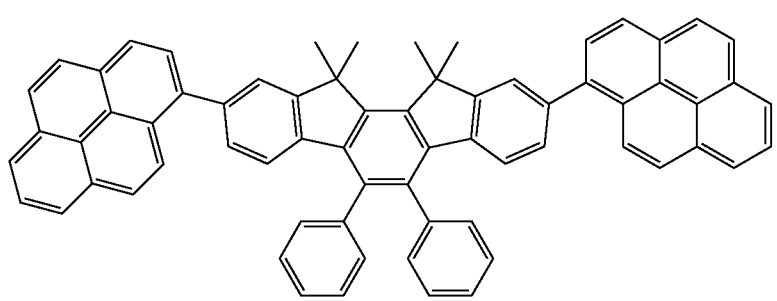

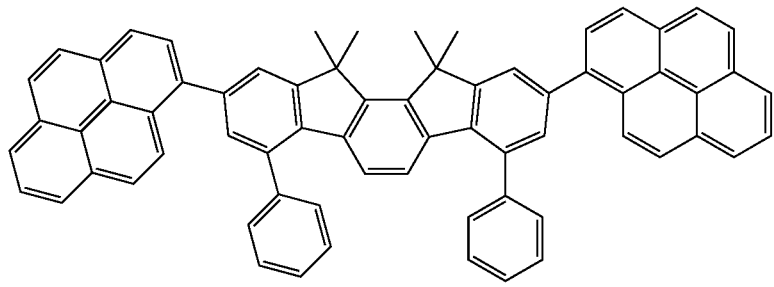

124

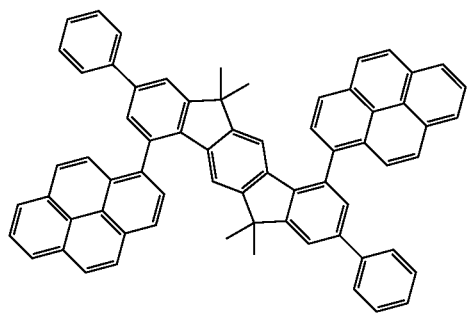

125

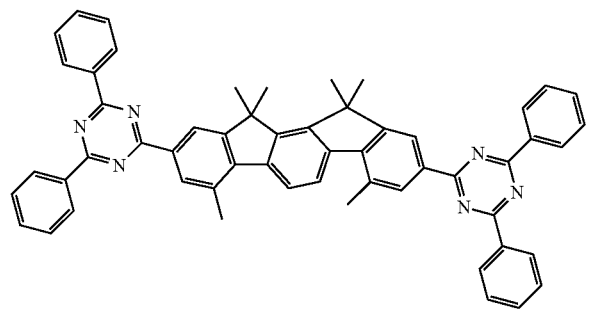

126

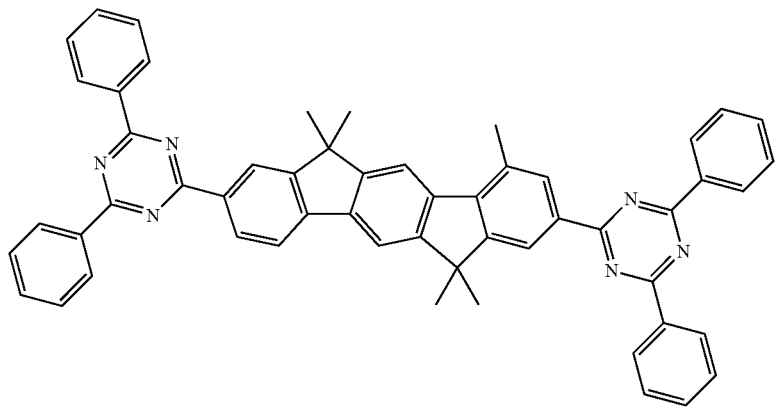

127

The compounds according to the invention can be prepared by synthetic steps known to the person skilled in the art, such as, for example, bromination, Suzuki coupling, Hartwig-Buchwald coupling, etc.

The present invention thus furthermore relates to a process for the preparation of the compounds according to the invention, comprising the reaction steps of:

a) synthesis of a derivative of a compound of the formula (1) which carries hydrogen instead of the groups Ar in these positions;

b) halogenation, giving a derivative of a compound of the formula (1) which is substituted by halogen instead of the groups Ar in these positions; and c) reaction of the compound from b) with a compound of the formula Ar—B(OR)$_2$, where Ar is as defined in formula (1) and the group B(OR)$_2$ represents a boronic acid derivative, in an organometallic coupling reaction.

Step a), the synthesis of the skeleton, can proceed, for example, as shown in the following scheme:

Scheme 1

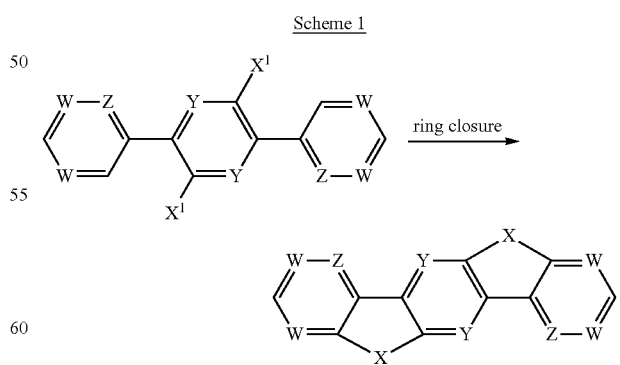

The bridges X are introduced here between the aromatic rings (cf. formula (1)) by a ring-closure reaction. The parent structure shown containing three aromatic six-membered rings can be prepared by an organometallic coupling from three different aryl building blocks, for example by a Suzuki, Stille, Hartwig-Buchwald, Heck, Negishi, Sonogashira or Kumada reaction, preferably by a Suzuki reaction, as shown in Scheme 2 below.

In a preferred embodiment of the compounds according to the invention, a C(R)$_2$ group is present as bridging unit X, which is formed by the action of acid on a tertiary, benzylic alcohol (cf. synthesis in Scheme 2). This in turn can be obtained starting from a carboxylic acid ester group by reaction with an organometallic reagent, such as, for example, MeMgCl or MeLi. In a further preferred variant, the bridging group X present is a sulfur atom. This bridging sulfur unit can, as disclosed in the application WO 2010/083873, be obtained by reaction of an aryl sulfoxide with an acid. In a further preferred embodiment, the bridging group X is a group NR. This can, as likewise explicitly disclosed in the above-mentioned application WO 2010/083873, be obtained by reduction of an arylnitro group using a phosphite, for example triethyl phosphite, and subsequent ring-closure reaction. This may be followed by a reaction with, for example, an alkylating agent in order to introduce the substituent R onto the group NR.

In step b), a halogenation reaction, preferably an iodination or bromination, particularly preferably a bromination, is carried out. To this end, a halogen atom is in each case introduced onto the outer rings in the positions para to the bonds to the central aryl group.

The synthesis of the compounds according to the invention including a halogenation reaction (step b)) represents one of the possible synthetic routes; the person skilled in the art will be able, as part of his general expert knowledge, to fall back on other synthetic routes in order to prepare the compounds according to the invention. For example, the relevant positions on the outer rings may also be substituted by other reactive functional groups, such as, for example, tosylate or triflate groups. These groups may already be introduced in advance through suitably functionalised aryl building blocks. These may be identical or different, enabling two different groups Ar to be introduced sequentially. It is also possible for only one reactive group to be present, giving compounds according to the invention containing only one group Ar. However, preference is given for the purposes of the present invention to the introduction of two identical groups Ar, particularly preferably through the steps b) and c) described.

In step c), the compound according to the invention is finally prepared via an organometallic coupling reaction, preferably a Suzuki coupling to a boronic acid compound of the formula Ar—B(OR)$_2$. Substitution by different halogen substituents also enables, as already mentioned in connection with step b), two different groups Ar to be introduced. The groups Ar can also be introduced by a route other than by an organometallic coupling reaction. An example thereof is the synthesis presented in Scheme 2.

It should again be mentioned that the person skilled in the art is not tied to the processes shown for the synthesis of the compounds according to the invention. He can, without being inventive, also prepare the compounds according to the invention by alternative routes.

Scheme 2 below shows an explicit example of the synthesis of a compound according to the invention by the process described above.

Scheme 2:

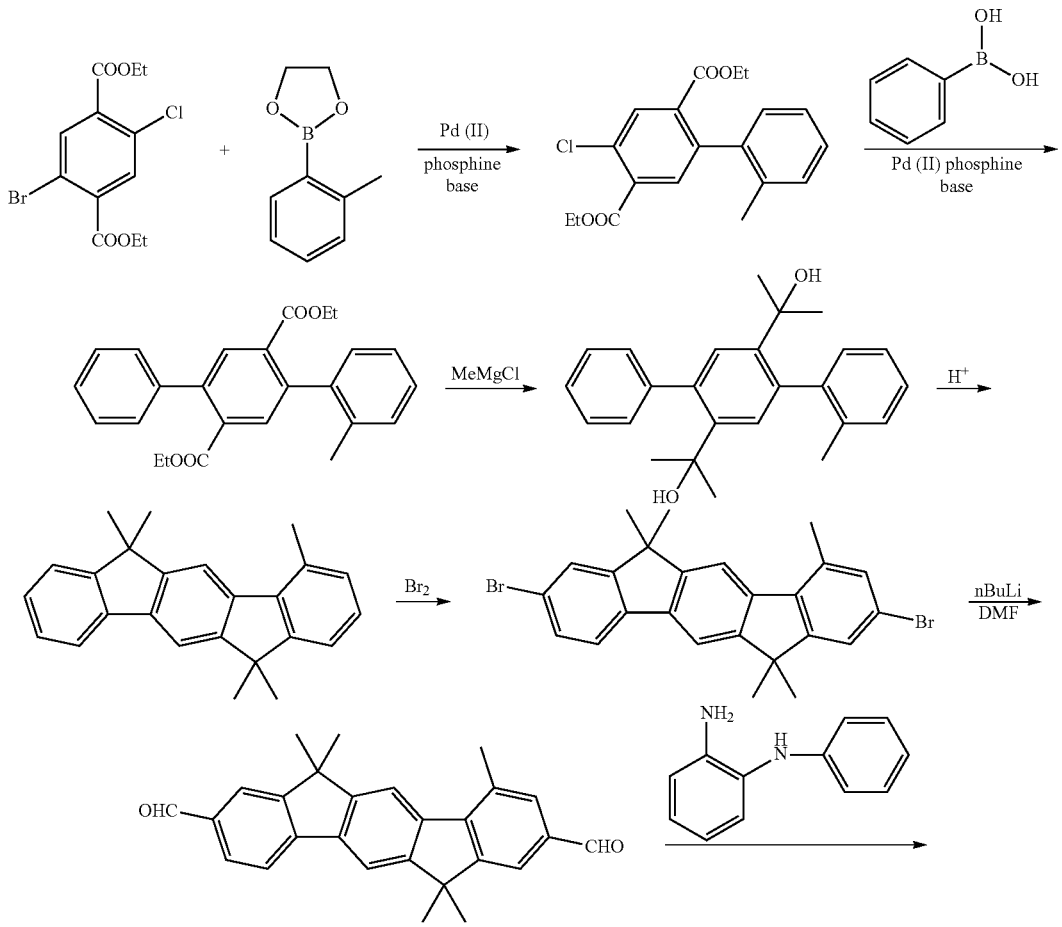

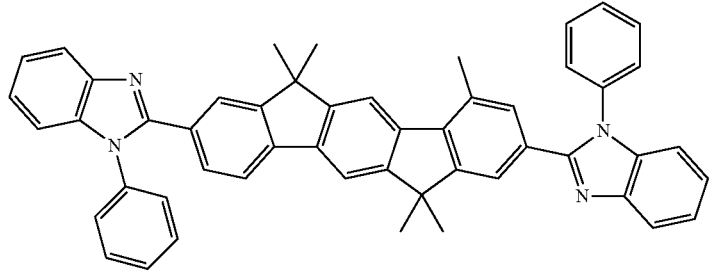

Firstly, the indenofluorene skeleton is synthesised. This is carried out by Suzuki coupling of a methyl-substituted phenylboronic acid derivative to the central 1-bromo-4-chlorobenzene derivative. The less-reactive chlorine substituent on the central phenylene group is subsequently reacted with unsubstituted phenylboronic acid in a second Suzuki coupling. The terphenyl compound obtained corresponds to the starting compound in Scheme 1. The C(Me)$_2$ bridges are formed by the addition reaction of MeMgCl onto the aromatic carboxylic acid ester groups and subsequent acid-catalysed ring-closure reaction. The trans-indenofluorene skeleton obtained is subsequently brominated.

A multiplicity of compounds according to the invention can be prepared from the resultant halogenated intermediate by organometallic coupling to aryl or heteroaryl groups. However, alternative reactions for the introduction of the groups Ar can also be employed, as already mentioned in connection with step c) above. In the present example, the bromine substituents are converted into aldehyde substituents by reaction with n-BuLi and DMF. A condensation reaction with the 1,2-diaminobenzene derivative shown to give the benzimidazole compound according to the invention is subsequently carried out.

The compounds according to the invention described above, in particular compounds which are substituted by reactive leaving groups, such as bromine, iodine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (1), where the bond(s) to the polymer, oligomer or dendrimer may be localised at any desired positions substituted by R, $R^1$ or $R^2$ in formula (1). Depending on the linking of the compound of the formula (1), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched dendritic. In the structures linked in a linear manner, the units of the formula (1) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) may, for example, be linked via a trivalent or polyvalent group, for example via a trivalent or polyvalent aromatic or heteroaromatic group, to give a branched or dendritic oligomer or polymer.

For the recurring units of the formula (1) in oligomers, dendrimers and polymers, the same preferences apply as described above for compounds of the formula (1).

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N linking are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 03/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterisation of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The invention also relates to formulations comprising at least one compound of the formula (1) or a polymer, oligomer or dendrimer containing at least one unit of the formula (1) and at least one solvent, preferably an organic solvent.

The compounds of the formula (1) according to the invention are suitable for use in electronic devices, in particular in organic electroluminescent devices (OLEDs). Depending on the substitution, the compounds are employed in different functions and layers, but preferably as electron-transport material, as fluorescent emitter material, as electron-blocking material or as matrix material for fluorescent or phosphorescent dopants. The precise use of the compounds here depends, in particular, on the choice of the groups Ar, but also on the choice of the groups X and the substituents R, $R^1$ and $R^2$.

The invention therefore furthermore relates to the use of the compounds of the formula (1) according to the invention in electronic devices, in particular in organic electroluminescent devices.

It is preferred for the purposes of the invention for the compounds of the formula (1) according to the invention or the polymers, oligomers or dendrimers according to the invention to be employed as electron-transport material in an electron-transport layer in the electronic device. Preferred compounds in this case are compounds of the formula (1) which contain one or more electron-deficient heteroaryl groups, such as, for example, triazine, pyridazine, pyrazine, pyrimidine or benzimidazole.

If the compounds according to the invention are employed as electron-transport material in an organic electroluminescent device, they can also be employed in accordance with the invention in combination with an organic or inorganic alkali-metal compound. "In combination with an organic alkali-metal compound" here means that the compounds according to the invention and the alkali-metal compound are either in the form of a mixture in one layer or separately in two successive layers. In a preferred embodiment of the invention, the compounds according to the invention and the organic alkali-metal compound are in the form of a mixture in one layer.

An organic alkali-metal compound in the sense of this invention is intended to be taken to mean a compound which contains at least one alkali metal, i.e. lithium, sodium, potassium, rubidium or caesium, and which furthermore contains at least one organic ligand. Suitable organic alkali-metal compounds are, for example, the compounds disclosed in WO 07/050,301, WO 07/050,334 and EP 1144543. These are incorporated into the present application by way of reference.

Preferred organic alkali-metal compounds are the compounds of the following formula (A),

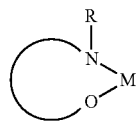

formula (A)

where R has the same meaning as described above, the curved line represents two or three atoms and bonds which are necessary to make up a 5- or 6-membered ring with M, where these atoms may also be substituted by one or more radicals R, and M represents an alkali metal selected from the group consisting of lithium, sodium, potassium, rubidium and caesium.

It is possible here for the complex of the formula (A) to be in monomeric form, as depicted above, or for it to be in the form of aggregates, for example comprising two alkali-metal ions and two ligands, four alkali-metal ions and four ligands, six alkali-metal ions and six ligands, or other aggregates.

Preferred compounds of the formula (A) are the compounds of the following formulae (A') and (A"),

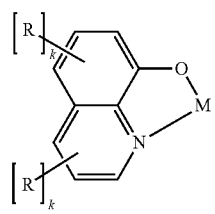

formula (A')

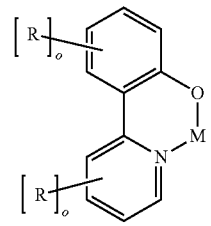

formula (A")

where k is equal to 0, 1, 2 or 3 and o is equal to 0, 1, 2, 3 or 4, and the other symbols used have the meanings given above.

Further preferred organic alkali-metal compounds are the compounds of the following formula (B),

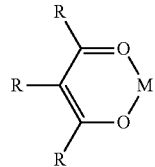

formula (B)

where the symbols used have the same meaning as described above.

The alkali metal M is preferably selected from lithium, sodium and potassium, particularly preferably lithium and sodium, very particularly preferably lithium.

Particular preference is given to a compound of the formula (A'), in particular where M=lithium. Furthermore, the index k is very particularly preferably =0. The compound is thus very particularly preferably unsubstituted lithium quinolinate.

The organic electroluminescent device very particularly preferably comprises a mixture of a compound according to the invention which contains an electron-deficient heteroaromatic group and an organic alkali-metal compound of the formula (A'), preferably where M=lithium, in particular unsubstituted lithium quinolinate.

Examples of suitable organic alkali-metal compounds are structures (1) to (45) shown in the following table.

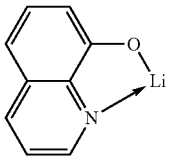
(1)

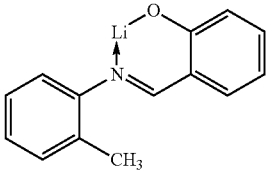
(2)

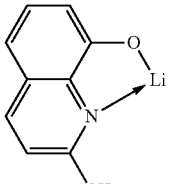
(3)

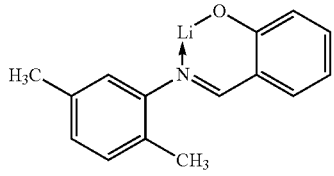
(4)

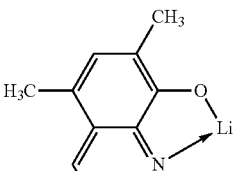
(5)

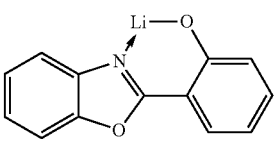
(6)

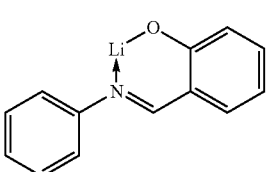
(7)

-continued

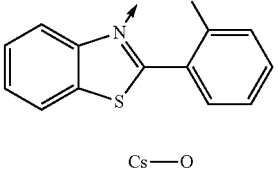
(8)

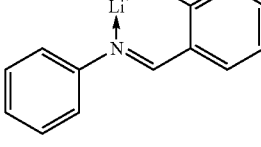
(9)

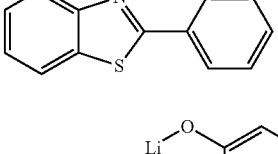
(10)

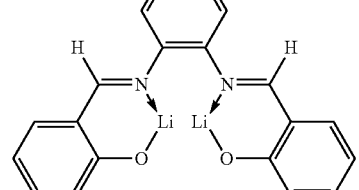
(11)

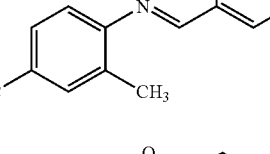
(12)

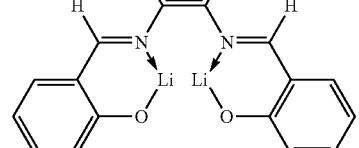
(13)

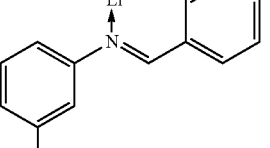
(14)

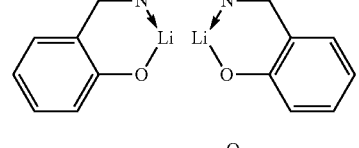
(15)

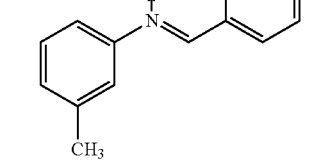
(16)

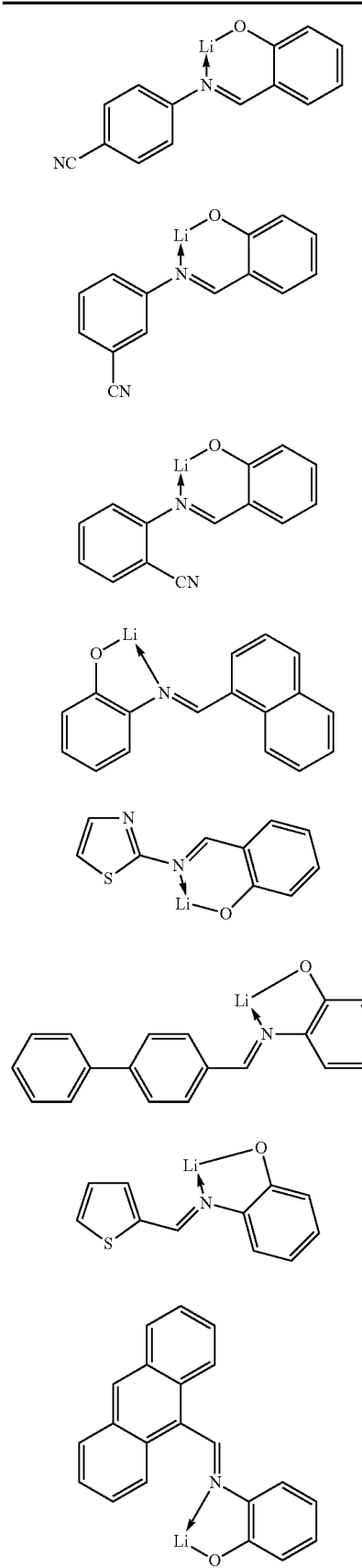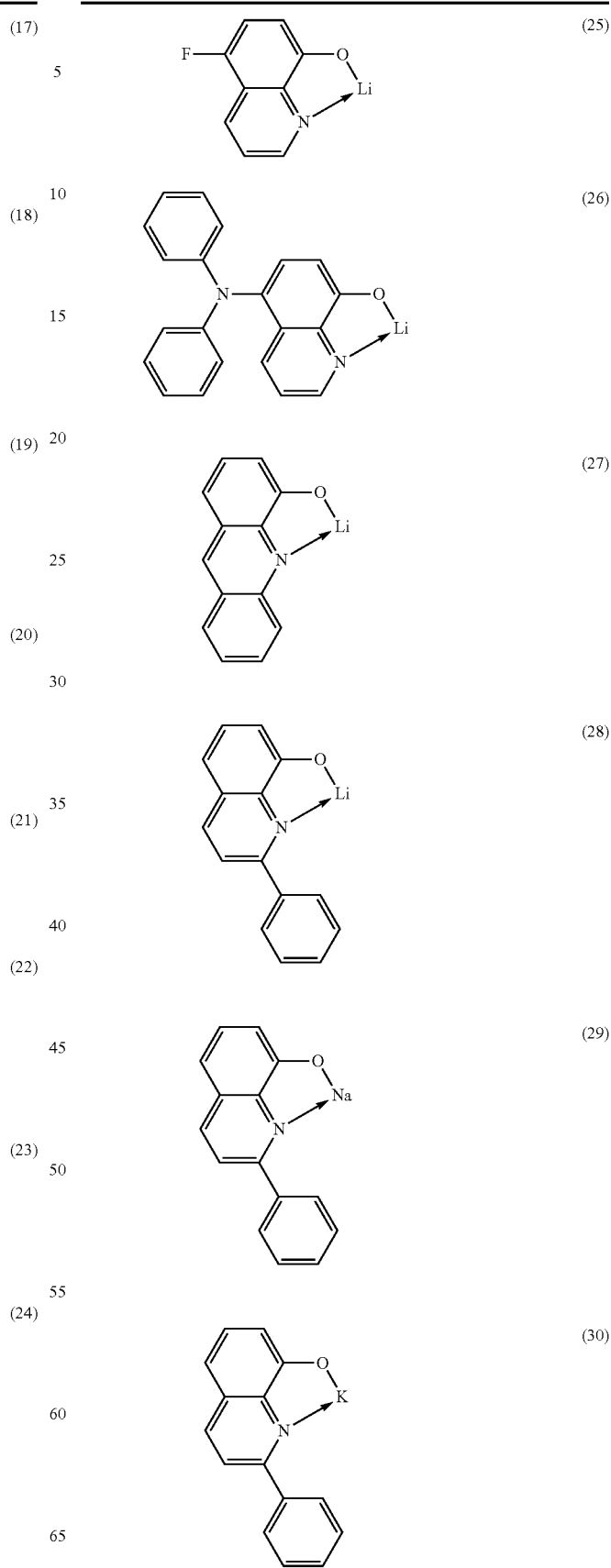

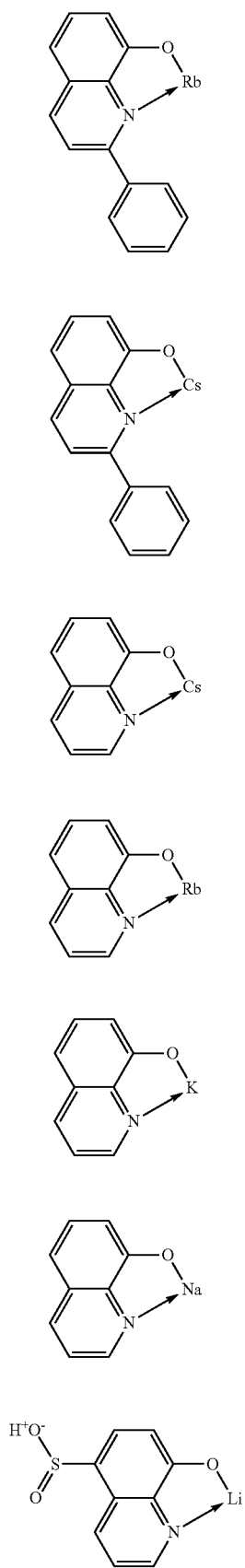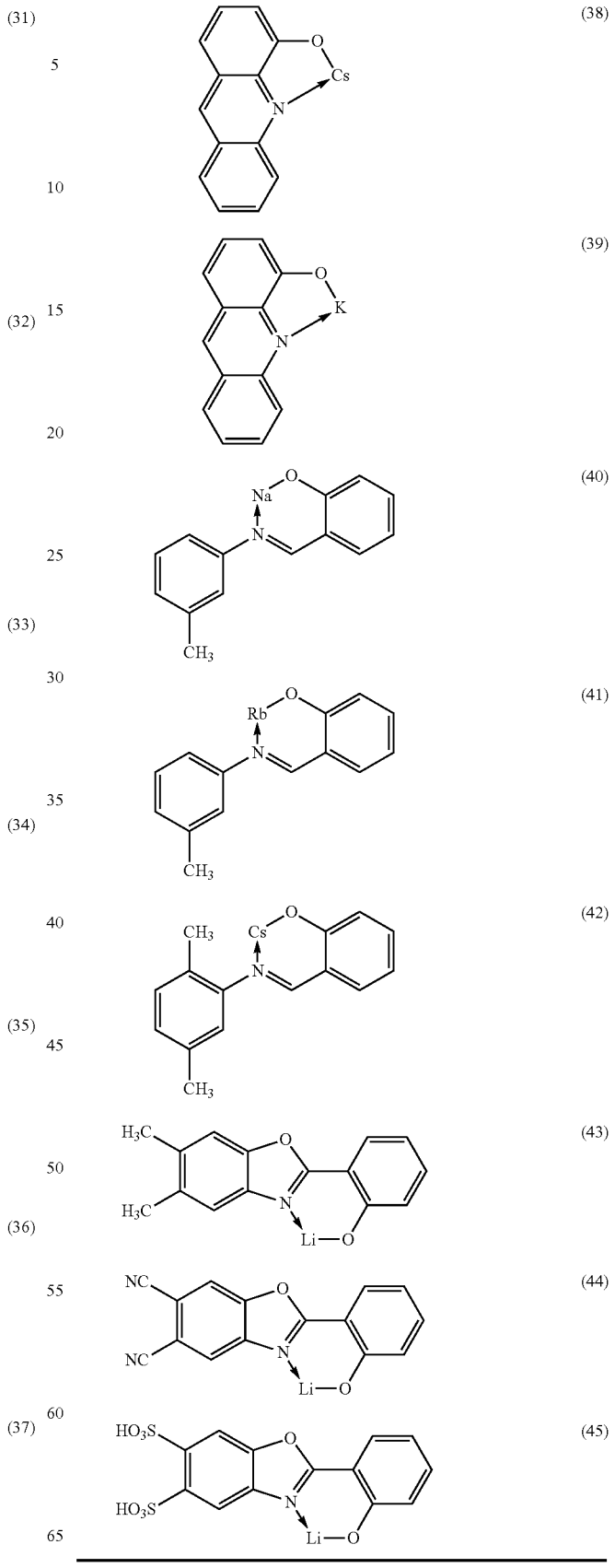

If the compound according to the invention and the organic or inorganic alkali-metal compound are in the form of a mixture, the ratio of the compound according to the invention to the organic alkali-metal compound is preferably 20:80 to 80:20, particularly preferably 30:70 to 70:30, very particularly preferably 30:70 to 50:50, in particular 30:70 to 45:55, in each case based on the volume. The organic alkali-metal compound is thus particularly preferably present in a higher proportion than the compound according to the invention.

If the compound according to the invention and the organic or inorganic alkali-metal compound are in the form of a mixture, the layer thickness of this electron-transport layer is preferably between 3 and 150 nm, particularly preferably between 5 and 100 nm, very particularly preferably between 10 particularly preferably between 15 and 40 nm.

If the compound according to the invention and the organic or inorganic alkali-metal compound are present in the two successive layers, the layer thickness of the layer which comprises the compound according to the invention is preferably between 3 and 150 nm, particularly preferably between 5 and 100 nm, very particularly preferably between 10 and 60 nm, in particular between 15 and 40 nm. The layer thickness of the layer which comprises the organic or inorganic alkali-metal compound and which is arranged between the layer comprising the compound according to the invention and the cathode is preferably between 0.2 and 10 nm, particularly preferably between 0.4 and 5 nm and very particularly preferably between 0.8 and 4 nm.

In a further embodiment of the invention, the compounds of the formula (1) are employed as electron-blocking materials, preferably in an electron-blocking layer. In this case, it is preferred for the compounds to be employed as pure substances. The electronic device comprising one or more compounds of the formula (1) as electron-blocking material particularly preferably additionally comprises one or more phosphorescent emitter materials, preferably in an emitting layer.

In a further embodiment of the invention, the compounds of the formula (1) are employed as emitting materials, preferably as fluorescent green- or blue-emitting materials, particularly preferably as fluorescent blue materials. The compounds of the formula (1) are preferably in this case employed in combination with a matrix material.

The proportion of the compound of the formula (1) in the mixture of the emitting layer is in this case between 0.1 and 50.0% by vol., preferably between 0.5 and 20.0% by vol., particularly preferably between 1.0 and 10.0% by vol. Correspondingly, the proportion of the matrix material is between 50.0 and 99.9% by vol., preferably between 80.0 and 99.5% by vol., particularly preferably between 90.0 and 99.0% by vol.

Suitable matrix materials for use as fluorescent emitter materials in combination with the compounds according to the invention are materials from various classes of substance. Preferred matrix materials are selected from the classes of the oligoarylenes (for example 2, 2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145,239). Suitable matrix materials are furthermore also the compounds according to the invention. Particularly preferred matrix materials, apart from the compounds according to the invention, are selected from the classes of the oligoarylenes, comprising naphthalene, anthracene, benzanthracene and/or pyrene, or atropisomers of these compounds, the oligoarylenevinylenes, the ketones, the phosphine oxides and the sulfoxides. Very particularly preferred matrix materials, apart from the compounds according to the invention, are selected from the classes of the oligoarylenes, comprising anthracene, benzanthracene and/or pyrene, or atropisomers of these compounds. An oligoarylene in the sense of this invention is intended to be taken to mean a compound in which at least three aryl or arylene groups are bonded to one another.

In a yet further embodiment of the invention, the compounds of the formula (1) are employed as matrix materials for fluorescent or phosphorescent emitters, preferably for phosphorescent emitters.

A matrix material in a system comprising matrix and dopant is taken to mean the component which is present in the higher proportion in the system. In the case of a system comprising one matrix material and a plurality of dopants, the matrix material is taken to mean the component whose proportion in the mixture is the highest.

The proportion of the matrix material of the formula (1) in the emitting layer is between 50.0 and 99.9% by vol., preferably between 80.0 and 99.5% by vol., particularly preferably between 90.0 and 99.0% by vol. Correspondingly, the proportion of the dopant is between 0.01 and 50.0% by vol., preferably between 0.5 and 20.0% by vol. and particularly preferably between 1.0 and 10.0% by vol.

Preferred fluorescent dopants are selected from the class of the arylamines. Corresponding phosphines and ethers are defined analogously to the amines. An arylamine or an aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 06/122630, benzoindenofluorenamines or benzoindenofluorenediamines, for example in accordance with WO 08/006,449, and dibenzoindenofluorenamines or dibenzoindenofluorenediamines, for example in accordance with WO 07/140,847. Further examples are described in WO 07/115,610. Preference is furthermore given to the condensed hydrocarbons disclosed in the application WO 2010/012328.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescence are suitable. The person skilled in the art will also be able to employ further phosphorescent complexes, without inventive step, in combination with the compounds of the formula (1) according to the invention in the emitting layer.

Particularly suitable phosphorescent dopants are furthermore the compounds shown in the following table.

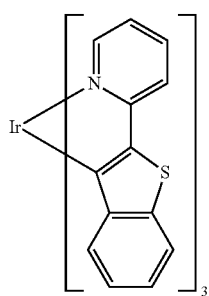

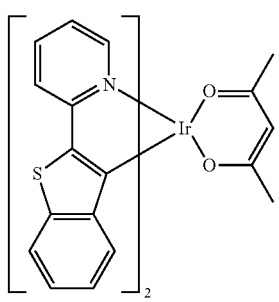

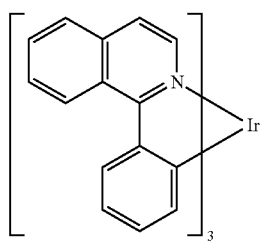

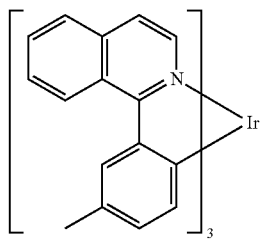

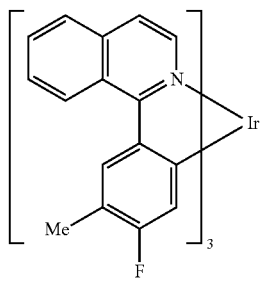

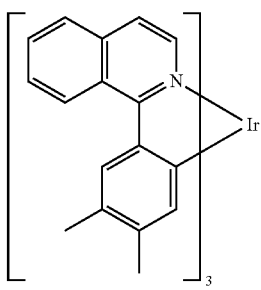

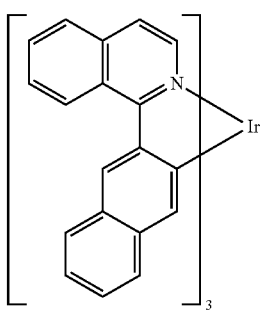

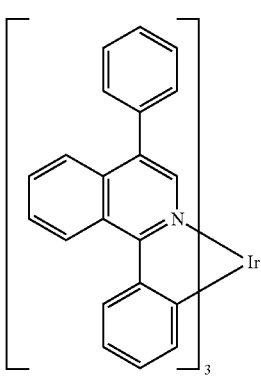

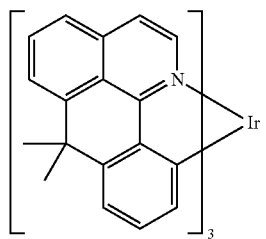
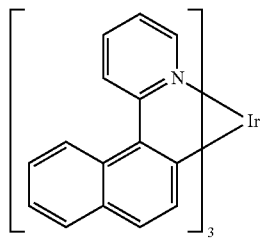
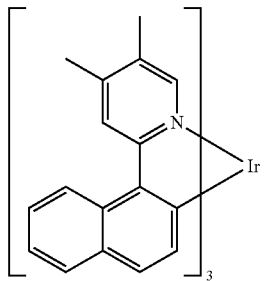
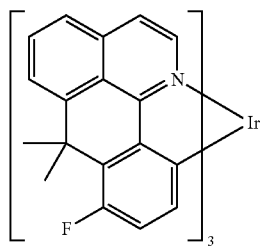
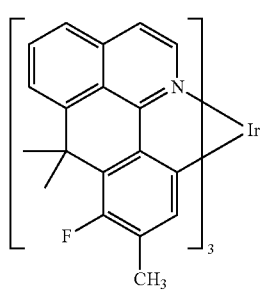
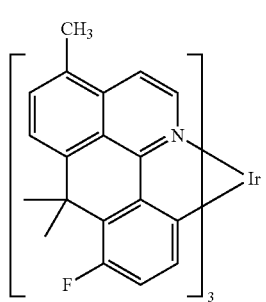
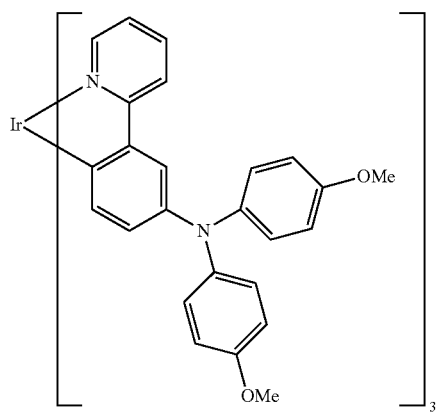
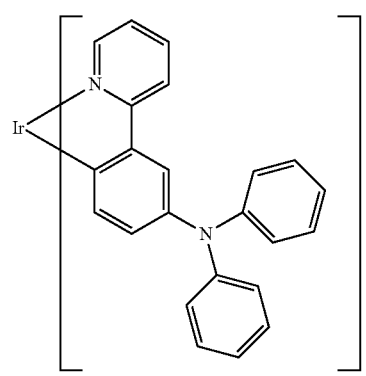
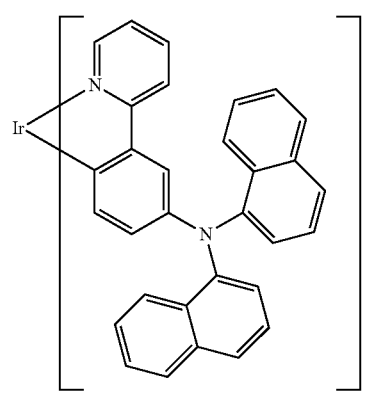
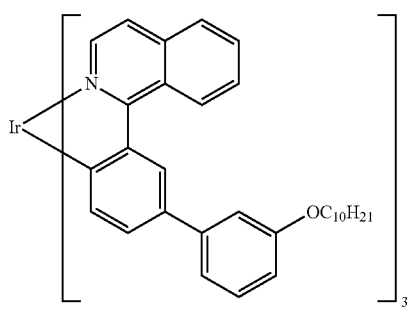

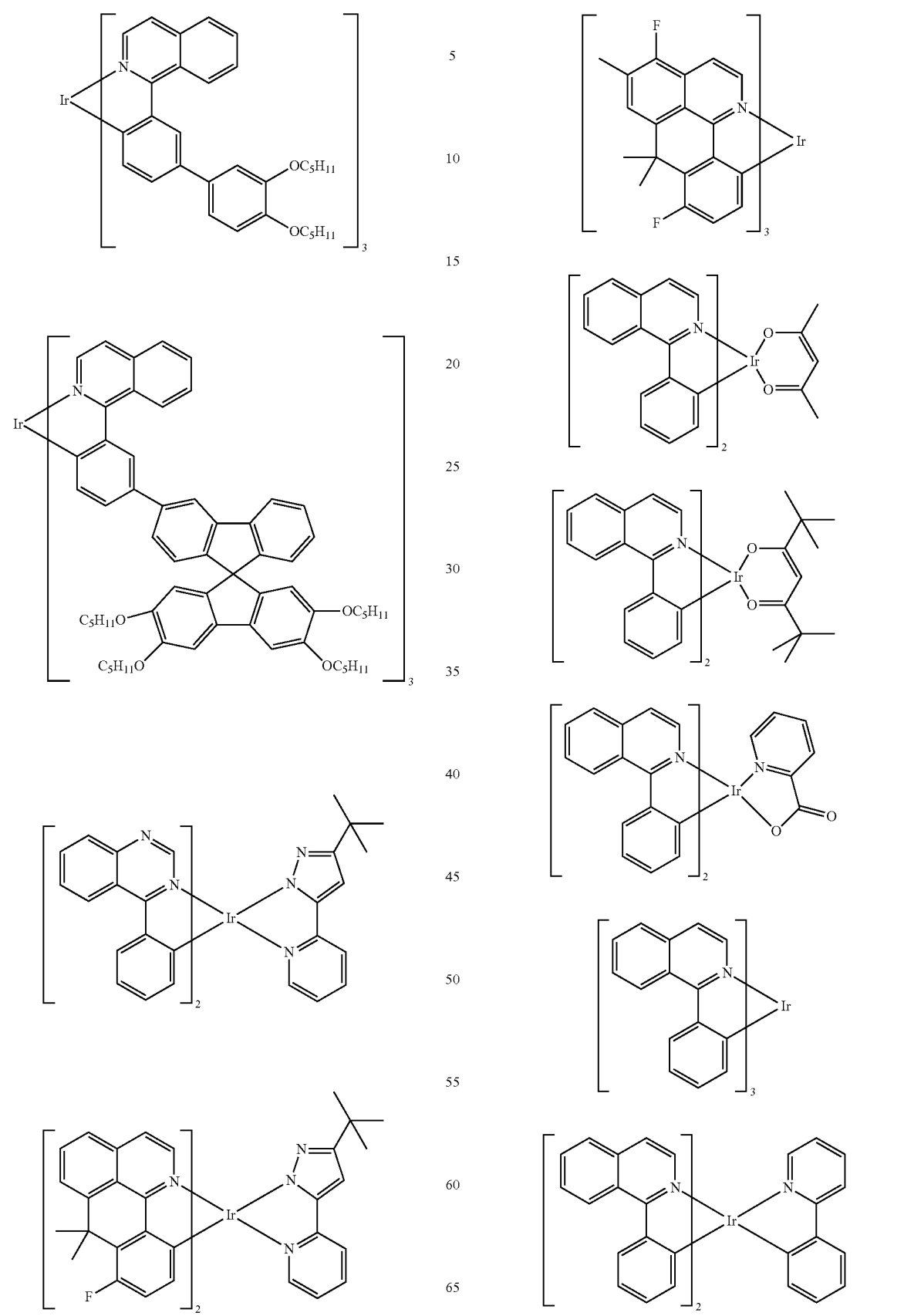

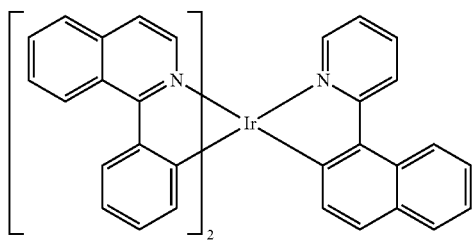
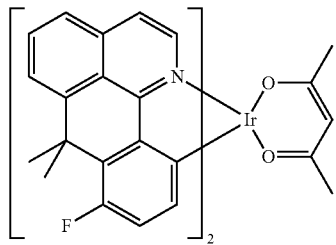
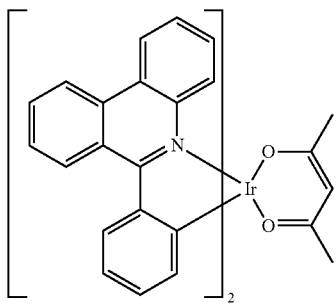
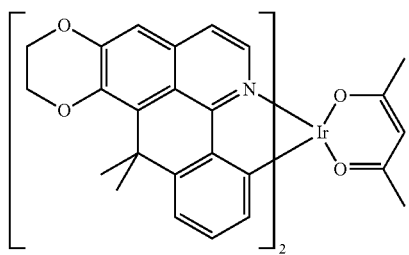
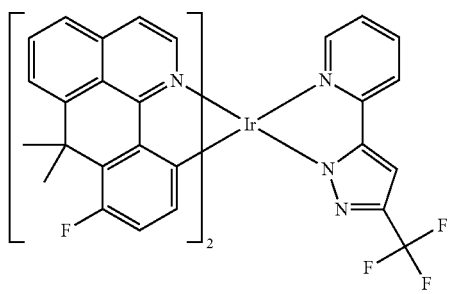
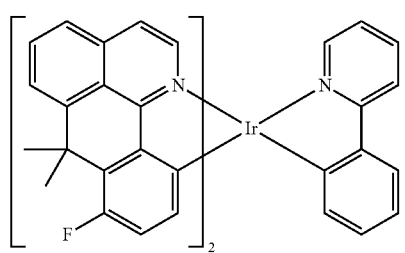
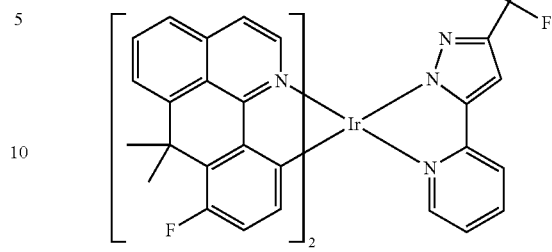
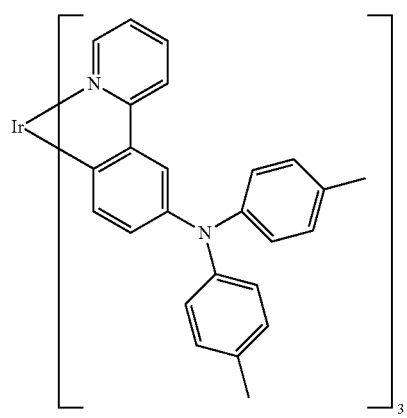
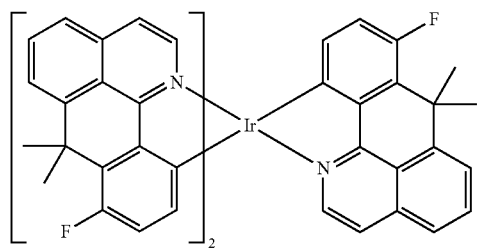
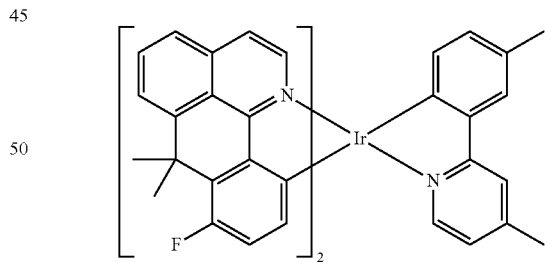
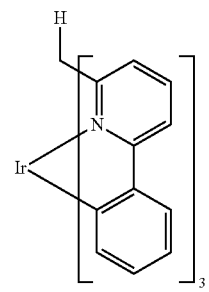

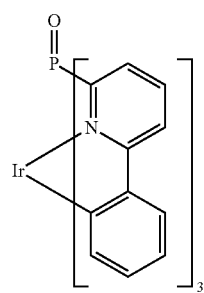
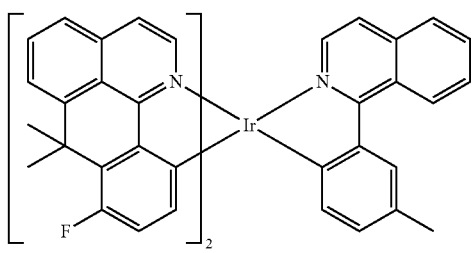
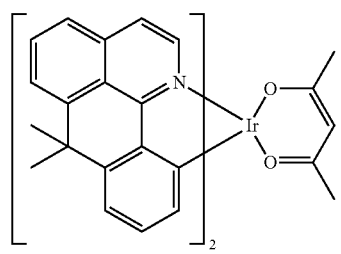
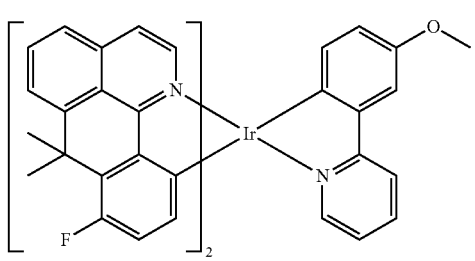
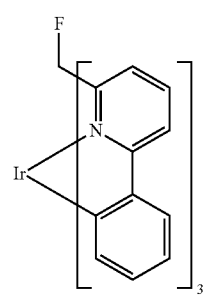
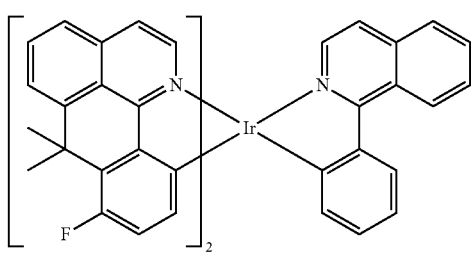
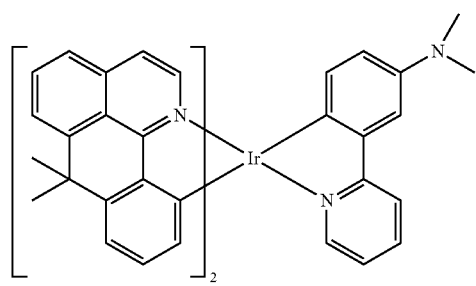
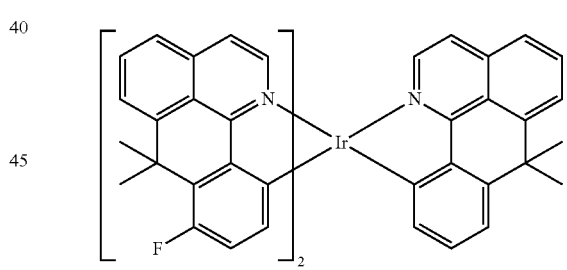
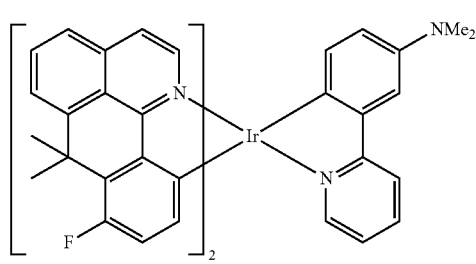
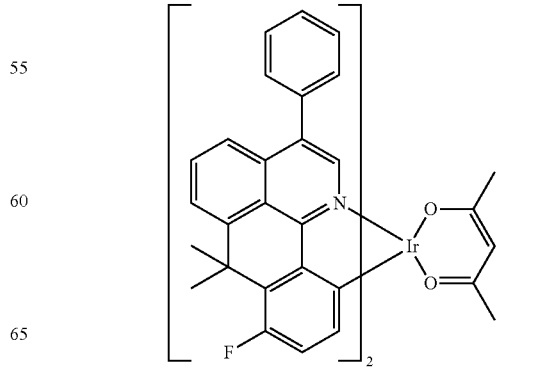

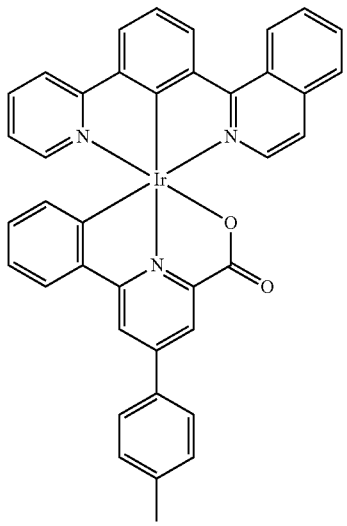
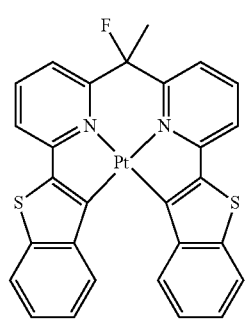
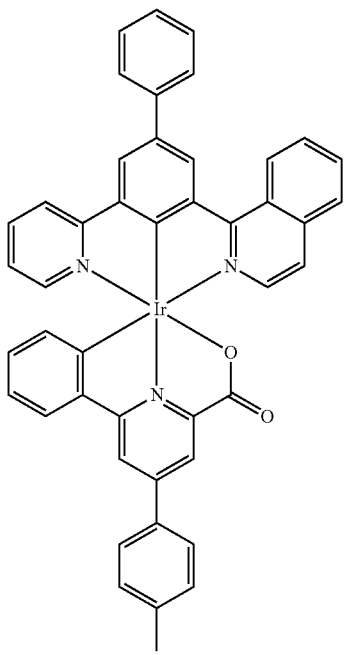
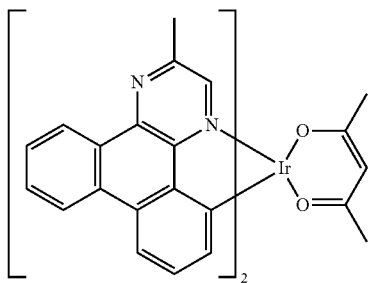
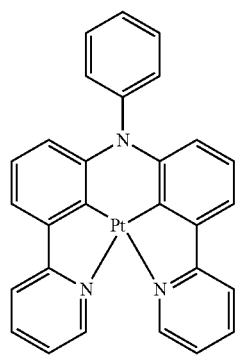
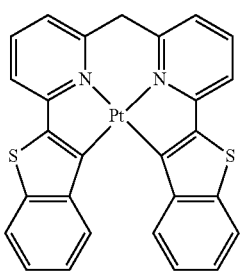
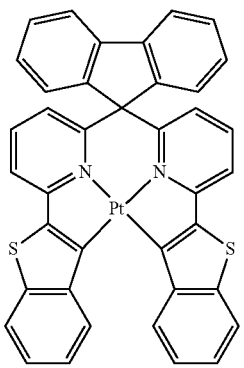
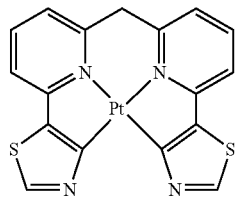

73
-continued
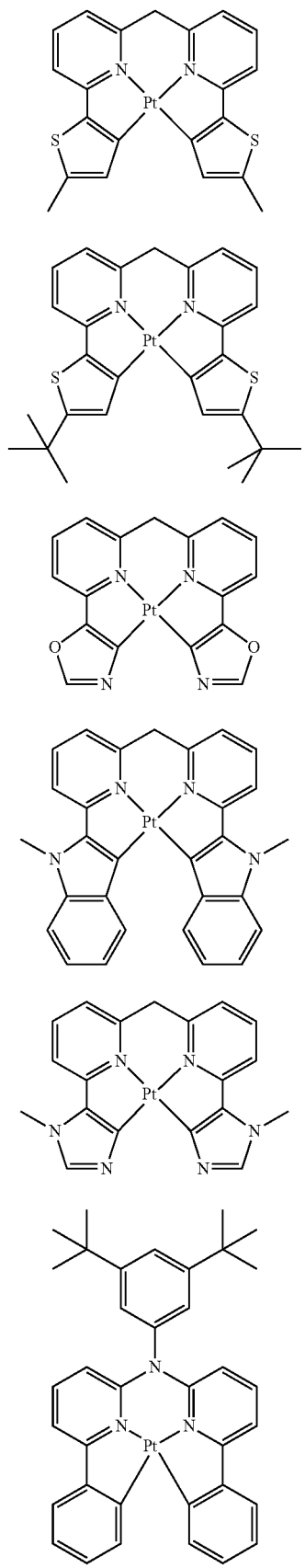
74
-continued
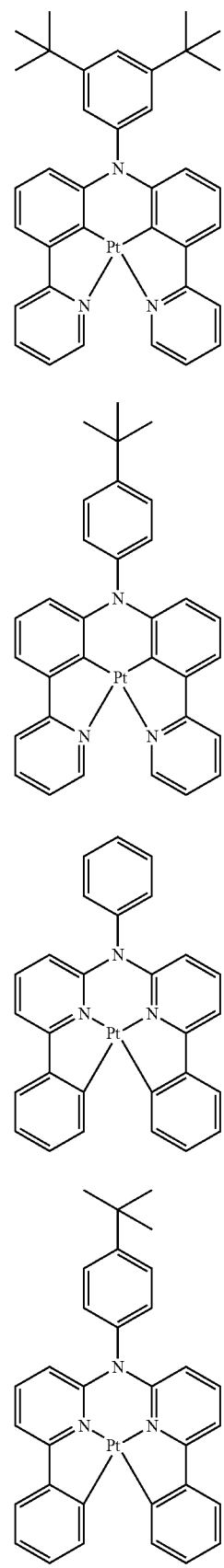

75
-continued
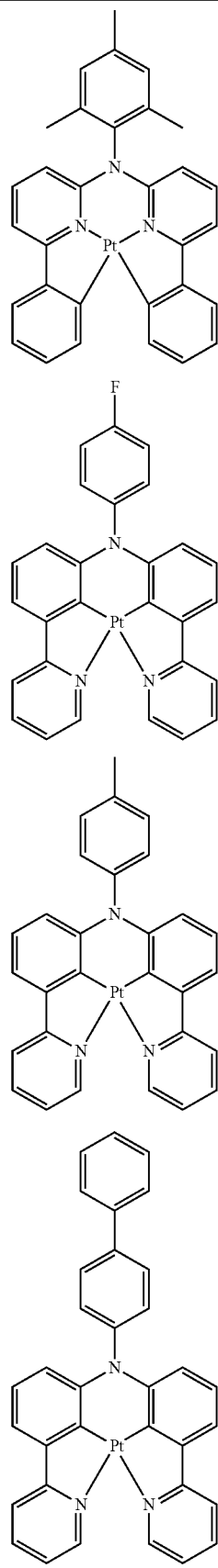
76
-continued
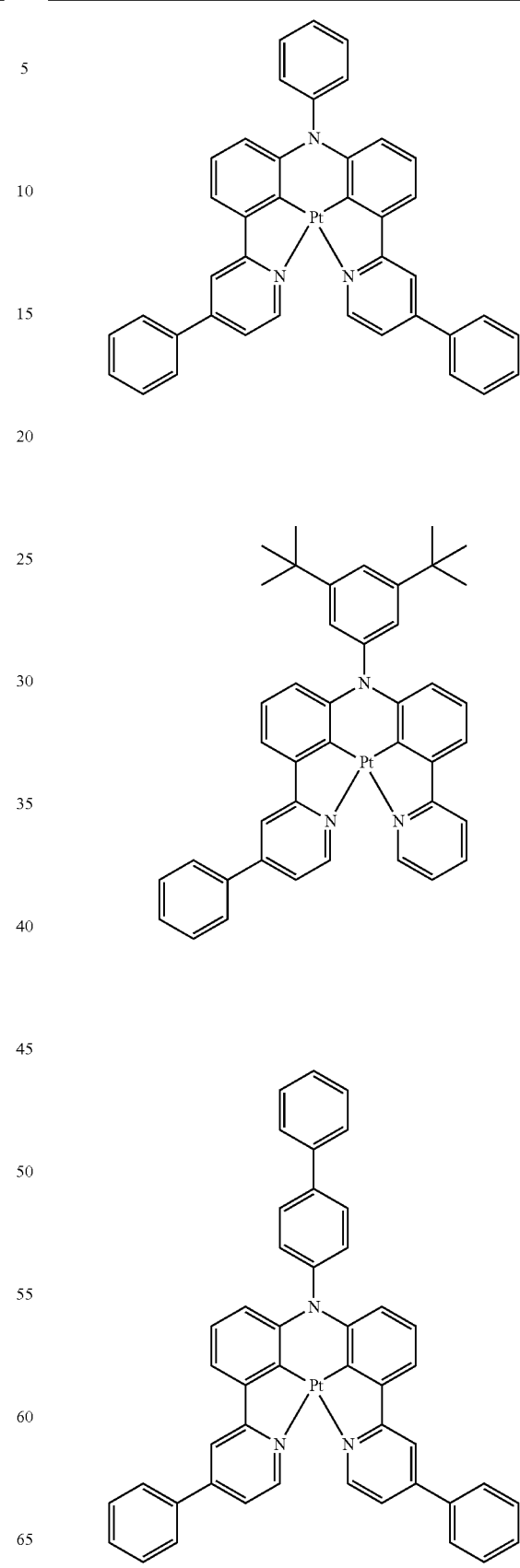

| 77 -continued | 78 -continued |
|---|---|
| 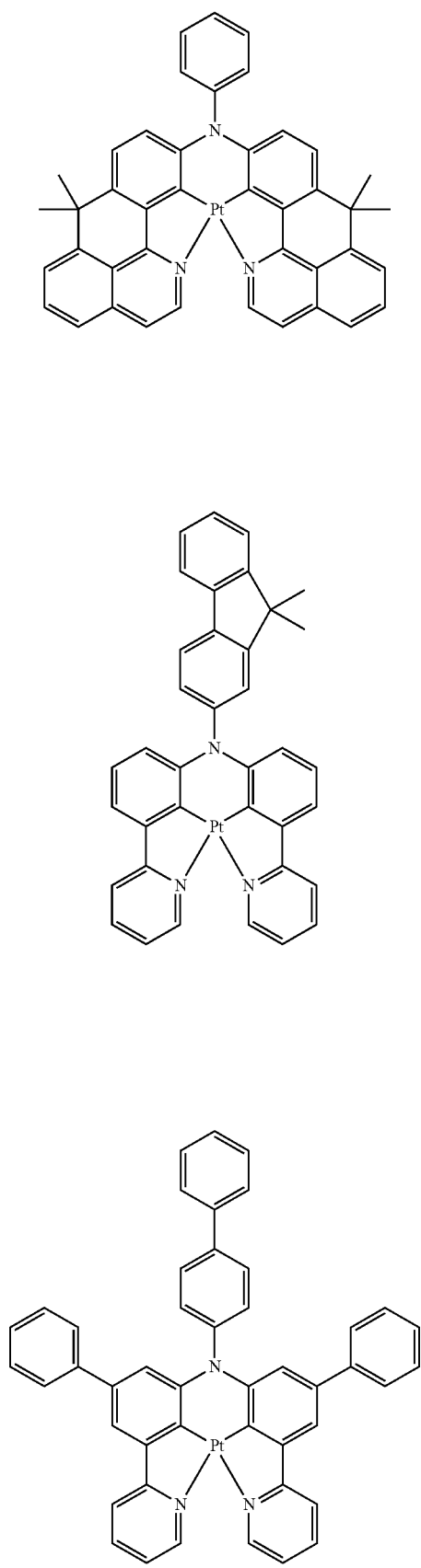 | 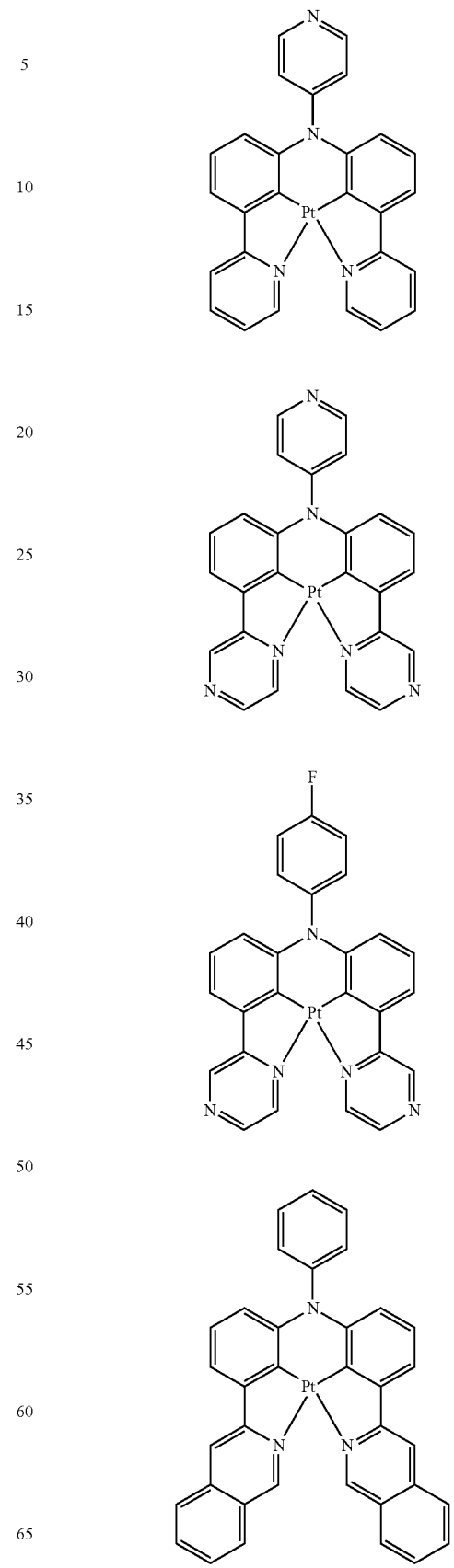 |

-continued
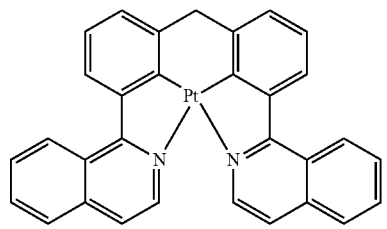
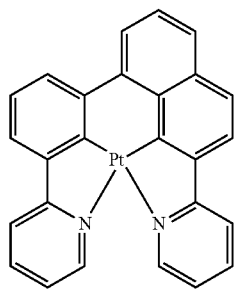
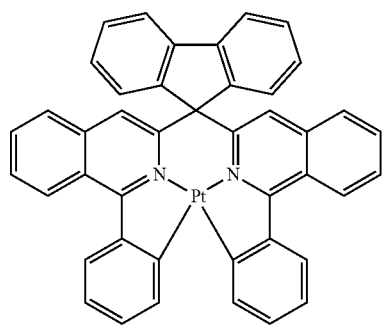
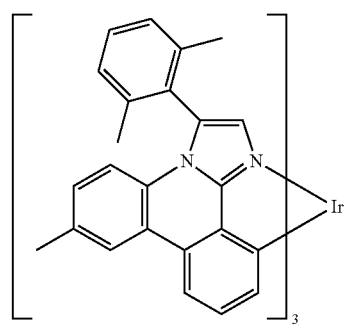
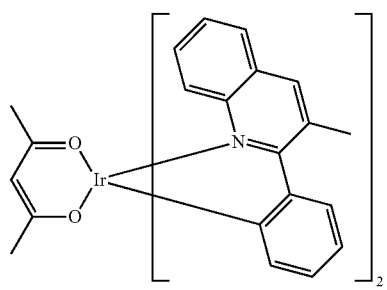
-continued
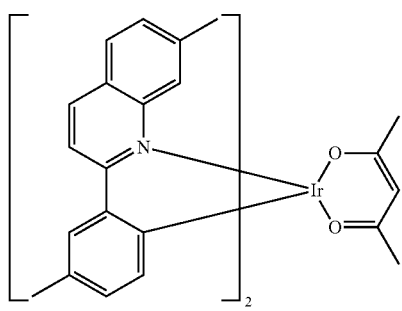
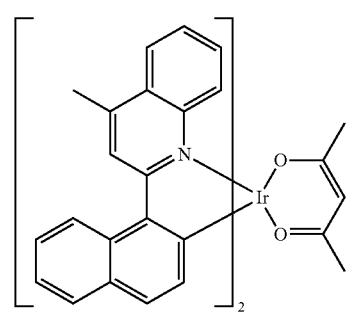
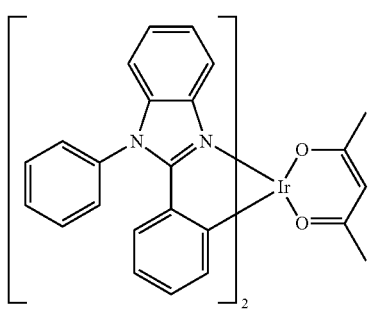
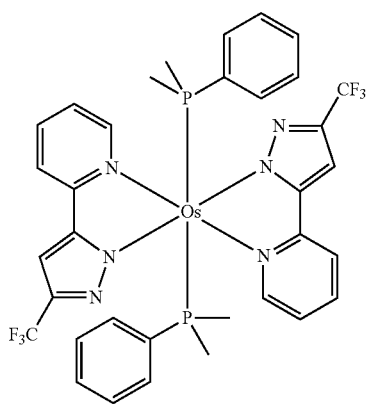

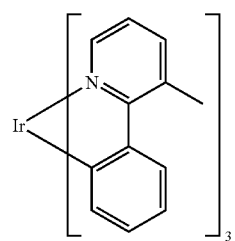
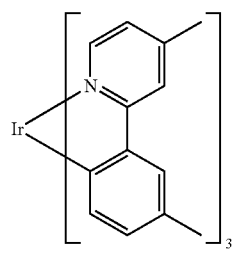
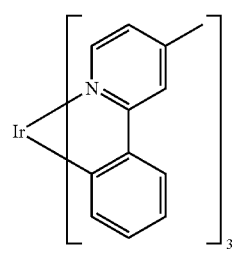
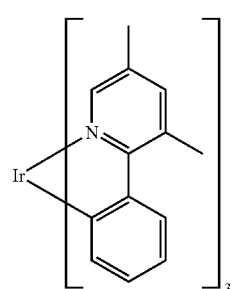
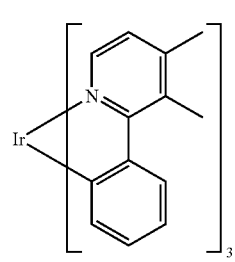
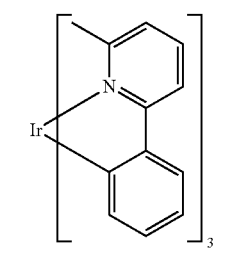
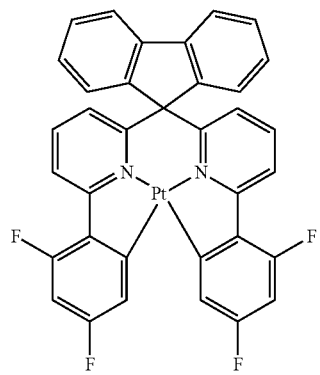
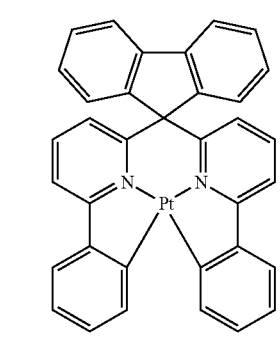
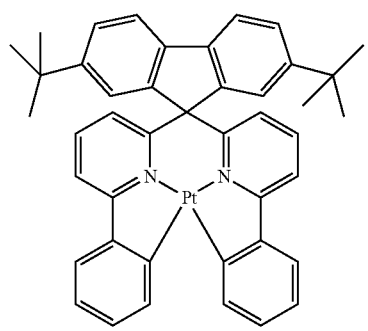
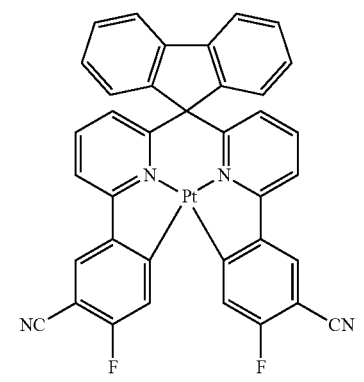

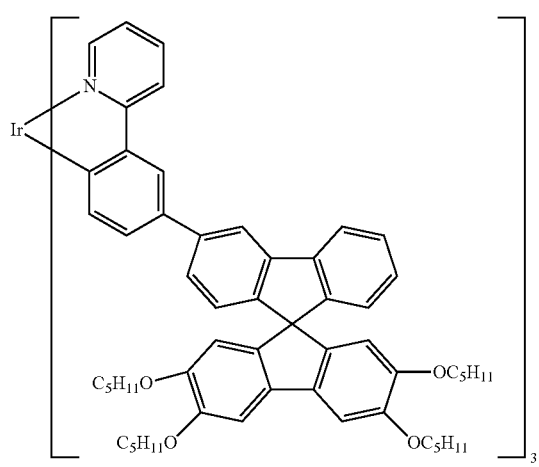
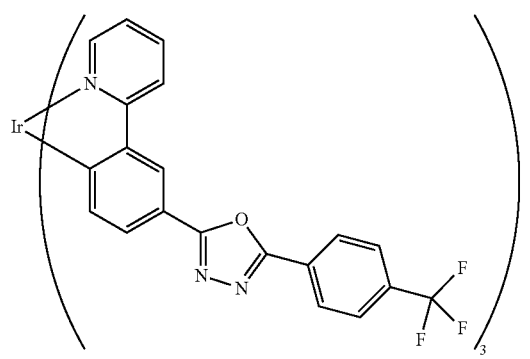
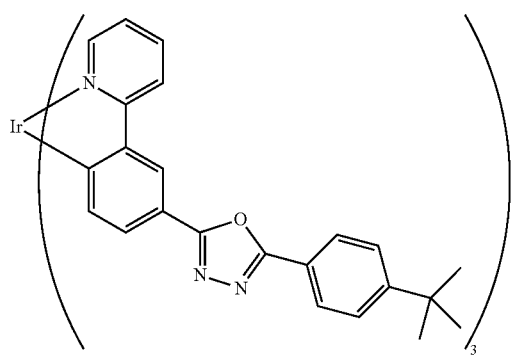
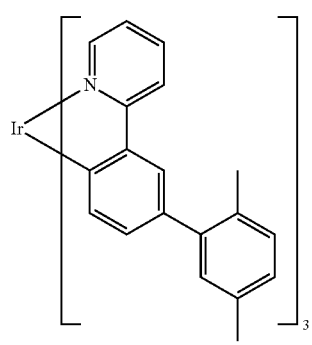
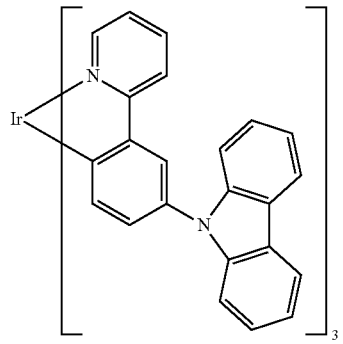
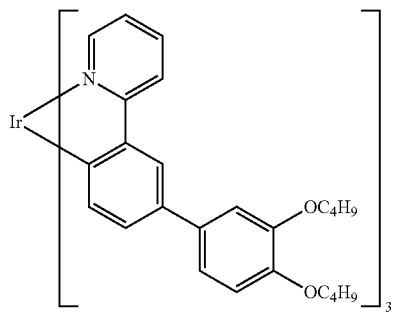
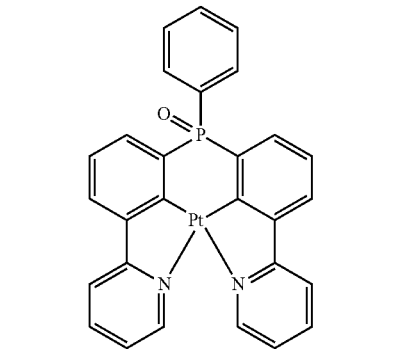
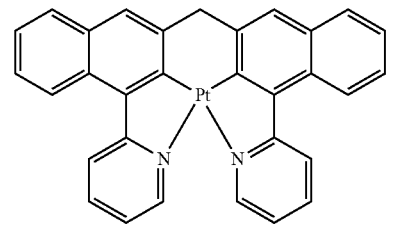
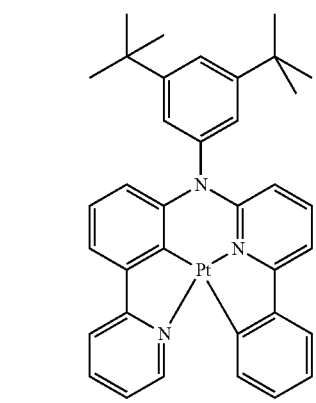

85
-continued
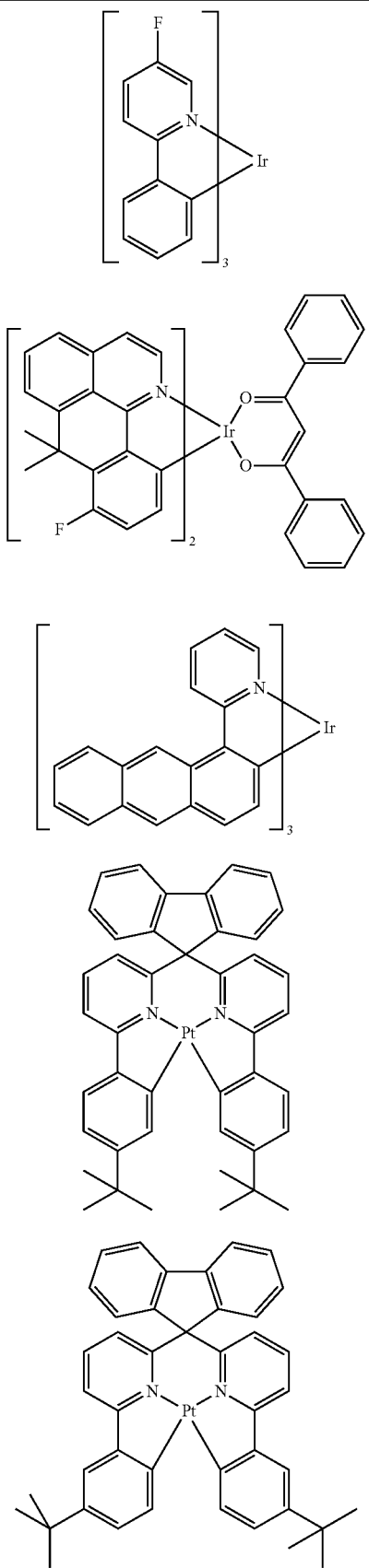
86
-continued
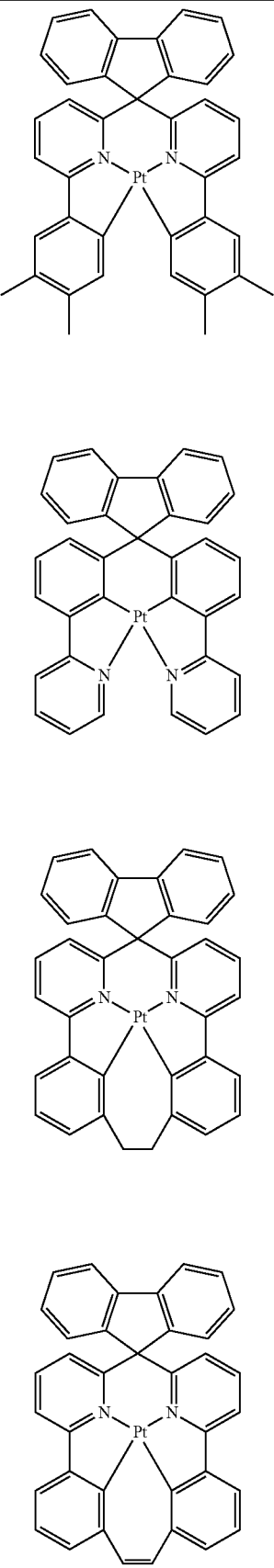

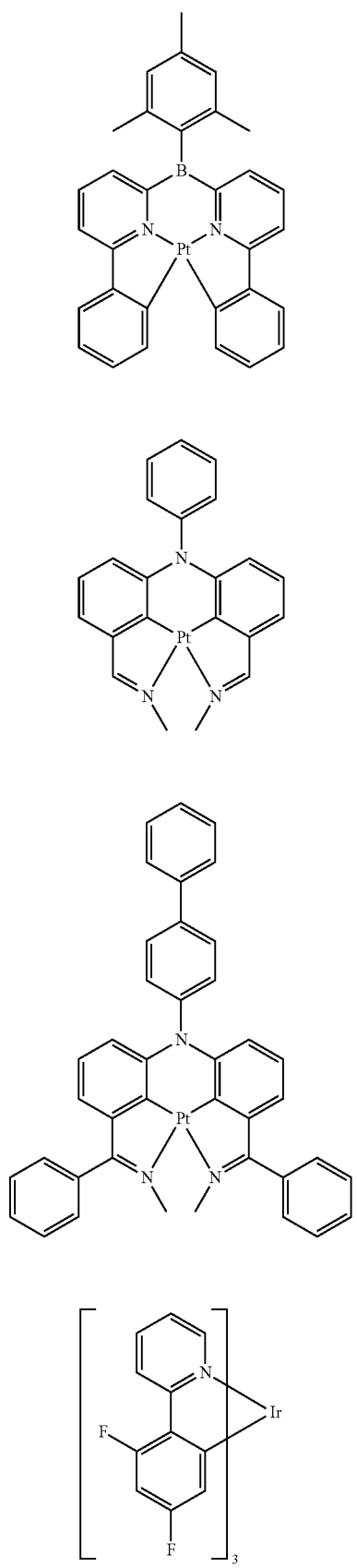
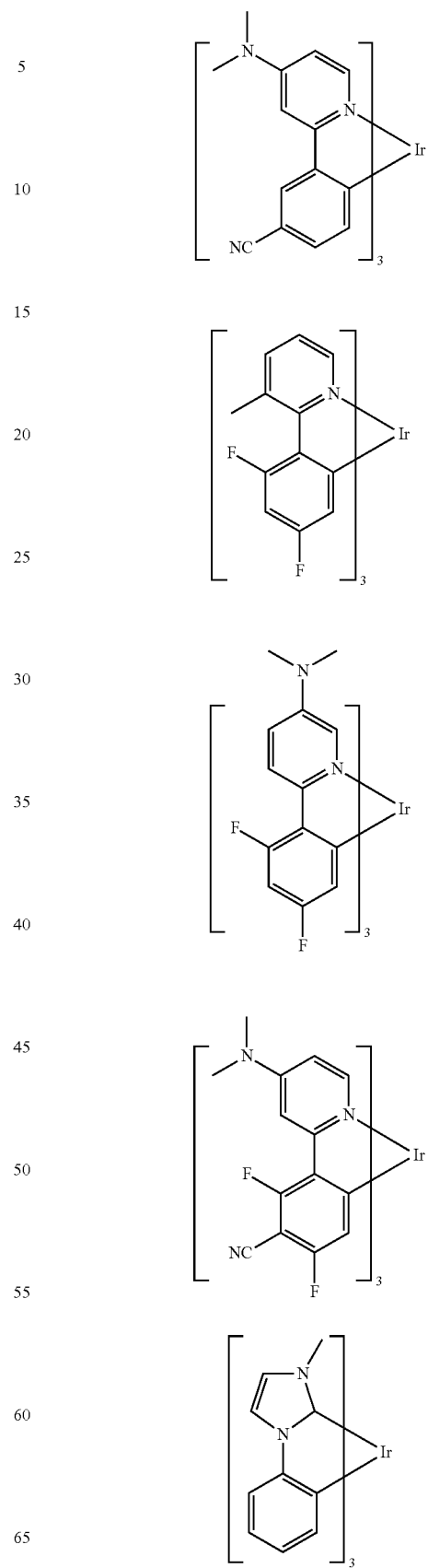

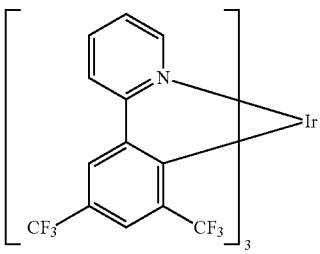
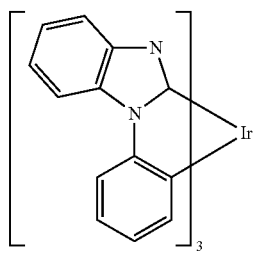
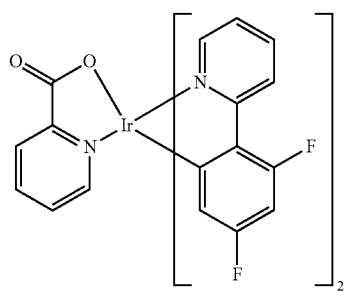
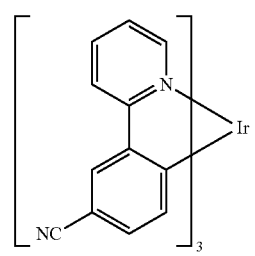
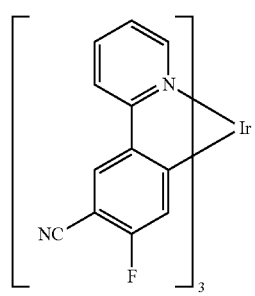
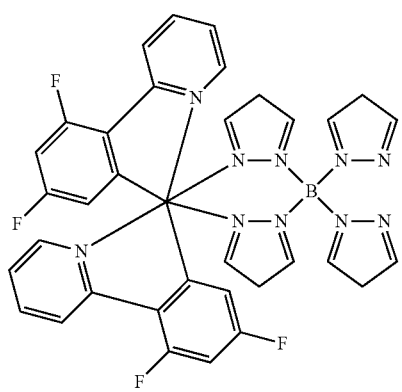
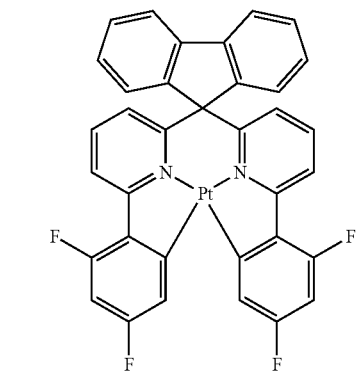
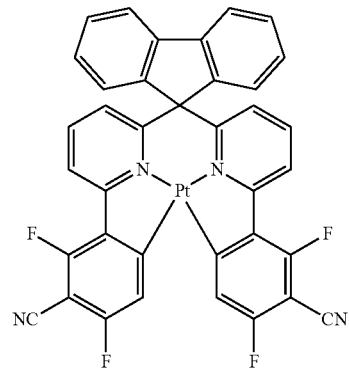

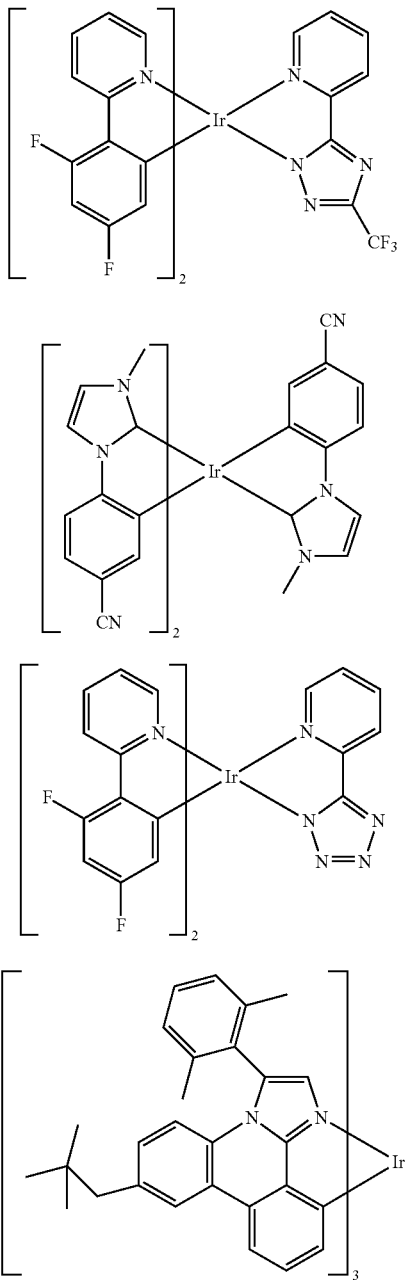

The invention still furthermore relates to electronic devices, in particular organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), which comprise at least one compound of the formula (1) or an oligomer, dendrimer or polymer according to the invention. It is particularly preferred for the electronic device to be an organic electroluminescent device (OLED).

The organic electroluminescent devices preferably comprise an anode, a cathode and at least one emitting layer, characterised in that at least one organic layer, which may be an emitting layer or another layer, comprises at least one compound of the formula (1) or at least one oligomer, dendrimer or polymer according to the invention.

Apart from the cathode, the anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present, and the choice of the layers is always dependent on the compounds used and in particular also on whether the device is a fluorescent or phosphorescent electroluminescent device.

The organic electroluminescent device may also comprise a plurality of emitting layers, where at least one organic layer comprises at least one compound of the formula (1) or a polymer, oligomer or dendrimer as defined above. These emission layers particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where one or more of these layers may comprise one or more compounds of the formula (1) or a polymer, oligomer or dendrimer as defined above and where the three layers exhibit blue, green and orange or red emission (for the basic structure see, for example, WO 05/011013). Emitters which have broadband emission bands and thus exhibit white emission are likewise suitable for white emission. Alternatively and/or additionally, the compounds according to the invention may also be present in the hole-transport layer or in another layer.

Examples of preferred hole-transport materials which can be used in a hole-transport or hole-injection layer in the electroluminescent device according to the invention are indenofluorenamines and derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic ring systems (for example in accordance with U.S. Pat. No. 5,061,569), the amine derivatives disclosed in WO 95/09147, monobenzoindenofluorenamines (for example in accordance with WO 08/006,449) or dibenzoindenofluorenamines (for example in accordance with WO 07/140,847). Hole-transport and hole-injection materials which are furthermore suitable are derivatives of the compounds depicted above, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569.

The cathode preferably comprises metals having a low work function, metal alloys or multilayered structures comprising different metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, may also be used in addition to the said metals, in which case combinations of the metals, such as, for example, Ca/Ag or Ba/Ag, are then generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, Li$_2$O, BaF$_2$, MgO, NaF, CsF, Cs$_2$ CO$_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent in order to enable either the irradiation of the organic material (O-SCs) or the coupling-out of light (OLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is correspondingly (depending on the application) structured, provided with contacts and finally sealed, since the lifetime of the devices according to the invention is shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than 10$^{-5}$ mbar, preferably less than 10$^{-6}$ mbar. However, it is also possible for the initial pressure to be even lower, for example less than 10$^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between 10$^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds of the formula (1) or a soluble polymer, oligomer or dendrimer as defined above are necessary for this purpose. High solubility can be achieved through suitable substitution of the compounds.

The compounds according to the invention have one or more of the following advantages over the prior art on use in organic electroluminescent devices:
1. The organic electroluminescent devices according to the invention comprising compounds of the formula (1) have high efficiency as electron-transport materials. Furthermore, the operating voltage is preferably reduced.
2. The use of the compounds according to the invention causes a lower dependence of the voltage on the transport-layer thickness, possibly owing to improved electron mobility.
3. At the same time, the compounds according to the invention have a comparable, preferably longer, lifetime.
4. On use of the compounds according to the invention as fluorescent emitters, high efficiencies and long lifetimes are obtained.
5. The compounds according to the invention are highly suitable for use as matrix material in an emitting layer and result, in this use, in good efficiencies, long lifetimes and low operating voltages.

The present application text and also the examples below are directed to the use of the compounds according to the invention in relation to OLEDs and the corresponding displays and lighting elements. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or organic laser diodes (O-lasers), to mention but a few applications.

The present invention likewise relates to the use of the compounds according to the invention in the corresponding devices and to these devices themselves.

The invention is explained in greater detail by the following examples, without the intention of a restriction to the subject-matter of the invention being derived thereby.

WORKING EXAMPLES

The following syntheses are carried out, unless indicated otherwise, under a protective-gas atmosphere in dried solvents. The starting materials can be purchased from ALDRICH.

Example 1a

Preparation of 4,6,6,12,12-pentamethyl-6H,12H-indeno-[1,2-b]fluorene-2,8-bis-(1-phenyl-1H-benzimidazole) (ETM2)

Diethyl 4-chloro-2'-methylbiphenyl-2,5-dicarboxylate

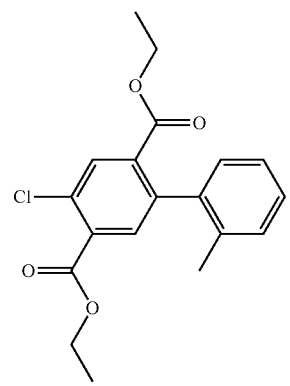 [SMILES: CCOC(=O)c1cc(-c2ccccc2C)c(C(=O)OCC)cc1Cl]

76.7 g (229 mmol) of diethyl chlorobromoterephthalate, 37 g (229 mmol) of o-tolylboronic acid ethylene glycol ester, 513 mg (2.29 mmol) of Pd(OAc)$_2$, 4.18 g (13.72 mmol) of tri(o-tolyl)phosphine and 116 g (503 mmol) of K$_2$ PO$_4$ are heated at the boil for 6 h in 280 ml of toluene, 136 ml of 1,4-dioxane and 420 ml of water. The mixture is subsequently partitioned between toluene and water, and the org. phase is washed three times with water and dried over $Na_2SO_4$. The residue remaining is distilled. The yield is 61 g (115 mmol, 50%).

Diethyl 2''-methyl-[1,1';4',1'']terphenyl-2',5'-dicarboxylate

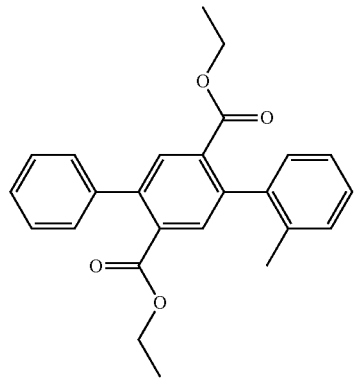 [SMILES: CCOC(=O)c1cc(-c2ccccc2C)c(C(=O)OCC)cc1-c1ccccc1]

40 g (115 mmol) of diethyl chloroterephthalate, 19.7 g (162 mmol) of benzeneboronic acid, 389 mg (1.73 mmol) of $Pd(OAc)_2$, 3.36 ml (3.4 mmol) of 1 M tri-tert-butylphosphine in toluene and 75 g (231 mmol) of $Cs_2CO_3$ are heated at the boil for 4 h in 300 ml of 1,4-dioxane. The mixture is subsequently partitioned between toluene and water, and the org. phase is washed three times with water, dried over $Na_2SO_4$ and evaporated in a rotary evaporator. The yield is 47 g (115 mmol, 99%).

2-[5'-(1-Hydroxy-1-methylethyl)-2-methyl-[1,1';4',1'']terphenyl-2'-yl]-propan-2-ol

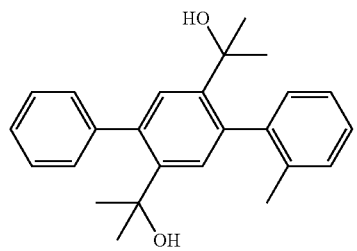 [SMILES: Cc1ccccc1-c1cc(C(C)(C)O)c(-c2ccccc2)cc1C(C)(C)O]

47 g (113 mmol) of the diester from step b) are initially introduced in 620 ml of dried THF, 226 ml (680 mmol) of a 3 M MeMgCl solution in THF are added to the suspension at 5° C., and the mixture is stirred at 5° C. for 6 h. After this time, 200 ml of a sat. $NH_4Cl$ solution are added, the reaction mixture is partitioned between water and toluene, the aqueous phase is extracted three times with toluene, and the combined org. phases are dried over $Na_2SO_4$. Removal of the solvent under reduced pressure leaves 35.8 g (99.5 mmol, 88%) of a solid, which can be employed in the subsequent reaction without further purification.

4,6,6,12,12-Pentamethyl-6,12-dihydroindeno[1,2-b]fluorene

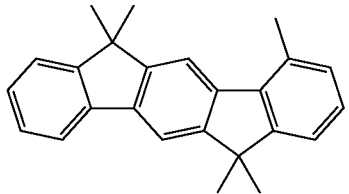 [SMILES: Cc1cccc2c1-c1cc3c(cc1C2(C)C)-c1ccccc1C3(C)C]

35.7 g (99 mmol) of the diol are dissolved in 350 ml of dichloromethane, the solution is cooled to −20° C., and a mixture of 90 g of polyphosphoric acid in 60 ml of methanesulfonic acid is added. After 30 min at −20° C., the reaction mixture is brought to room temperature overnight. 400 ml of EtOH are then added, and the mixture is heated at the boil for 1 h. The colourless precipitate is filtered off and washed twice with EtOH and heptane, giving the product shown above (33.5 g, 103 mmol, 99%), which can be employed in the subsequent reaction without further purification.

2,8-Dibromo-4,6,6,12,12-pentamethyl-6,12-dihydroindeno[1,2-b]-fluorene

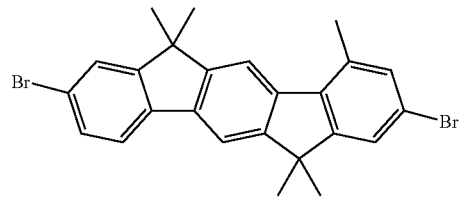 [SMILES: Cc1cc(Br)cc2c1-c1cc3c(cc1C2(C)C)-c1ccc(Br)cc1C3(C)C]

33.0 g (100 mmol) of methylindenofluorene are dissolved in 1000 ml of dichloromethane, and the solution is cooled to 10° C. and mixed with a solution of 30 g (244 mmol) of $Na_2CO_3$ in 750 ml of water. After addition of 10.4 ml of bromine (220 mmol), the suspension is stirred at 10° C. for 6 h, and the colourless solid is filtered off, washed with water, EtOH and heptane and dried, giving 27 g (56 mmol, 55%) of the product.

2,8-Dibromo-4,6,6,12,12-pentamethyl-6,12-dihydroindeno[1,2-b]-fluorene

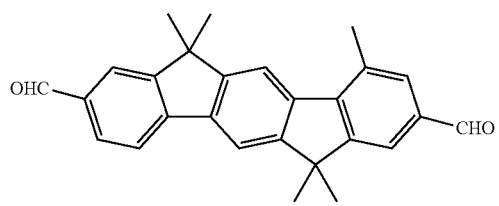 [SMILES: Cc1cc(C=O)cc2c1-c1cc3c(cc1C2(C)C)-c1ccc(C=O)cc1C3(C)C]

27 g (57 mmol) of dibromomethylindenofluorene are dissolved in 500 ml of diethyl ether, and the solution is cooled to 0° C. 69 ml (173 mmol) of n-BuLi are then added dropwise, and the mixture is stirred at 0° C. for 3 hours. 13 ml of DMF (173 mmol) are subsequently added dropwise. The reaction mixture is then stirred at room temperature for 8 h. After this time, 58 ml of a 1 N HCl solution are added, the reaction mixture is partitioned between water and toluene, the aqueous phase is extracted three times with toluene, and the combined org. phases are dried over Na$_2$SO$_4$ and evaporated. The residue is purified by column chromatography (silica gel, eluent dichloromethane:MeOH 9:1), giving 18 g (43 mmol, 75%) of the product.

4,6,6,12,12-Pentamethyl-6H,12H-indeno[1,2-b]fluorene-2,8-bis(1-phenyl-1H-benzimidazole) ETM2

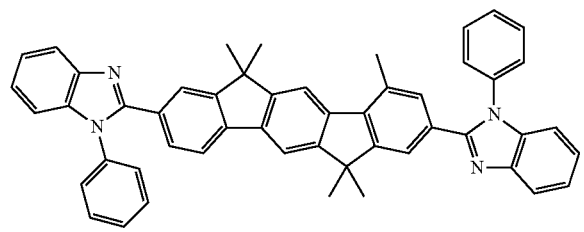 [SMILES: Cc1cc(-c2nc3ccccc3n2-c2ccccc2)cc2c1-c1cc3c(cc1C2(C)C)-c1ccc(-c2nc4ccccc4n2-c2ccccc2)cc1C3(C)C]

15 g (36 mmol) of the product from the preceding step are dissolved in 140 ml of dry DMF, and 6.6 g (36 mmol) of N-phenyl-o-phenylenediamine are added. 31 g (50.4 mmol) of potassium hydrogenmonopersulfate (oxone) are subsequently added, and the mixture is stirred for a further 1 h. The reaction mixture is slowly added in small portions to an aqueous K$_2$CO$_3$ solution. The solid present is dissolved in AcOEt, washed a number of times with water and dried. The product is subsequently recrystallised from toluene and acetonitrile (12.7 g, 18 mmol, 50%)

Example 1b

Preparation of 2,8-(5-methyl-2-thiophenyl)-4,6,6,12,12-pentamethyl-6,12-dihydroindeno[1,2-b]fluorene (HTM2)

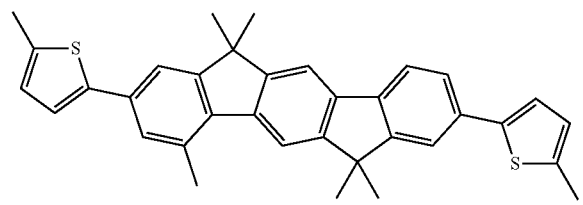

10.0 g (20.7 mmol) of 2,8-dibromo-4,6,6,12,12-pentamethyl-6,12-dihydroindeno[1,2-b]fluorene (step e) from Example 1a) are suspended in 300 ml of toluene. 60 ml of dioxane and 180 ml of water are added, and the suspension is degassed by passing in a protective gas for 30 min. 1.31 g (1.13 mmol, 5 mol %) of Pd(PPh$_3$)$_4$ and 29.58 g (90.8 mmol) of Cs$_2$CO$_3$ are added, and the mixture is degassed for a further 5 min. The reaction mixture is refluxed, and a solution of 13.93 g (90.8 mmol) of methylthiopheneboronic acid in 80 ml of dioxane is added dropwise. When the addition is complete, the mixture is stirred under reflux for 18 h, and the cooled reaction mixture is diluted with toluene, the phases are separated, washed with water, dried well over MgSO$_4$ and filtered through aluminium oxide and Celite. The product is crystallised from toluene/heptane and subsequently sublimed, giving 7.7 g (72%) of the product as a yellowish solid.

Example 1c

Preparation of 2,8-bis(4,6-di-p-tolyl-1,3,5-triazin-2-yl)-4,6,6,10,12,12-hexamethyl-6,12-dihydroindeno[1,2-b]fluorene (H2)

4,6,6,10,12,12-Hexamethyl-6,12-dihydroindeno[1,2-b]fluorene-2,8-diboronic acid

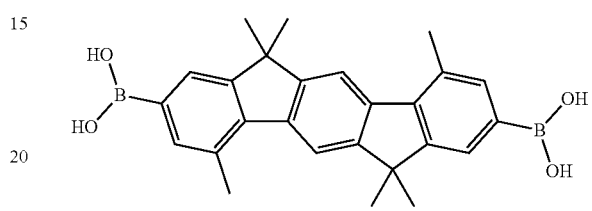

52 ml (130 mmol) of n-butyllithium (2.5 M in n-hexane) are added dropwise to a suspension of 24.5 g (50 mmol) of 2,8-dibromo-4,6,6,10,12,12-hexamethyl-6,12-dihydroindeno[1,2-b]fluorene in 1000 ml of THF at −78° C. with vigorous stirring, and the mixture is stirred for a further 2 h. 16.7 ml (150 mmol) of trimethyl borate are added in one portion to the red solution with vigorous stirring, the mixture is stirred at −78° C. for a further 30 min. and then warmed to room temperature over the course of 3 h, 300 ml of water are added, and the mixture is stirred for 30 min. The organic phase is separated off and evaporated to dryness in vacuo. The solid is taken up in 100 ml of n-hexane, filtered off with suction, washed once with 100 ml of hexane and dried in vacuo. Yield: 19 g (44.5 mmol), 91%, purity about 90% (NMR) of boronic acid, with varying amounts of boronic anhydride and borinic acid. The boronic acid can be used in this form without further purification.

2-Chloro-4,6-di-p-tolyl-1,3,5-triazine

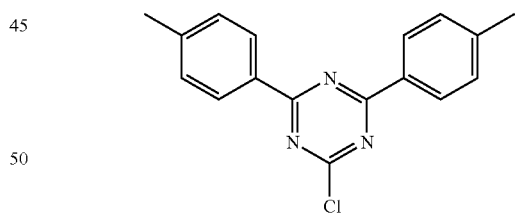

7.1 g of magnesium (292 mmol) are initially introduced in a 500 ml four-necked flask, and a solution of 50 g of bromo-p-toluene (292.3 mmol) in 200 ml of THF is slowly added dropwise. The reaction mixture is heated at the boil for 1.5 hours and subsequently cooled to room temperature. Cyanogen chloride (21.5 g, 117 mmol) in 200 ml of THF is initially introduced in a second flask and cooled to 0° C. The cooled Grignard reagent is then added dropwise at this temperature, and the mixture is stirred at RT for 12 h. After this time, 150 ml of HCl are added to the reaction mixture, and the aqueous phase is extracted three times with dichloromethane. The combined organic phases are washed with water and dried over Na$_2$SO$_4$ and evaporated. The residue is recrystallised from EtOH. The yield is 29.5 g (84%).

2,8-Bis(4,6-di-p-tolyl-1,3,5-triazin-2-yl)-4,6,6,10,12,12-hexamethyl-6,12-dihydroindeno[1,2-b]fluorene
H2

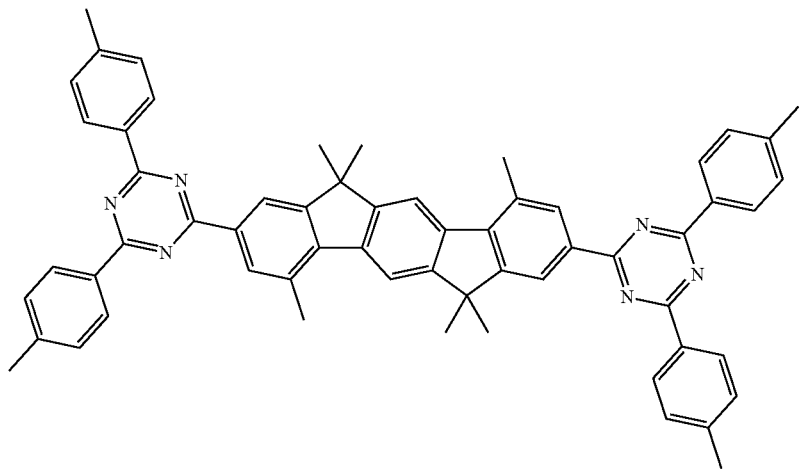

20 g (46.94 mmol) of 4,6,6,10,12,12-hexamethyl-6,12-dihydroindeno-[1,2-b]fluorene-2,8-diboronic acid, 27.7 g (93.9 mmol) of 2-chloro-4,6-di-p-tolyl-1,3,5-triazine and 41.9 g (197 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II)acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum (p=5×100$^{-5}$ mbar). The yield is 32.4 g (37.8 mmol), corresponding to 80.5% of theory, with the product having a purity, determined by RP-HPLC, of >99.9%.

Examples 1d-h

Preparation of compounds H4 to H8

7-Bromo-2-(2-nitrophenyl)-9,9-dimethyl-9H-fluorene

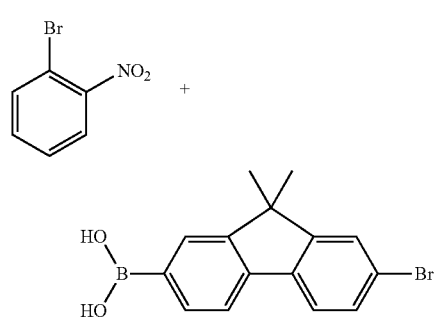

-continued

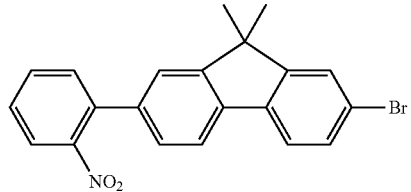

913 mg (3 mmol) of tri-o-tolylphosphine and then 112 mg (0.5 mmol) of palladium(II)acetate are added to a vigorously stirred suspension of 31.6 g (100 mmol) of 7-bromo-9,9-dimethylfluorenyl-2-boronic acid (CAS: 1213768-48-9), 20.6 g (102 mmol) of 1-bromo-2-nitrobenzene and 51 g (221 mmol) of tripotassium phosphate in a mixture of 380 ml of toluene, 190 ml of dioxane and 480 ml of water, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol and recrystallised three times from DMF (about 10 ml/g). Yield: 22.7 g (57 mmol, 58%).

2-Bromo-12,12-dimethyl-6,12-dihydro-6-azaindeno[1,2-b]fluorene

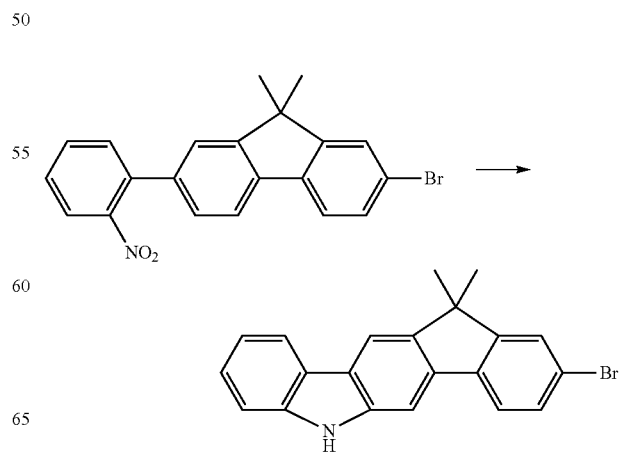

A mixture of 93.8 g (238 mmol) of 7-bromo-2-(2-nitrophenyl)-9,9-dimethyl-9H-fluorene and 290.3 ml (1669 mmol) of triethyl phosphite is heated under reflux for 12 h. The triethyl phosphite remaining is subsequently distilled off (72-76° C./9 mmHg). Water/MeOH (1:1) is added to the residue, and the solid is filtered off and recrystallised. Yield: 74 g (205 mmol, 87%).

12,12-Dimethyl-2-phenyl-6,12-dihydro-6-azaindeno[1,2-b]fluorene

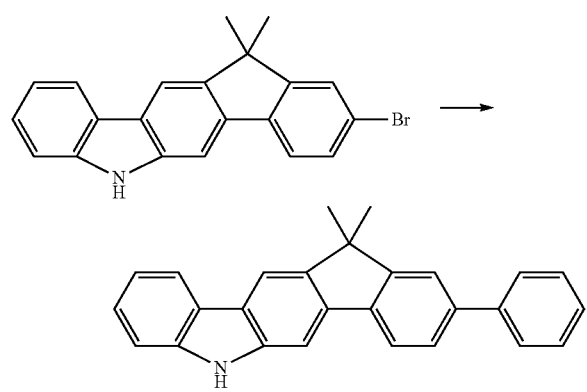

2.47 g (8.1 mmol) of tetrakis(triphenylphosphino)palladium(0) are added to a vigorously stirred suspension of 14.49 g (40 mmol) of 2-bromo-12,12-dimethyl-6,12-dihydro-6-azaindeno[1,2-b]fluorene, 3.69 g (40 mmol) of phenylboronic acid and 63.9 g (127 mmol) of $Na_2CO_3$ in 500 ml of DMF, and the mixture is subsequently heated under reflux for 16 h. After cooling, the precipitated solid is filtered off with suction, washed three times with 50 ml of toluene, three times with 50 ml of ethanol:water (1:1, v:v) and three times with 100 ml of ethanol and recrystallised three times from DMF (about 15 ml/g). Yield: 13 g (36 mmol, 91%).

2-Chloro-4,6-diphenylpyrimidine

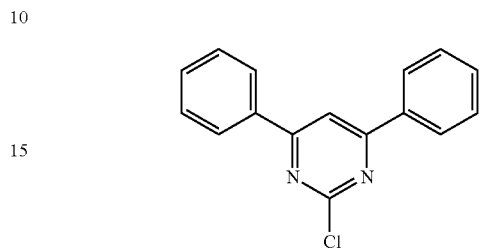

750 g (0.41 mmol) of 1,3,5-trichloropyrimidine, 100 g (0.82 mol) of phenylboronic acid and 625 ml of 4 M $NaHCO_3$ solution are suspended in 2.5 l of ethylene glycol dimethyl ether. 2.3 g (10.23 mmol) of $Pd(OAc)_2$ and 10.35 g (34 mmol) of $P(o\text{-}Tol)_3$ are added to this suspension, and the reaction mixture is heated under reflux for 16 h. The mixture is subsequently partitioned between ethyl acetate and water, and the organic phase is washed three times with water and dried over $Na_2SO_4$ and evaporated in a rotary evaporator. The residue remaining is recrystallised from heptane/toluene. The yield is 43 g (0.15 mol, 38%).

6-(4,6-Diphenylpyrimidin-2-yl)-12,12-dimethyl-2-phenyl-6,12-dihydro-6-azaindeno[1,2-b]fluorene and derivatives

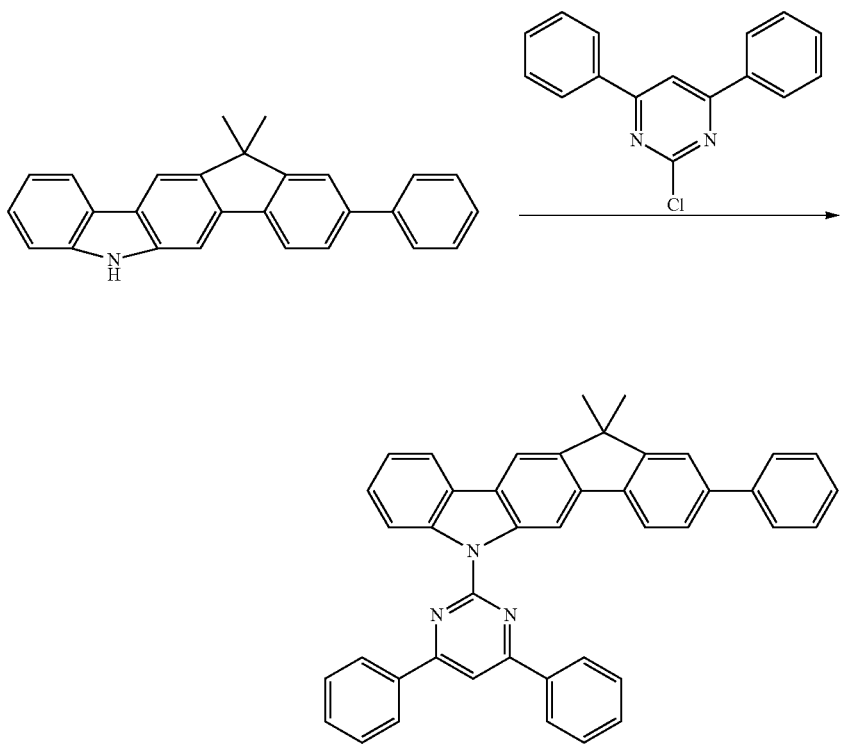

4.2 g of 60% NaH in mineral oil (106 mmol) are dissolved in 300 ml of dimethylformamide under a protective atmosphere. 38 g (106 mmol) of 12,12-dimethyl-2-phenyl-6,12-dihydro-6-azaindeno[1,2-b]fluorene are dissolved in 250 ml of DMF and added dropwise to the reaction mixture. After the mixture has been stirred at room temperature for 1 h, a solution of 2-chloro-4,6-diphenyl-1,3-pyrimidine (34.5 g, 0.122 mol) in 200 ml of THF is added dropwise. The reaction mixture is then stirred at room temperature for 12 h. After this time, the reaction mixture is poured onto ice and extracted three times with dichloromethane. The combined organic phases are dried over $Na_2SO_4$ and evaporated. The residue is extracted with hot toluene and recrystallised from toluene/n-heptane. The yield is 30.5 g (51 mmol, 49%).

The following compounds are obtained analogously:

| Starting material 1 | Starting material 2 | Product | Yield |
|---|---|---|---|
| | | | 74% |
| | | | 69% |

9-Bromo-6-(4,6-diphenylpyrimidin-2-yl)-12,12-dimethyl-2-phenyl-6,12-dihydro-6-azaindeno[1,2-b]fluorene and derivatives

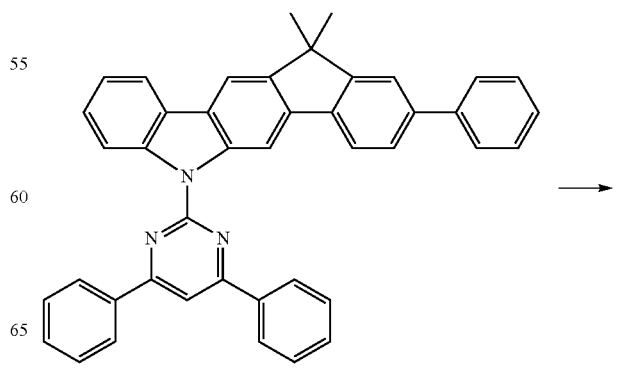

105

-continued

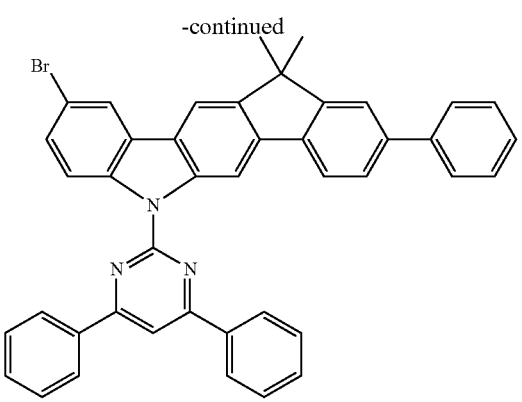

106

6-(4,6-Diphenylpyrimidin-2-yl)-12,12-dimethyl-2-phenyl-6,12-dihydro-6-azaindeno[1,2-b]fluorene-9-boronic acid and derivatives

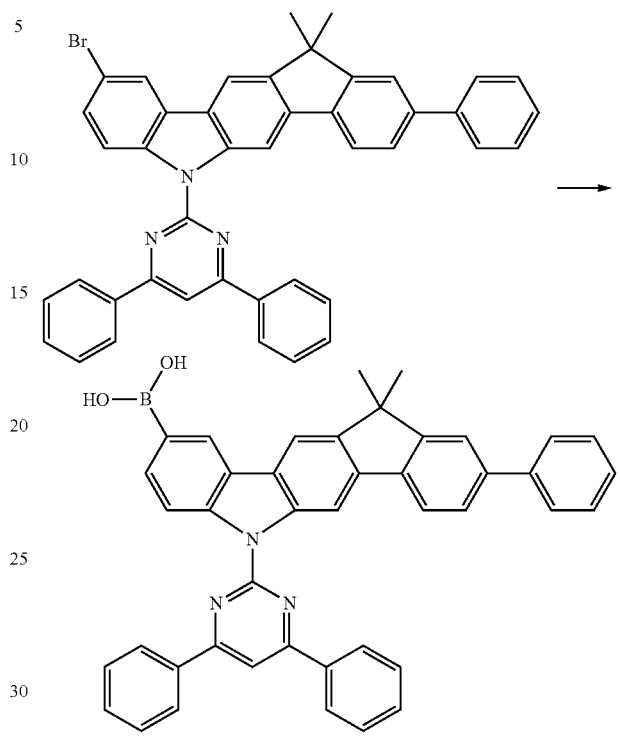

138 g (234.6 mmol) of 6-(4,6-diphenylpyrimidin-2-yl)-12,12-dimethyl-2-phenyl-6,12-dihydro-6-azaindeno[1,2-b]fluorene are initially introduced in 1000 ml of acetonitrile. A solution of 41.7 g (234.6 mmol) of NBS in 500 ml of $CH_3CN$ is subsequently added dropwise at −15° C. with exclusion of light, and the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction.

Yield: 94 g (140 mmol, 60%), purity according to $^1$H-NMR about 97%.

The following compounds are obtained analogously:

| Starting material | Product | Yield |
|---|---|---|
|  |  | 80% |
|  |  | 87% |

34 g (51 mmol) of 19-bromo-6-(4,6-diphenylpyrimidin-2-yl)-12,12-dimethyl-2-phenyl-6,12-dihydro-6-azaindeno[1,2-b]fluorene are dissolved in 600 ml of dry THF and cooled to −78° C. 26.2 ml (65.7 mmol/2.5 M in hexane) of n-BuLi are added at this temperature over the course of about 5 min., and the mixture is subsequently stirred at −78° C. for a further 2.5 h. 7.3 ml (65.7 mmol) of trimethyl borate are added as rapidly as possible at this temperature, and the reaction is slowly allowed to come to RT (about 18 h). The reaction solution is washed with water, and the precipitated solid and the organic phase are dried azeotropically with toluene. The crude product is washed by stirring with toluene/methylene chloride at about 40° C. and filtered off with suction, giving 26 g (83%) of the product as a white solid.

The following compounds are obtained analogously:

| Starting material | Product | Yield |
|---|---|---|
| (structure) | (structure) | 63% |
| (structure) | (structure) | 65% |

6-(4,6-Diphenylpyrimidin-2-yl)-12,12-dimethyl-2,9-diphenyl-6,12-dihydro-6-azaindeno[1,2-b]fluorene (H4) and derivatives (H5-H8)

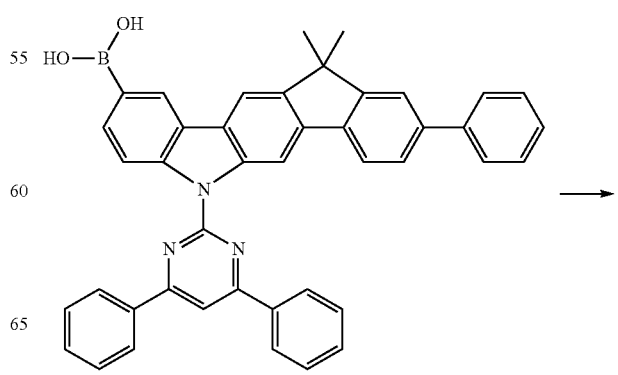

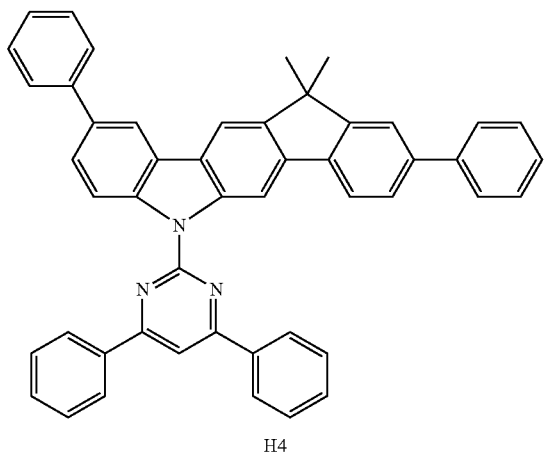

H4

26.6 g (42 mmol) of 6-(4,6-diphenylpyrimidin-2-yl)-12,12-dimethyl-2-phenyl-6,12-dihydro-6-azaindeno[1,2-b]fluorene-9-boronic acid and 8.2 g (52.4 mmol) of bromobenzene are dissolved in a degassed mixture of 135 ml of water, 315 ml of dioxane and 315 ml of toluene, and 5.33 g (50.31 mmol) of $Na_2CO_3$ are added. The reaction mixture is degassed, and 0.96 g (0.84 mmol) of tetrakistriphenylphosphinopalladium(0) is added. The mixture is heated under reflux for 18 h. After cooling, dichloromethane is added (heterogeneous mixture), the water phase is separated off, and the organic phase is evaporated azeotropically with toluene. The residue is extracted with hot toluene, recrystallised from toluene and finally sublimed in a high vacuum. The purity is 99.9%, the yield is 23 g (34 mmol, 82%).

The following compounds are obtained analogously:

| Starting material 1 | Starting material 2 | Product | Yield |
|---|---|---|---|
|  |  |  | 85% |
|  |  | H5 |  |
|  |  |  | 73% |
|  |  | H6 |  |

| Starting material 1 | Starting material 2 | Product | Yield |
|---|---|---|---|
| | | H7 | 77% |
| | | H8 | 69% |

Example 2

Use of Compounds According to the Invention as Electron-Transport Material in OLEDs OLEDs are produced by a general process in accordance with WO 04/058911, which is adapted to the circumstances described here (layer-thickness variation, materials used).

Glass plates coated with structured ITO (indium tin oxide) in a thickness of 150 nm are coated with 20 nm of PEDOT (spin-coated from water; purchased from H. C. Starck, Goslar, Germany; poly(3,4-ethylenedioxy-2,5-thiophene)) for improved processing. These coated glass plates are the substrates to which the OLEDs are applied. The layer sequence of the OLEDs is substrate/hole-injection layer (HIL1) 5 nm/hole-transport layer (HTM1) 140 nm/NPB 20 nm/emission layer (EML) 30 nm/electron-transport layer (ETM) 20 nm/LiF 1 nm/aluminium 100 nm. The emission layer is formed by a mixture of host material H1 with dopant D1, which is prepared by co-evaporation of the two materials. The emission layer comprises a proportion by volume of 95% of material H1 and a proportion by volume of 5% of emitting material D1.

The electron-transport materials in accordance with the prior art employed are $Alq_3$ and ETM1. The material according to the invention used is ETM2. The structures of the materials are summarised in Table 1.

All materials apart from PEDOT are applied by thermal vapour deposition in a vacuum chamber.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminance, calculated from current/voltage/luminance characteristic lines (IUL characteristic lines), and the lifetime are determined. The lifetime is defined as the time after which the luminance has dropped to half from a certain starting luminance. This value can be converted into a value for other starting luminances with the aid of conversion formulae known to the person skilled in the art. The lifetime for a starting luminance of 1000 cd/m² is the usual value quoted here.

The results for the OLEDs are shown in Table 2. The OLEDs of Examples C1, C2 and E1 exhibit a comparable lifetime of about 150 h from a starting luminance of 6000 cd/m², which corresponds to about 5500 h for a starting luminance of 1000 cd/m² on the basis of extrapolation formulae known to the person skilled in the art. A significant improvement with respect to efficiency, operating voltage and especially power efficiency is obtained through the use of compound ETM2 according to the invention. An approximately 70% increased power efficiency can be achieved compared with the prior art ETM1 through the use of compound ETM2 according to the invention (comparison of Examples C2 and E1).

Example 3

Use of Compounds According to the Invention as Electron-Blocking Material in OLEDs Further OLEDs are produced and characterised in accordance with the example indicated above, with the difference that a 20 nm thick layer of compound HTM2 according to the invention (see Table 1) is used as electron-blocking material (EBM) instead of the 20 nm thick NPB layer in accordance with the prior art. The results for the corresponding OLEDs can be seen in Table 3 (Examples E2 and E3). For reasons of clarity, OLEDs C1 and C2 in accordance with the prior art, which were mentioned in Example 2, are shown again. If the data for OLEDs C1 and C2 are compared, it can be seen that a significant improvement in the external quantum efficiency, current efficiency and operating voltage arises on use of compound HTM2 according to the invention. This results in a significant increase in the power efficiency of about 30%. On use of electron-transport material ETM1 in combination with HTM2 as EBM, an increase in the power efficiency of somewhat more than 25% can be achieved compared with the use of NPB.

Besides the improvement in the efficiency, an increase in the lifetime is also obtained on use of compound HTM2 according to the invention as electron-blocking material. Whereas the lifetime for a starting luminance of 6000 cd/m² is about 150 h for Examples C1 and C2 in accordance with the prior art, this is about 30% higher in the OLEDs of Examples E2 and E3, i.e. about 200 h. On use of compound HTM2 as EBM, an extrapolated lifetime of about 7200 h is thus obtained for a starting luminance of 1000 cd/m².

Example 4

Use of Compounds According to the Invention as Host Material for Phosphorescent Dopants Further OLEDs are produced and characterised as described in Example 2, where the layer structure is adapted as follows: substrate/HTM1 20 nm/NPB 20 nm/emission layer (EML) 30 nm/optional hole-blocking layer (HBL) 10 nm/Alq$_3$ 20 nm/LiF 1 nm/aluminium 100 nm. The structure of the emission and hole-blocking layers and the performance data of the resultant OLEDs are revealed by Table 4. Compounds H3 and CBP are employed as host material in accordance with the prior art (Examples C3-C5) and compared with compounds H2 and H4-H8 according to the invention (Examples E4-E13). Compounds TER1 and TER2 are employed as red-emitting dopants.

On use of compound H2 according to the invention without a hole-blocking layer (C2, C3 and E4 and E5), a moderate improvement in the lifetime is achieved, but in particular significantly improved power efficiency can be achieved through the significant reduction in the operating voltage at the same time as somewhat improved current efficiency. The improvement is about 50% (comparison of E4 and C3).

If a triply doped emission layer comprising CBP as co-dopant and an additional hole-blocking layer (Examples C5 and E6) are used, a significant increase in the lifetime of about 45% can be achieved on use of the compounds according to the invention. The power efficiency can also be increased in this case. The improvement in this case is somewhat greater than 10%. The use of the further compounds according to the invention in some cases enables even greater improvements to be achieved, as revealed by Table 4.

TABLE 1

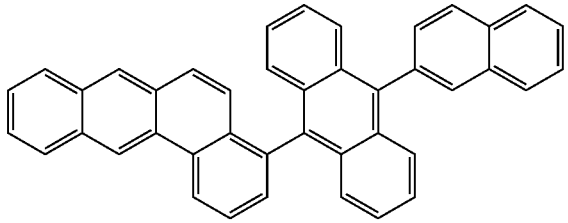 [SMILES: c1ccc2cc(-c3c4ccccc4c(-c4cccc5c4ccc4cc6ccccc6cc45)c4ccccc34)ccc2c1]

H1

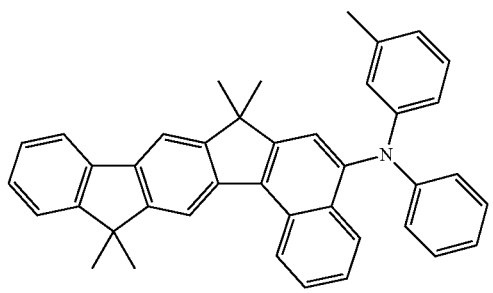 [SMILES: Cc1cccc(N(c2ccccc2)c2cc3c(c4ccccc24)-c2cc4c(cc2C3(C)C)-c2ccccc2C4(C)C)c1]

D1

TABLE 1-continued
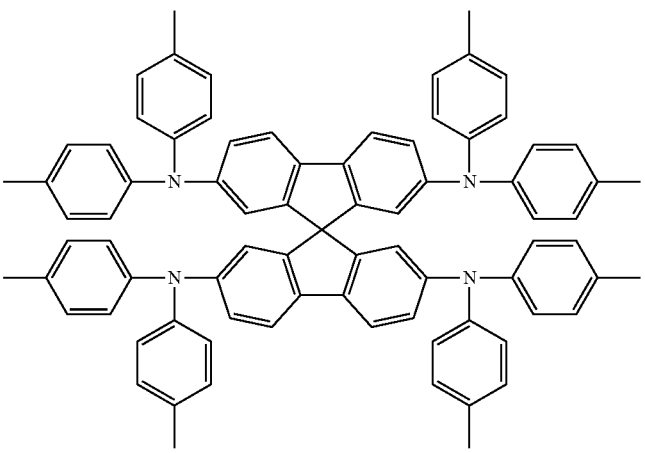
HTM1
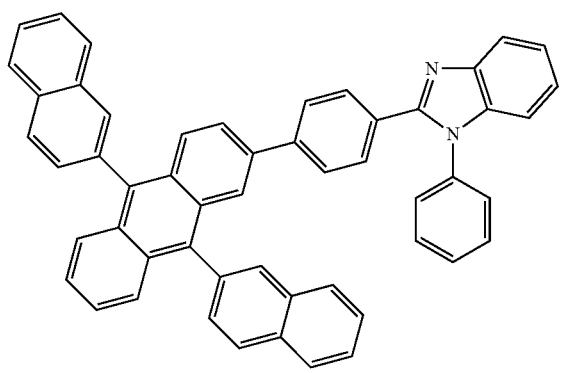 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM1
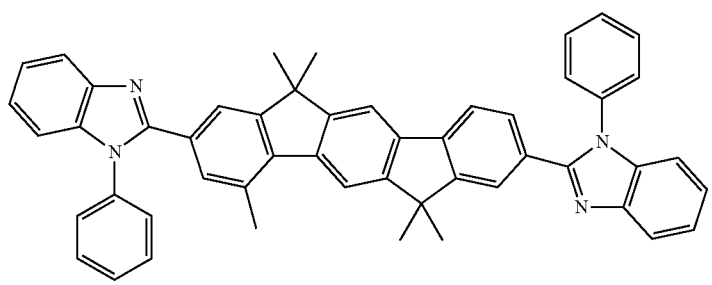 [SMILES: Cc1cc(-c2nc3ccccc3n2-c2ccccc2)cc2c1-c1cc3c(cc1C2(C)C)-c1ccc(-c2nc4ccccc4n2-c2ccccc2)cc1C3(C)C]
ETM2
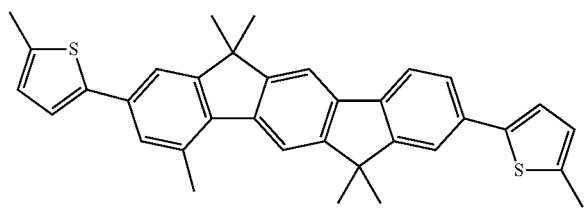
HTM2

TABLE 1-continued
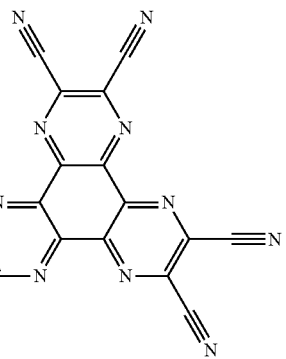  HIL1
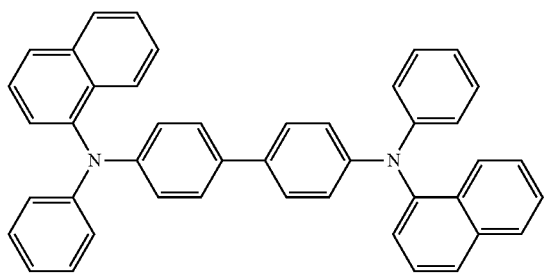 [SMILES: c1ccc(N(c2ccc(-c3ccc(N(c4ccccc4)c4cccc5ccccc45)cc3)cc2)c2cccc3ccccc23)cc1]  NPB
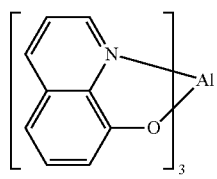  Alq3
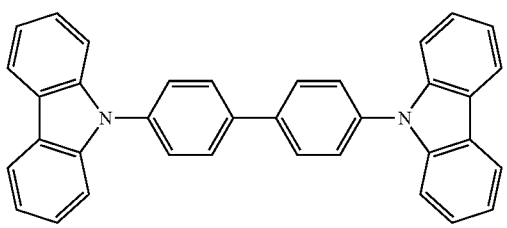 [SMILES: c1ccc2c(c1)c1ccccc1n2-c1ccc(-c2ccc(-n3c4ccccc4c4ccccc43)cc2)cc1]  CBP
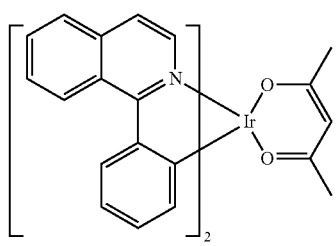  TER1
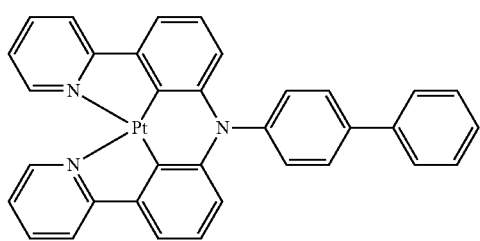  TER2

TABLE 1-continued
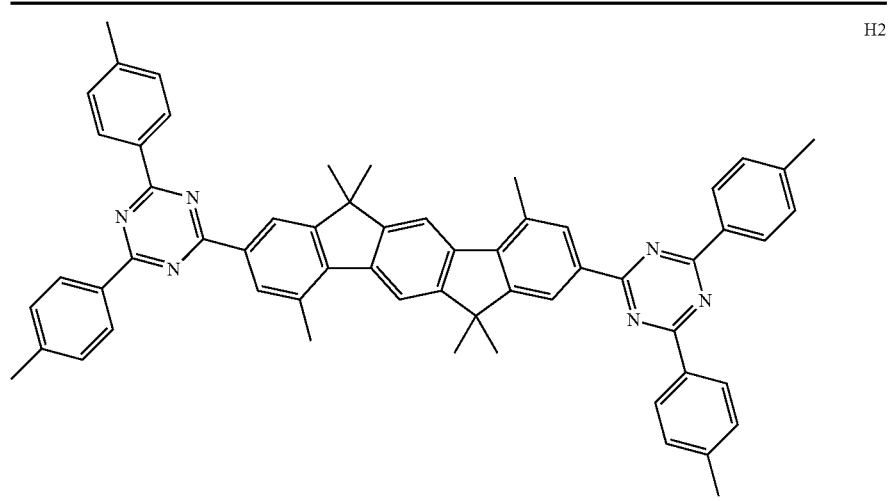
H2
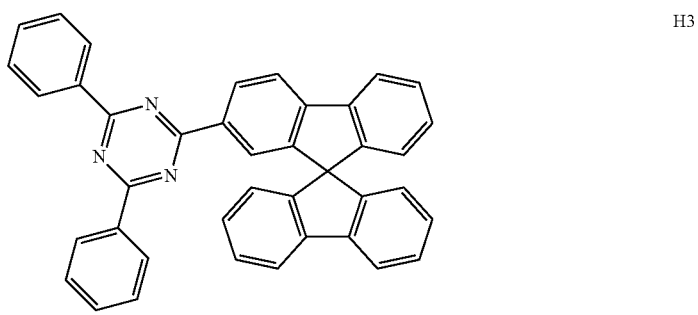
H3
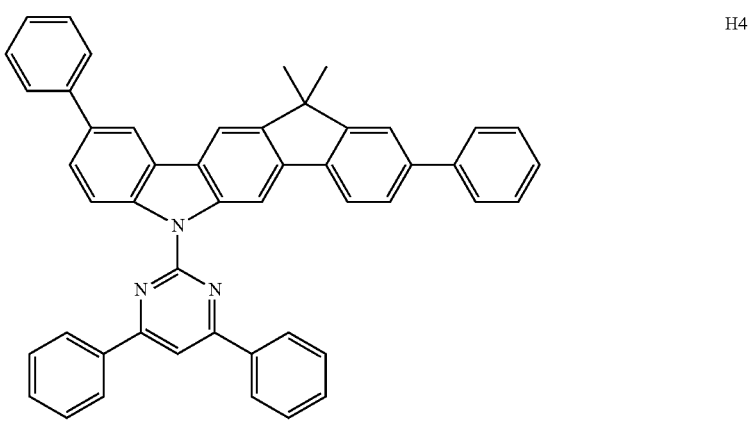
H4
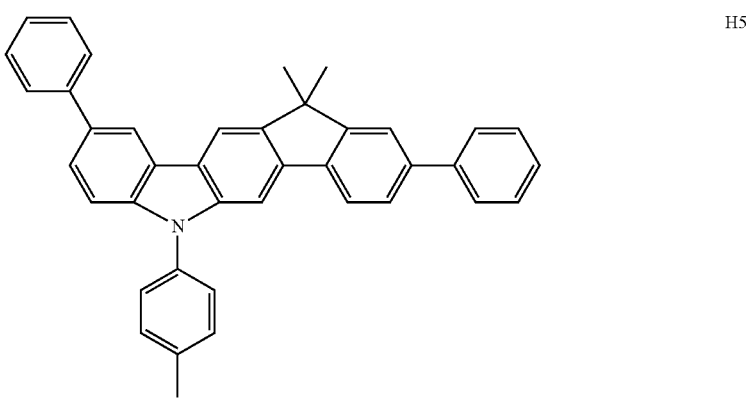
H5

TABLE 1-continued
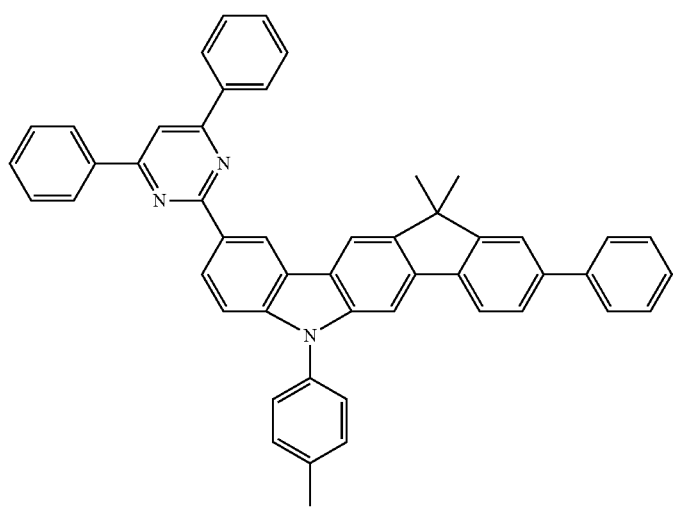
H6
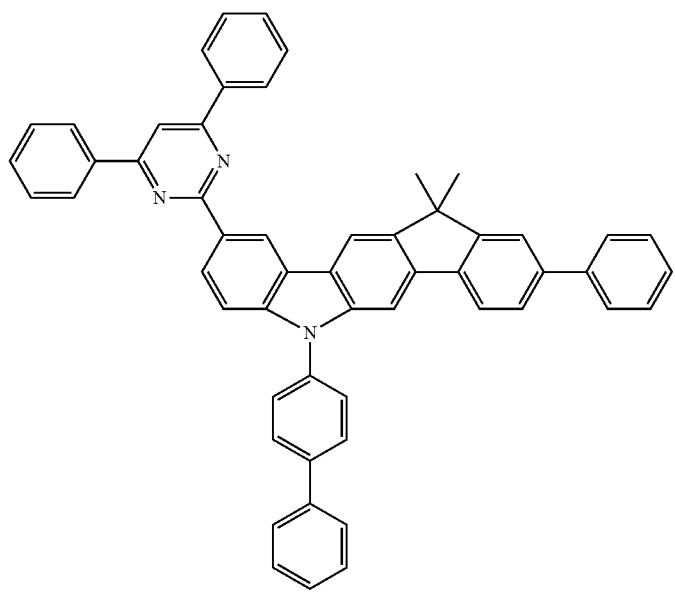 [SMILES: CC1(C)c2cc(-c3ccccc3)ccc2-c2cc3c(cc21)c1cc(-c2nc(-c4ccccc4)cc(-c4ccccc4)n2)ccc1n3-c1ccc(-c2ccccc2)cc1]
H7
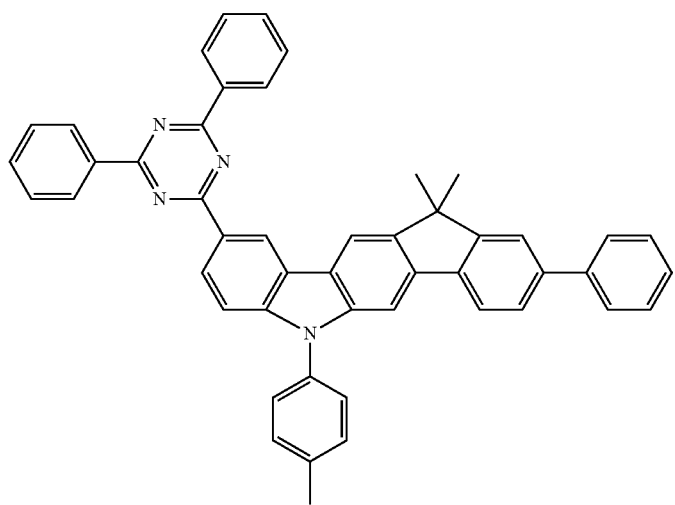 [SMILES: Cc1ccc(-n2c3ccc(-c4nc(-c5ccccc5)nc(-c5ccccc5)n4)cc3c3cc4c(cc32)-c2ccc(-c3ccccc3)cc2C4(C)C)cc1]
H8

TABLE 2

| Ex. | ETM | Voltage for 1000 cd/m² | Efficiency at 1000 cd/m² | Efficiency at 1000 cd/m² | EQE at 1000 cd/m² | CIE x/y at 1000 cd/m² |
|---|---|---|---|---|---|---|
| C1 comp. | Alq$_3$ | 6.4 V | 5.1 cd/A | 2.5 lm/W | 4.2% | 0.142/0.151 |
| C2 comp. | ETM1 | 6.2 V | 5.9 cd/A | 3.0 lm/W | 4.7% | 0.141/0.160 |
| E1 | ETM2 | 4.9 V | 8.1 cd/A | 5.2 lm/W | 6.9% | 0.143/0.156 |

TABLE 3

| Ex. | EBM | ETM | Voltage for 1000 cd/m² | Efficiency at 1000 cd/m² | Efficiency at 1000 cd/m² | EQE at 1000 cd/m² | CIE x/y at 1000 cd/m² |
|---|---|---|---|---|---|---|---|
| C1 (comp.) | NPB | Alq$_3$ | 6.4 V | 5.1 cd/A | 2.5 lm/W | 4.2% | 0.142/0.151 |
| C2 (comp.) | NPB | ETM1 | 6.2 V | 5.9 cd/A | 3.0 lm/W | 4.7% | 0.141/0.160 |
| E2 | HTM2 | Alq$_3$ | 5.9 V | 6.0 cd/A | 3.2 lm/W | 4.9% | 0.141/0.153 |
| E3 | HTM2 | ETM1 | 5.7 V | 6.9 cd/A | 3.8 lm/W | 5.5% | 0.142/0.159 |

TABLE 4

| Ex. | EML | HBL | Voltage for 1000 cd/m² | Efficiency at 1000 cd/m² | Efficiency at 1000 cd/m² | CIE x/y at 1000 cd/m² | Lifetime from 1000 cd/m² |
|---|---|---|---|---|---|---|---|
| C3 (comp.) | H3:TER1 (85%:15%) | — | 5.0 V | 7.2 cd/A | 4.5 lm/W | 0.69/0.31 | 14000 h |
| C4 (comp.) | H3:TER2 (85%:15%) | — | 6.5 V | 9.0 cd/A | 4.3 lm/W | 0.66/0.33 | 18000 h |
| C5 (comp.) | H3:CBP:TER1 (45%:45%:10%) | H3 | 5.2 V | 8.1 cd/A | 4.9 lm/W | 0.68/0.32 | 15000 h |
| E4 | H2:TER1 (85%:15%) | — | 4.3 V | 9.3 cd/A | 6.8 lm/W | 0.69/0.32 | 15000 h |
| E5 | H2:TER2 (85%:15%) | — | 5.8 V | 9.5 cd/A | 5.1 lm/W | 0.66/0.33 | 18000 h |
| E6 | H2:CBP:TER1 (45%:45%:10%) | H3 | 4.9 V | 8.7 cd/A | 5.6 lm/W | 0.68/0.32 | 20000 h |
| E7 | H4:TER1 (85%:15%) | — | 4.3 V | 7.8 cd/A | 5.7 lm/W | 0.69/0.31 | 19000 h |
| E8 | H4:TER2 (85%:15%) | — | 5.5 V | 10.4 cd/A | 5.9 lm/W | 0.66/0.33 | 23000 h |
| E9 | H3:H5:TER1 (45%:45%:10%) | H3 | 4.8 V | 7.5 cd/A | 4.9 lm/W | 0.68/0.32 | 22000 h |
| E10 | H6:TER1 (85%:15%) | — | 4.2 V | 7.5 cd/A | 5.6 lm/W | 0.69/0.31 | 16000 h |
| E11 | H7:TER1 (45%:45%:10%) | H3 | 4.6 V | 8.3 cd/A | 5.7 lm/W | 0.69/0.31 | 22000 h |
| E12 | H8:TER1 (85%:15%) | — | 4.4 V | 8.7 cd/A | 6.3 lm/W | 0.69/0.31 | 17000 h |
| E13 | H8:CBP:TER1 (45%:45%:10%) | H3 | 5.0 V | 9.3 cd/A | 5.8 lm/W | 0.68/0.32 | 18000 h |

The invention claimed is:
1. A compound of the formula (2a) or (4a)

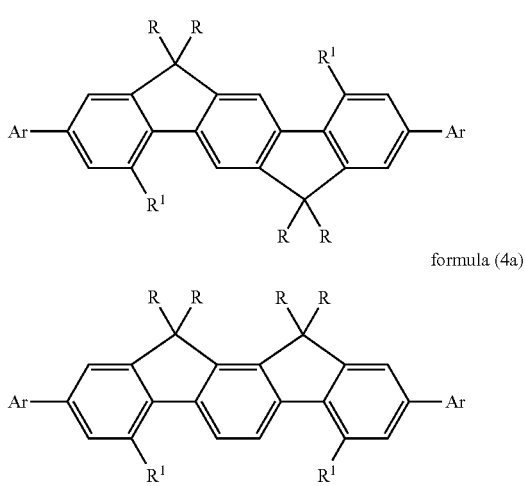

formula (2a)

formula (4a)

where the following applies to the symbols and indices used:

Ar is furan, benzofuran, isobenzofuran, dibenzofuran, thiophene, benzothiophene, isobenzothiophene, dibenzothiophene, pyrrole, indole, isoindole, carbazole, pyrazole, indazole, imidazole, benzimidazole, naphthimidazole, phenanthrimidazole, pyridi-midazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, azacarbazole, benzocarboline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, tetrazole, purine, indolizine, benzothiadiazole, each of which is optionally substituted by one or more radicals R;

R which are part of the 5 membered cyclic ring in the embodiment —C(R)$_2$—, are on each occurrence, independently of one another, from a straight-chain alkyl or alkoxy group having 1 to 20 C atoms or a branched or cyclic alkyl or alkoxy group having 3 to 20 C atoms, each of which may be substituted by one or more radicals R$^3$, where one or more CH$_2$ groups may be replaced by —C≡C—, —R$^3$=CR$^3$—, —NR$^3$—, —O—, or —S—, or an aryl or heteroaryl group having 5 to 30 aromatic ring atoms, which may in each case be substituted by one or more radicals R$^3$, R$^1$ is selected on each occurrence, independently of one another, from H, or a straight-chain alkyl having 1 to 8 C atoms, R$^3$ is on each occurrence, identically or differently, H, F or an aliphatic, aromatic and/or heteroaromatic organic radical having 1 to 20 C atoms, in which, in addition, one or more H atoms is optionally replaced by F; two or more identical or different substituents R$^3$ here may also be linked to one another and form a mono- or polycyclic, aliphatic or aromatic ring system.

2. An organic electroluminescent device comprising the compound according to claim 1.

* * * * *